US010092631B2

(12) United States Patent
Turkel et al.

(10) Patent No.: US 10,092,631 B2
(45) Date of Patent: Oct. 9, 2018

(54) METHODS FOR TREATING HEADACHE

(71) Applicant: Allergan, Inc., Irvine, CA (US)

(72) Inventors: Catherine C. Turkel, Newport Coast, CA (US); Mitchell F. Brin, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 15/412,392

(22) Filed: Jan. 23, 2017

(65) Prior Publication Data

US 2017/0128552 A1 May 11, 2017

Related U.S. Application Data

(63) Continuation of application No. 14/797,552, filed on Jul. 13, 2015, now Pat. No. 9,555,085, which is a continuation of application No. 12/256,655, filed on Oct. 23, 2008, now Pat. No. 9,078,893, which is a continuation of application No. 11/329,598, filed on Jan. 11, 2006, now Pat. No. 7,704,511, which is a continuation of application No. 11/319,880, filed on Dec. 28, 2005, now abandoned, which is a continuation of application No. 11/039,506, filed on Jan. 18, 2005, now abandoned, which is a continuation-in-part of application No. 10/789,180, filed on Feb. 26, 2004, now Pat. No. 9,078,892.

(51) Int. Cl.
A61K 39/38 (2006.01)
A61K 38/48 (2006.01)
A61K 9/00 (2006.01)

(52) U.S. Cl.
CPC ........ *A61K 38/4893* (2013.01); *A61K 9/0019* (2013.01); *C12Y 304/24069* (2013.01)

(58) Field of Classification Search
None
See application file for complete search history.

(56) References Cited

U.S. PATENT DOCUMENTS

| | | |
|---|---|---|
| 5,437,291 A | 8/1995 | Pasricha et al. |
| 5,670,484 A | 9/1997 | Binder |
| 5,714,468 A | 2/1998 | Binder |
| 5,766,605 A | 6/1998 | Sanders et al. |
| 5,989,545 A | 11/1999 | Foster et al. |
| 6,063,768 A | 5/2000 | First |
| 6,139,845 A | 10/2000 | Donovan |
| 6,299,893 B1 | 10/2001 | Schwartz et al. |
| 6,306,423 B1 | 10/2001 | Donovan et al. |
| 6,312,708 B1 | 11/2001 | Donovan |
| 6,358,917 B1 | 3/2002 | Carruthers et al. |
| 6,423,319 B1 | 7/2002 | Brooks et al. |
| 6,447,787 B1 | 9/2002 | Gassner et al. |
| 6,458,365 B1 | 10/2002 | Aoki et al. |
| 6,464,986 B1 | 10/2002 | Aoki et al. |
| 6,623,742 B2 | 9/2003 | Voet |
| 6,787,517 B1 | 9/2004 | Gil et al. |
| 6,838,434 B2 | 1/2005 | Voet |
| 7,172,763 B2 | 2/2007 | Aoki et al. |
| 7,270,287 B2 | 9/2007 | First |
| 7,393,537 B2 | 7/2008 | Ackerman |
| 7,655,244 B2 * | 2/2010 | Blumenfeld ............... 424/239.1 |
| 7,704,511 B2 * | 4/2010 | Turkel ............... A61K 38/4893 424/184.1 |
| 7,824,694 B2 * | 11/2010 | First ..................... A61K 31/167 424/239.1 |
| 8,241,641 B2 * | 8/2012 | Blumenfeld ............... 424/239.1 |
| 8,258,096 B2 * | 9/2012 | Yeomans et al. ............ 514/11.6 |
| 8,470,337 B2 * | 6/2013 | Manack et al. ............ 424/247.1 |
| 8,501,195 B2 * | 8/2013 | Turkel ............... A61K 38/4893 424/236.1 |
| 8,530,425 B2 * | 9/2013 | Blumenfeld ................. 514/18.3 |
| 8,603,779 B2 * | 12/2013 | Foster et al. ................. 435/69.7 |
| 8,603,983 B2 * | 12/2013 | Blumenfeld ................. 514/18.3 |
| 8,609,112 B2 * | 12/2013 | Blumenfeld et al. ...... 424/247.1 |
| 8,609,113 B2 * | 12/2013 | Blumenfeld et al. ...... 424/247.1 |
| 8,617,569 B2 * | 12/2013 | Binder ....................... 424/239.1 |
| 8,617,571 B2 * | 12/2013 | Blumenfeld ............... 424/247.1 |
| 8,691,769 B2 * | 4/2014 | Borodic ............. A61K 38/4893 514/18.3 |
| 8,734,810 B2 * | 5/2014 | Blumenfeld ............... 424/239.1 |
| 8,846,622 B2 * | 9/2014 | Blumenfeld ......... A61K 9/0014 424/239.1 |
| 8,889,151 B2 * | 11/2014 | Turkel ............... A61K 38/4893 424/184.1 |

(Continued)

FOREIGN PATENT DOCUMENTS

DE 101 50 415 A1 5/2003
WO WO 95/30431 11/1995

(Continued)

OTHER PUBLICATIONS

Robertson et al, Neuropsychiatric Disease and Treatment, (2012) vol. 8, pp. 35-48*
Conidi, Curr. Pain Headache Rep., 2016, 20:40, 8 pages*
Porta et al, J. Headache Pain, 2005, 6:325-327*
Carruthers et al, Headache, 1999, 39:682-665.*
Delstanche et al Acta Neurol. Belg, 110:221-229.*
Gady et al, Connecticut Medicine, Mar. 2813, 77/3:165-166.*
Headache, Tension—In-Depth Report—NY Times Health, The New York Times, http://www.nytimes.com/health/guides/disease/tension-headache/print.html Sep. 10, 2015.*
O'Day, Current Opinion in Ophthalmology 2001, 12:419-422.*
Silberstein et al, Cephalalgia, 2006, 26:790-800.*

(Continued)

*Primary Examiner* — Nita M Minnifield
(74) *Attorney, Agent, or Firm* — Brigitte C. Phan

(57) ABSTRACT

A headache can be treated more effectively by co-administration of a botulinum toxin and a triptan drug to a patient and/or the effectiveness of a triptan medication can be increased. The botulinum toxin can be botulinum toxin type A and the botulinum toxin can be administered to or to the vicinity of where a patient experiences or is predisposed to experience pain or a headache.

8 Claims, 16 Drawing Sheets

(56) References Cited

U.S. PATENT DOCUMENTS

| | | | |
|---|---|---|---|
| 8,936,790 B2* | 1/2015 | Turkel | A61K 38/4893 424/236.1 |
| 8,940,308 B2* | 1/2015 | Turkel | A61K 38/164 424/236.1 |
| 8,968,747 B2* | 3/2015 | Turkel | A61K 38/4893 424/236.1 |
| 9,061,025 B2* | 6/2015 | Burstein | A61K 38/4893 |
| 9,078,892 B2* | 7/2015 | Turkel | A61K 38/4893 |
| 9,078,893 B2* | 7/2015 | Turkel | A61K 38/4893 |
| 9,279,001 B2* | 3/2016 | Turkel | A61K 38/4893 |
| 9,555,085 B2* | 1/2017 | Turkel | A61K 38/4893 |
| 9,827,297 B2* | 11/2017 | Blumenfeld | A61K 38/4893 |
| 9,943,576 B2* | 4/2018 | Forssen | A61K 38/4893 |
| 2003/0224019 A1 | 12/2003 | O'Brien | |
| 2004/0009180 A1 | 1/2004 | Donovan | |
| 2005/0123567 A1 | 6/2005 | First | |
| 2005/0238664 A1* | 10/2005 | Hunt | 424/239.1 |
| 2005/0238667 A1* | 10/2005 | Hunt | 424/239.1 |
| 2006/0104995 A1* | 5/2006 | Turkel et al. | 424/239.1 |
| 2006/0121057 A1* | 6/2006 | Turkel et al. | 424/239.1 |
| 2006/0171963 A1 | 8/2006 | Blumenfeld | |
| 2006/0268575 A1* | 11/2006 | Le et al. | 362/611 |
| 2008/0021437 A1* | 1/2008 | Boyd | 604/514 |
| 2008/0213315 A1* | 9/2008 | Hunt | 424/239.1 |
| 2009/0232850 A1* | 9/2009 | Manack et al. | 424/239.1 |
| 2009/0304748 A1* | 12/2009 | Hunt | 424/239.1 |
| 2010/0189655 A1* | 7/2010 | Turkel et al. | 424/9.2 |
| 2012/0053126 A1* | 3/2012 | Turkel et al. | 514/18.3 |
| 2012/0237548 A1* | 9/2012 | Hunt | 424/239.1 |
| 2013/0150307 A1* | 6/2013 | Turkel et al. | 514/17.6 |
| 2013/0224180 A1* | 8/2013 | Turkel et al. | 424/91.67 |
| 2013/0251830 A1* | 9/2013 | Manack et al. | 424/780 |
| 2013/0296259 A1* | 11/2013 | Hunt | 514/21.2 |
| 2013/0330321 A1* | 12/2013 | Turkel et al. | 424/94.67 |
| 2014/0030248 A1* | 1/2014 | Turkel et al. | 424/94.67 |
| 2014/0044695 A1* | 2/2014 | Hunt | 424/94.3 |
| 2014/0079687 A1* | 3/2014 | Blumenfeld | A61K 38/4893 424/94.67 |
| 2014/0099294 A1* | 4/2014 | Dolly et al. | 424/94.3 |
| 2014/0199288 A1* | 7/2014 | Hunt | 424/94.67 |
| 2014/0294803 A1* | 10/2014 | Turkel et al. | 424/94.67 |
| 2014/0303124 A1* | 10/2014 | Burstein | A61K 31/366 514/167 |
| 2014/0343041 A1* | 11/2014 | Chapin | A61K 31/5377 514/214.02 |
| 2016/0074485 A1* | 3/2016 | Turkel | A61K 9/0019 424/94.67 |
| 2016/0175409 A1* | 6/2016 | Turkel | A61K 38/4893 424/94.67 |
| 2016/0263202 A1* | 9/2016 | Blumenfeld | A61K 38/4893 |
| 2017/0128552 A1* | 5/2017 | Turkel | A61K 38/4893 |
| 2017/0224786 A1* | 8/2017 | Hunt | A61K 38/4893 |
| 2018/0028624 A1* | 2/2018 | Turkel | A61K 38/4893 |
| 2018/0078622 A1* | 3/2018 | Blumenfeld | A61K 38/4893 |

FOREIGN PATENT DOCUMENTS

| | | |
|---|---|---|
| WO | WO 03/011333 | 2/2003 |
| WO | WO 2014/130581 A1 * | 8/2014 |

OTHER PUBLICATIONS

Winner, Phys Med Rahabil Clin Am, 2903, 14:885-899.*
Silberstein et al, Headache, 2600, 40:445-450.*
Diener et al, European Journal of Neurology 2014, 21: 851-859.*
Mathew et al, Headache 2005;45:293-307.*
Jabbari, NAture Clinical Practice Neurology. Dec. 2008, 4/12:676-685.*
Schulte-Matter et al, Eur J Neurol. Feb. 2006; 13 Suppl 1:51-4.*
U.S. Appl. No. 60/418,789, filed Oct. 15, 2002, Katz, Howard.
Aoki K., et al, *Mechanisms of the antinociceptive effect of subcutaneous Botox: Inhibition of peripheral and central nociceptive processing*, Cephalalgia Sep. 2003;23(7):649.
Aoki KR. Evidence for antinociceptive activity of botulinum toxin type A in pain management. Headache 2003:42 Suppl 1:S9-15.
Aoki KR. Pharmacology and immunology of botulinum toxin serotypes. J Neurol 2001;248 Suppl 1:1/3-1/10.
Aoki, K., et al., *Botulinum toxin type A and other botulinum toxin serotypes: a comparative review of biochemical and pharmacological action*, Eur J. Neurol 2001: (suppl 5); 21-29.
Aoki, K., *Physiology and pharmacology of therapeutic botulinum neurotoxins*, in Kreyden, O., editor, Hyperhydrosis and botulinum toxin in dermatology, Basel Karger; 2002; 30: pp. 107-116, at 109-110.
Bhattacharya K., et al., *Novel uses of botulinum toxin type A: two case reports*, Mov Disord 2000; 15(Suppl 2):51-52.
Bigal ME, Sheftell FD, Rapoport AM, et al. Chronic daily headache in a tertiary care population: correlation between International Headache Society diagnostic criteria and proposed revisions of criteria for chronic daily headache. Cephalalgia 2002;22:432-438.
Bigalke H., et al., *Botulinum A Neurotoxin Inhibits Non-Cholinergic Synaptic Transmission in Mouse Spinal Cord Neurons in Culture*, Brain Research 360;318-324:1985.
Bigalke H., et al., *Tetanus Toxin and Botulinum A Toxin Inhibit Release and Uptake of Varous Transmitters, as Studied and Particulate Prepartations From Rat Brain and Spinal Cord*, Naunyn-Schmiedeberg's Arch Pharmacol 316;244-251:1981.
Binder WJ, Brin MF, Blitzer A. Botulinum Toxin Type A (BOTOX) for treatment of migraine headaches: an open-label study. Otolaryngol Head Neck Surg 2000;123(6):669-676.
Binz T. et al., *The Complete Sequence of Botulinum Neurotoxin Type A and Comparison with Other Clostridial Neurotoxins*, J Biological Chemistry 265(16);9153-9158:1990.
Blugerman G., et al., *Multiple eccrine hidrocystomas: A new therapeutic option with botulinum toxin*, Dermatol Surg May 2003;29(5):557-9.
Blumefeld AM, Dodick DW, Siberstein SD. Botulinum neurotoxin for the treatment of migraine and other primary headache disorders. Dermatol Clin 2004;22:167-175.
Blumefeld AM. Botulinum toxin type A as an effective prophylactic treatment in primary headache disorders. Headache 2003;43:853-860.
BOTOX® (package insert). Irvine, California: Allergan Inc; 2004.
Brandes JL, Saper JR, Diamond M, et al. Topiramate for migraine prevention: a randomized controlled trial. JAMA:2004;291:965-973.
Brem, H., et al, *Placebo-Controlled Trial of Safety and Efficacy of Intraoperative Controlled Delivery by Biodegradable Polymers of Chemotherapy of Recurrent Gliomas*, Lancet 345;1008-1012:1995.
Brin et al., *Report of the Therapeutics and Technology Assessment Subcommittee of the American Academy of Neurology*, Neurology, 40:1332-1336, 1990.
Brin MF, Fahn S, Moskowitz C, et al. Localized injections of botulinum toxin for the treatment of focal dystonia and hemifacial spasm. Movement Dis 1987;2:237-254.
Brin MF, Swope DM, O'Brien C, et al. BOTOX® for migraine: double-blind, placebo-controlled, region-specific evaluation. Cephalalgia 2000;20:421-422.
Brin, M., et al., *Botulinum toxin type A: pharmacology*, in Mayer N., editor, Spesticity: etiology, evaluation, management and the role of botulinum toxin, 2002; pp. 110-124, at 112-113.
Bushara K., *Botulinum toxin and rhinorrhea*, Otolaryngol Head Neck Surg 1996; 114(3):507.
Castillo JP, Munoz P, Guitera V, et al. Epidemiology of chronic daily headache in the general population. Headache 1999;39:190-196.
Cheshire WP, Abashian SW, Mann JD. Botulinum toxin in the treatment of myofacial pain syndrome. Pain 1994;59:65-69.
Colas R, Munoz P, Temprano R, et al. Chronic daily headache with analgesic overuse: epidemiology and impact on quality of life. Neurology 2004;62:1338-1342.
Couch JR. Placebo effect and clinical trials in migraine therapy. Meth Prob Migraine Trials, Neuroepid 1987;6:178-185.
Cui M, Khanijou S, Rubino J, et al. Subcutaneous administration of botulinum toxin A reduces formalin-induced pain. Pain 2004:107:125-133.

(56) References Cited

OTHER PUBLICATIONS

Cui, M., et al., *Mechanisms of the antiociceptive effect of subcutaneous BOTOX® inhibition of peripheral and central nociceptive processing*, Nauyn Schmiedebers Arch Pharmacol 2002; 365 (supp 2): R17.

Dabrowski et al.; *Botulinum toxin as a novel treatment for self mutilation in Lesch-Nyhan syndrome*, Ann Neurol Sep. 2002;52(3 Supp 1):S157.

Depakot® ER (package insert). Abbottt Laboratories; 2003.

Dowson, A.J., et al., *Managing Chronic Headaches in the Clinic*, Int J. Clin Pract., Dec. 2004, 58, 12, pp. 1142-1151.

Duggan et al.; A surbey of Botulinum neurotoxin substrate expression in cells; *Mov Disord*, 10(3):376:1995.

Durham PL, Cady Ryan, Cady Roger. Regulation of calcitonin gene-related peptide secretion from trigemial nerve cells by botulinum toxin type A: implication for migraine therapy. Headache 2002;44:35-42.

Elashoff JD. nQuery Advisor Version 4.0 User's Guide, Los Angeles, 2000.

Eross, Neurology, May 27, 2003, 60(10), E8-9.

European Agency for the Evaluation of Medicinal Products. Note for guidance on clinical investigation of medicinal products for the treatment of migraine. Dec. 2003.

Foster L, Clapp L, Erickson M, Jabbari B. Botulinum toxin A and chronic low back pain. A randomized, double-blind study. Neurol 2001;56:1290-1293.

Freund BJ, Schwartz M. Use of botulinum toxin in chronic whiplash-associated disorder. Clin J Pain 2002;18(6 Suppl):S163-S168.

Fung L. K. et al., *Pharmacokinetics of Interstitial Delivery of Sarmustine 4-Hydroperoxycyclophosphamide and Paclitaxel From a Biodegradable Polymer Implant in the Monkey Brain*Cancer Research 58;672-684:1998.

Gladstone JP., Gawel M. *Newer formulation of the triptans: advances in migraine management*, Drugs. 2003;63(21):2285-305.

Gladstone, J., et al., *Chronic Daily Headache: A Rational Approach to a Challenging Problem*, Seminars in Neurology, 2003, vol. 23, No. 3, pp. 265-275.

Gonelle-Gispert et al.; snap-25a and 25b isoforms are both expressed in insulin-secreting cells and can function in insulin secretion;*Biochem J 1*, 339 (pt 1):159-65:1999.

Guyton A.C. et al., *Textbook of Medical Physiology*, W.B. Saunders Company 1996, ninth edition; 686-688.

Habermann E., et al., *Tetanus Toxin and Botulinum A and C Neurotoxins Inhibit Noradrenaline Release From Cultured Mouse Brain*, J Neurochem 51(2);522-527:1988.

Habermann E., *Inhibition by Tetanus and Botulinum A Toxin of the release of [$^3$H]Noradrenaline and [$^3$H]GABA From Rat Brain Homogenate*, Experientia 44;224-226:1988.

Habermann, I-Labeled Neurotoxin from Clostridium Botulinum A: Preparation, Binding to Synaptosomes and Ascent to the Spinal Cord: *Nauyn-Schmiedeberg's Arch. Pharmacol*. 1974; 281, 47-56.

*Harrison's Principles of Internal Medicine* (1998), edited by Anthony Fauci et al., 14$^{th}$ edition, published by McGraw Hill.

Headache Classification Committee of the International Headache Society. Classification and diagnostic criteria for headache disorders, cranial neuralgias and facial pain. Cephalalgia 1988;8 Suppl 7:1-96.

Headache Classification Subcommittee of the International Headache Society. The international classification of headache disorders, 2$^{nd}$ ed. Cephalalgia 2004;24 Suppl 1:1-151.

Heckmann M., et al., *Botulinum toxin type A injection in the treatment of lichen simplex: An open pilot study*, J Am Acad Dermatol Apr. 2002;46(4):617-9.

Hering R, Gardiner I, Catarci T, Witmarch T, Steiner T, de Belleroche J. Cellular adaptation in migraineurs with chronic daily headache. Cephalalgia 1993;13:261-6.

Holroyd KA, Stensland M, Lipchik GL, et al. Psyshosocial correlates and impact of chronic tension-type headaches. Headache 2000; 40:3-16.

International Headache Society committee on Clinical Trials in Migraine. Guidelines for controlled trials of drugs in migraine. First edition. Cephalalgia 1991;11:1-12.

Jacks, L., et al., *Idipathic toe walking: Treatment with botulinum toxin A injection*, Dev Med Child Neurol 2002;44(Suppl 91):6).

Jahanshahi M., et al., *Psychological functioning before and after treatment of torticollis with botulinum toxin*, J Neurol Neurosurg Psychiatry 1992; 55(3): 229-231.

Jankovic J. et al., *Therapy With Botulinum Toxin*, Marcel Dekker, Inc., (1994), pp. 5, 150.

Jost W., *Ten year's experience with botulinum toxin in anal fissure*, Int J Colorectal Dis Sep. 2002;17(5):298-302.

Katsambas A., et al., *Cutaneous diseases of the foot: Unapproved treatments*, Clin Dermatol Nov.-Dec. 2002;20(6):689-699.

Katsarava, et al., Neurology, May 27, 2003, vol. 60, No. 10, pp. 1682-1683.

Klapper JA, Mathew NT, Klapper A et al. Betulinum toxin type A (BTX-A) for the prophylaxis of chronic daily headache. Cephalalgia 2000;20:292-293.

Li Y, et al., *Sensory and motor denervation influences epidermal thickness in rat foot glabrous skin*, Exp Neurol 1997;147;452-462 (see p. 459).

Linde M, Limmroth V, Dahlöf C, on behalf of the Headache Masters Programme. Ethical aspects of placebo in migraine research. Cephalalgia 2003;23:491-495.

Linton-Dahlöf, M Linde, Dahlöf C. Withdrawl therapy improves chronic daily headache associated with long-term misuse of headache medication: a retrospective study Cephalalgia 2000;20:658-662.

Lipton RB, Bigal ME. Chronic daily headache: is analgesic overuse a cause or a consequence? Nurology 2003;61:154-155.

Lipton RB, Stewart WF. Migraine headaches: epidemiology and comorbidity. Clin Neuroscience 1998;5:2-9.

Loder, E., et al., *Use of Botulinum Toxins for Chronic Headaches: A Focused Review*, The Clinical Journal of Pain, 2002, 18, pp. S169-S176.

Maizels, M., et al., *The Patient with Daily Headaches*, American Family Physician, Dec. 2004, vol. 70, No. 12, pp. 2299-2306.

Manzoni GC, Granella F, Sandrini G, et al. Classification of chronic daily headache by International Headache Society criteria: limits and new proposals. Cephalalgia 1995;15:37-43.

Marjama-Lyons, J., et al., *Tremor-Predominant Parkinson's Disease*, Drugs & Aging 16(4);273-278:2000.

Mathew, et al., Headache 2002, 42:454, Abstract S107.

Mathew, N., Kailasam, J., "Disease Modification" Migraine with Botulinum Toxin Type A : Long Term Experience, 2002, 42(5):454, Abstract S107.

Mathew, N., Kailasam, J., "Disease Modification" Migraine with Botulinum Toxin Type A : Long Term Experience, 2002, Cephalalgia, 22(7):609, Abstract.

Mathew, N., Kaup, A., The Use of Botulinum Toxin Type A in Headache Treatment, 2002, 365-373.

Mathew N, Kaup A, Kailasam J. Botulinum toxin type A modifies chronic migraine further long-term (3years) experience with up to ten sets of treatments. Headache 2003;43:576.

Mathew NT, Reuveni U, Perez F. Transformed or evolutive migraine Headache 1987;27:102-106.

Mauskop A. Botulinum toxin in the treatment of chronic daily headaches. Cephalalgia 1999;19:453.

Monzon MJ, Lainez MJA. Quality of life in migraine and chronic daily headache patients. Cephalalgia 1998;18:638-643.

Moyer E et al., *Botulinum Toxin Type B: Experimental and Clinical Experience*, being chapter 6, pp. 71-85 of "Therapy With Botulinum Toxin", edited by Jankovic, J. et al. (1994), Marcel Dekker, Inc.

Murry T., et al., *Spasmodic dysphonia; emotional status and botulinum toxin treatment*, Arch Otolarynogol Mar. 1994; 120(3): 310-316.

Naumann et al; Botulinum toxin type A in the treatment of focal, axillary and palmar hyperhidrosis and other typerhidrotic conditions; *European J. Neurology* 6 (Supp 4): S111-S115:1999.

O'Brien PC, Fleming TR. A multipe testing procedure for clinical trials. Biometrics 1979;35:549-556.

(56) References Cited

OTHER PUBLICATIONS

Ondo WG, Vuong KD, Derman HS. Botulinum toxin A for chronic daily headache: a reandomized, placebo-controlled, parallel design study. Cephalalgia 2004;24:60-5.
Payne M., et al, *Botulinum toxin as a novel treatment for self mutilation in Lesch-Nyhan syndrome*, Ann Neurol Sep. 2002;52(3 Supp 1):S157.
Pearce, L.B., *Pharmacologic Characterization of Botulinum Toxin For Basic Science and Medicine*, Toxicon 35(9);1373-1412 at 1393.
Purkiss J, Welch M, Doward S, et al. Capsaicin-stimulated release of substance P from cultured dorsal root ganglion neurons: involvement of two distinct mechanisms. Biochem Pharmacol 2000;59:1403-1406.
Rabasseda et al., Toxicon, 26:329-326, 1988.
Ragona et al.; Management of Parotid Sialocele With Botulinum Toxin; *The Laryngoscope* 109:1344-1346:1999.
Rahimtoola H, Buurma H, Tijssen CC, et al. Migraine prophylactic medication usage patterns in The Netherlands. Cephalalgia 2003;23:293-301.
Relja G, Granato A, Maria Antonello R, Zorzon M. *Headache induced by chronic substance use: analysis of medication overused and minimum dose required to induce headache*, Headache. Feb. 2004;44(2):148-53.
Rogers J., et al., *Injections of botulinum toxin A in foot dystonia*, Neurology Apr. 1993;43(4 Suppl 2).
Sanchez-Prieto, J., et al., *Botulinum Toxin A Blocks Glutamate Exocytosis From Guinea Pig Cerebral Cortical Synaptosomes*, Eur J. Biochem 165;675-681:1987.
Saper JR, Lake AE III, Cantrell DT, et al. Chronic daily headache prophylaxis with tizanidine: a double-blind, placebo-controlled, multicenter outcome study. Headache 2002;42:470-482.
Schantz, E.J., et al, *Properties and use of Botulinum toxin and Other Microbial Neurotoxins in Medicine*, Microbiol Rev. 56;80-99:1992.
Scher AI, Stewart WF, Liberman J, et al. Prevalence of frequent headache in a population sample. Headache 1998;38:497-506.
Schim, J, et al., *Effect of Preventive Treatment with Botulinum Toxin Type A on Acute Headache Medication Usage in Migraine Patients*, Current Medical Research Opinions, vol. 20, No. 1, 2004, pp. 49-53.
Schwartz BS, Stewart WF, Lipton RB. Loss of workdays and decreased work effectiveness associated with headache in the workplace. J Occup Environ Med 1997;39:320-327.
Sevim, S., et al., *Botulinum toxin—A therapy for palmar and plantar hyperhidrosis*, Acta Neurol Belg Dec. 2002;102(4):167-70.
Siegel S. Non-parametric statistics for the behavioral sciences. New York: McGraw-Hill Book Company, 1956;96:116-127.
Siberstein SD, Lipton RB, Sliwinski M. Classification of daily and near-daily headaches: field trial of revised IHS criteria. Neurology 1996;47:871-875.
Silberstein SD, Lipton RB, Solomon S, Mathew NT. Classification of daily and near-daily headaches: proposed revisions to the IHS criteria. Headache 1194;34:1-7.
Silberstein SD, Lipton RB. Chronic daily headache, including transformed migraine, chronic tension-type headache, and medication overuse. In: Silberstein SD, Lipton RB, Dalessio DJ, eds. Wolff's headache and other head pain, 7$^{th}$ ed. New York, NY: Oxford University Press;2001:247-282.

Silberstein SD, Lipton RB. Chronic daily headache. Curr Opin Neurol 2000;13:277-283.
Silberstein SD, Neto W, Schmitt J, et al. Topiramate in migraine prevention. Arch Neurol 2004;61:490-495.
Silberstein SD, Silberstein MM. New concepts in the pathogenesis of headache. Part II. Pain Man 1990;3:332-342.
Silvestrini M, Bartolini M, Coccia M, et al. Topiramate in the treatment of chronic migraine. Cephalalgia 2003;23:820-824.
Simpson et al,. Pharmacol. Rev., 33:155-188, 1981.
Singh, *Critical Aspects of Bacterial Protein Toxins*, pp. 63-84 (chapter 4) of Natural Toxins II, edited by B.R. Singh et al., Plenum Press, New York (1996).
Sloop RR, Cole BA, Escutin RO. Reconstituted botulinum toxin type A does not lose potency in humans if it is refrozen or refrigerated for 2 weeks before use. Neurology. Jan. 1997;48(1):2449-53.
Smuts JA, Baker MK, Smuts HM, et al. Prophylactic treatment of chronic tension-type headache using botulinum toxin type A, Eur J Neurol 1999;6(Suppl 4):S99-S102.
Solomon GD, Sokbieranda FG, Genzen JR. Quality of life assessment among migraine patients treated with Sumatriptan. Headache 1995;35:449-454.
Spira PJ, Beran RG. Gabapentin in the prophylaxis of chronic daily headache: a randomized, placebo-controlled study. Neurology 2003;61:1753-1759.
Stewart WR, Lipton RB, Celentano DD, et al. Prevalence of migraine headaches in the United States. Relation to age, income, race and other sociodemographis factors, JAMA 1992;267:64-69.
Suputtitada, A., *Local botulinum toxin type A injections in the treatment of spastic toes*, Am J Phys Med Rehabil Oct. 2002;81(10):770-5.
Tepper and Dodick, Debate: Analgesic overuse is a cause, not a consequence, of chronic daily headache, *Headache*, 2002; 42:543-554.
Tepper, S., et al., *Botulinum Toxin Type A in the Preventive Treatment of Refractory Headaches—Comparison Between Medication Overusers and Nonmedication Overusers Groups*, Cephalalgia, 2003, 23, p. 715, poster P5N86.
Troost BT. Botulinum toxin type A (Botox) in the treatment of migraine and other headaches. Expert Rev Neurotherap 2004;4:27-31.
Wang SJ, Fuh JL, Lu SR, et al. Chronic daily headache in Chinese elderly: prevalence, risk factors and biannual follow-up. Neurology 2000;54:314-319.
Wang SJ, Fuh JL, Lu SR, et al. Quality of life differs among headache diagnoses: analysis of SF-36 survey in 901 headache patients. Pain 2001;89:285-292.
Weigand et al.; I-Labelled Botulinum A Neurotoxin: Pharmacokinetics in Cats after Intramuscular Injection; *Naunyn-Schmiedeberg's Arch. Pharmacol*. 1976; 292, 161-165.
Welch KM, Goadsby PJ. Chronic daily headache: nosology and pathophysiology. Curr Opin Neurol 2002;15:287-95. Review.
Wissel J, Muller J, Dressnandt J, Heinen F, Naumann M, Topka H, Poewe W. Management of spasticity associated pain with botulinum toxin A. J Pain Symptom Manage 2000;20:44-9.
Woolf C. et al., *Neuropathic Pain: Aetiology, Symptoms, Mechanisms, and Management*, Lancet 1999; 353: 1959-64.

\* cited by examiner

Illustration of the Face and Sites to Inject for Treatments 1, 2, 3 and 4.

METHODS FOR TREATING HEADACHE

CROSS REFERENCE

This application is a continuation of U.S. patent application Ser. No. 14/797,552, filed Jul. 13, 2015, now U.S. Pat. No. 9,555,085, which is a continuation of U.S. patent application Ser. No. 12/256,655, filed Oct. 23, 2008, now U.S. Pat. No. 9,078,893, which is a continuation of U.S. patent application Ser. No. 11/329,598, filed Jan. 11, 2006, now U.S. Pat. No. 7,704,511, which is a continuation of U.S. patent application Ser. No. 11/319,880, filed Dec. 28, 2005, now abandoned, which is a continuation of U.S. patent application Ser. No. 11/039,506, filed Jan. 18, 2005, now abandoned, which is a continuation-in-part of U.S. patent application Ser. No. 10/789,180, filed Feb. 26, 2004, the entire content of each application is incorporated herein by reference.

BACKGROUND

The present invention relates to methods for treating pain. In particular, the present invention relates to use of a botulinum toxin to treat and prevent headaches and to treat an acute pain alleviation medication disorder. The present invention also includes improved methods for treating headaches by using a triptan and a botulinum toxin to treat a headache, and methods for increasing the effectiveness of a triptan to treat a headache, such as a migraine headache.

Many, if not most ailments of the body cause pain. Generally pain is experienced when the free nerve endings which constitute the pain receptors in the skin as well as in certain internal tissues are subjected to mechanical, thermal, chemical or other noxious stimuli. The pain receptors can transmit signals along afferent neurons into the central nervous system and thence to the brain.

The causes of pain can include inflammation, injury, disease, muscle spasm and the onset of a neuropathic event or syndrome. Ineffectively treated pain can be devastating to the person experiencing it by limiting function, reducing mobility, complicating sleep, and dramatically interfering with the quality of life.

A muscle spasm can led to stimulation of mechanosensitive pain receptors thereby causing a sensation of pain. Thus, pain can arise from or be due to a muscle spasm. Additionally, the spasm can indirectly stimulate the pain receptors by compressing onto blood vessels, causing ischemia in the tissue, which in turn releases pain inducing substances that stimulate pain receptors to cause pain sensations. Furthermore, a muscle spasm can cause a localized pH reduction which can be perceived as or which can engender pain signals. Hence, pain can be a secondary effect of a muscle spasm or muscle hypertonicity.

Inflammatory pain can occur when tissue is damaged, as can result from surgery or due to an adverse physical, chemical or thermal event or to infection by a biologic agent. When a tissue is damaged, a host of endogenous pain inducing substances, for example bradykinin and histamine can be released from the injured tissue. The pain inducing substances can bind to receptors on the sensory nerve terminals and thereby initiate afferent pain signals.

Additionally, pain inducing substances can be released from nociceptive afferent terminals, and neuropeptides released from sensory terminals can accentuate an inflammatory response. Thus, during inflammation there can be a sprouting of peptidergic peripheral fibers and an increased content of peptide, with many fibers showing a coexistence of substance P (SP) and calcitonin gene related peptide (CGRP). Substance P can induce contraction of endothelia cells, which in turn causes plasma extravasation to allow other substances (bradykinin, ATP, histamine) to gain access to the site of injury and the afferent nerve terminals. Substance P release by the sensory nerve terminal can also degranulate mast cell. This process has been considered to be an important factor in neurogenic inflammation due to the release of inflammatory mediators such as histamine and serotonin and the release of proteolytic enzymes which catalyze the production of bradykinin. CGRP apparently does not produce plasma extravasation but is a powerful vasodilator and also act synergistically with SP and other inflammatory mediators to enhance plasma extravasation. All the above listed inflammatory mediators can either sensitize nociceptors or produce pain.

After activation of the primary sensory afferent neurons the next step in the transduction of sensory signals can be activation of projection neurons, which carry the signal, via the spinothalamic tract, to higher parts of the central nervous system such as the thalamic nuclei. The cell bodies of these neurons (other than those related to the cranial nerves) are located in the dorsal horn of the spinal cord. Here also one can find the synapses between the primary afferents and the projection neurons. The dorsal horn is organized into a series of laminae that are stacked, with lamina I being most dorsal followed by lamina II, etc. The different classes of primary afferents make synapses in different laminae. For cutaneous primary afferents, C-fibers make synapses in laminae I and II, A delta-fibers in laminae I, II, and V, and A beta-fibers in laminae III, IV, and V. Deeper laminae (V-VII, X) are thought to be involved in the sensory pathways arriving from deeper tissues such as muscles and the viscera.

The predominant neurotransmitters at the synapses between primary afferent neurons and projection neurons are substance P, glutamate, CGRP and neuropeptide Y. The efficiency of transmission of these synapses can be altered via descending pathways and by local interneurons in the spinal cord. These modulatory neurons can release a number of mediators that are either inhibitory (e.g. opioid peptides, glycine) or excitatory (e.g. nitric oxide, cholecystokinin), to provide a mechanism for enhancing or reducing awareness of sensations.

Although inflammatory pain is generally reversible and subsides when the injured tissue has been repaired or the pain inducing stimulus removed, present methods for treating inflammatory pain have many drawbacks and deficiencies. Thus, the typical oral, parenteral or topical administration of an analgesic drug to treat the symptoms of pain or of, for example, an antibiotic to treat inflammatory pain causation factors can result in widespread systemic distribution of the drug and undesirable side effects. Additionally, current therapy for inflammatory pain suffers from short drug efficacy durations which necessitate frequent drug re-administration with possible resulting drug resistance, antibody development and/or drug dependence and addiction, all of which are unsatisfactory. Furthermore, frequent drug administration increases the expense of the regimen to the patient and can require the patient to remember to adhere to a dosing schedule.

Examples of treatments for inflammation and muscle pain include non-steroidal anti-inflammatory drugs (NSAIDs), including aspirin and ibuprofen; and opioids, such as morphine.

NSAIDs alleviate pain by inhibiting the production of prostaglandins released by damaged tissues. Prostaglandins have been shown to be peripheral mediators of pain and inflammation, as in arthritic diseases, and a reduction in their concentration provides relief to patients. It has been suggested that prostaglandins are involved in the mediation of pain in the spinal cord and the brain, which may explain the analgesic effects of NSAIDs in some pain states that do not involve inflammation or peripheral tissue damage. However, prostaglandins are only one of several mediators of pain. As such, NSAIDs have a ceiling of activity above which increasing doses do not give more pain relief. Furthermore, they have side effects that limit their usefulness. For example, NSAIDs can cause irritation of the gastro-intestinal tract and prolonged use may lead to the development of extensive ulceration of the gut. This is particularly true in elderly patients who frequently use NSAIDs for their arthritis conditions.

The therapeutic actions of opioids are in the spinal cord. Opioids inhibit the efficiency of neurotransmission between the primary sensory afferents (principally C-fibers) and the projection neurons. They achieve this by causing a prolonged hyperpolarization of both elements of these synapses. The use of opioids is effective in alleviating most types of acute pain and chronic malignant pain. There are, however, a number of chronic malignant pain conditions which are partly or completely refractory to opioid analgesia, particularly those which involve nerve compression, e.g. by tumor formation. Unfortunately opioids also have unwanted side-effects including: (1) depression of the respiratory system, (2) constipation, and (3) psychoactive effects including sedation and euphoria. These side effects occur at doses similar to those that produce analgesia and therefore limit the doses that can be given to patients. Additionally, opioids such as morphine and heroin are well-known drugs of abuse that lead to physical dependence, which also involves the development of tolerance. With the development of tolerance, the dose of a drug required to produce the same analgesic effect increases with time. This may lead to a condition in which the doses required to alleviate the pain are life-threatening due to previously mentioned side-effects.

Although pain arising from inflammation and muscle spasm can be initiated by mechanical or chemical stimulation of the primary sensory neuron free terminal, neuropathic pain does not require an initial stimulus to the peripheral, free nerve terminal. Neuropathic pain is a persistent or chronic pain syndrome that can result from damage to the nervous system, the peripheral nerves, the dorsal root ganglion, dorsal root, or to the central nervous system.

Neuropathic pain syndromes include allodynia, various neuralgias such as post herpetic neuralgia and trigeminal neuralgia, phantom pain, and complex regional pain syndromes, such as reflex sympathetic dystrophy and causalgia. Causalgia is often characterized by spontaneous burning pain combined with hyperalgesia and allodynia.

Unfortunately, there is no existing method for adequately, predictably and specifically treating established neuropathic pain (Woolf C. et al., *Neuropathic Pain: Aetiology, Symptoms, Mechanisms, and Management*, Lancet 1999; 353: 1959-64) as present treatment methods for neuropathic pain consists of merely trying to help the patient cope through psychological or occupational therapy, rather than by reducing or eliminating the pain experienced.

For example, current methods to treat neuropathic pain include administration of local anesthetic blocks targeted to trigger points, peripheral nerves, plexi, dorsal roots, and to the sympathetic nervous system. However, these treatments have only short-lived antinociceptive effects. Additionally, longer lasting analgesic treatment methods, such as blocks by phenol injection or cryotherapy raise a considerable risk of irreversible functional impairment. Furthermore, chronic epidural or intrathecal (collectively "intraspinal") administration of drugs such as clonidine, steroids, opioids or midazolam have significant side effects and questionable efficacy.

Headache

A headache is a pain in the head, such as in the scalp, face, forehead or neck. A headache can be a primary headache or a secondary headache. A primary headache is a headache which is not caused by another condition. Contrarily, a secondary headache is due to a disease or medical condition, such as an illness, infection, injury, stroke or other abnormality. Thus, with a secondary headache there is an underlying disorder that produces the headache as a symptom of that underlying disorder. Tension headache is the most common type of primary headache and tension headaches account for about 90% of all headaches. A tension headache is often experienced in the forehead, in the back of the head and neck, or in both regions. It has been described as a tight feeling, as if the head were in a vise. Soreness in the shoulders or neck is common. Nausea is uncommon with a tension headache.

Migraine headaches are recurrent headaches that may be unilateral or bilateral. Migraine headaches may occur with or without a prodrome. The aura of a migraine may consist of neurologic symptoms, such as dizziness, tinnitus, scotomas, photophobia, or visual scintillations (eg, bright zigzag lines). Migraines without aura are the most common, accounting for more than 80% of all migraines.

An estimated 10-20% of the population suffers from migraine headaches. An estimated 6% of men and 15-17% of women in the United States have migraine. Migraines most commonly are found in women, with a 3:1 female-to-male ratio.

About 2% of all headaches are secondary headaches. For example, a cervicogenic headache is a headache which is due to a neck problem, such as an abnormality of neck muscles, which can result from prolonged poor posture, arthritis, injuries of the upper spine, or from a cervical spine disorder. Sinus headache is another type of secondary headache. A sinus headache can be caused by inflammation and/or infection in the paranasal sinuses.

Medication Overuse Headache Disorder

Daily or near-daily headache can affect up to 5% of some populations, and it is believed that chronic overuse of headache drugs may account for half of this phenomenon. All simple analgesics, and probably non-steroidal anti-inflammatory drugs, ergotamine, and triptans, are implicated. Triptans are a family of tryptamine drugs used in the treatment of headache. Triptans act by binding to serotonin $5\text{-HT}_{1B}$ and $5\text{-HT}_{1D}$ receptors in cranial blood vessels (causing their constriction) and subsequent inhibition of pro-inflammatory neuropeptide release. Thus, triptans are 5HT (1B/1D) receptor agonists and are commonly prescribed for migraine headache treatment. Sumatriptan (Imitrex®, Imigran®), zolmitriptan (Zomig®), naratriptan (Amerge®, Naramig®), rizatriptan (Maxalt®), almotriptan (Axert®), frovatriptan (Frova®), and eletriptan (Relpax®) are triptan drugs.

Medication overuse headache affects more women than men (on a ratio of 5:1) and some children. The regular intake of three or more analgesic tablets daily or narcotics or ergotamine on more than two days a week to control or alleviate a headache has been suggested as a medication overuse headache definition. A common and probably key factor in medication overuse headache is pre-emptive use of drugs, in anticipation of rather than for a headache. Medication overuse headache usually does not develop when analgesics are regularly taken for another indication, such as chronic backache or rheumatic disease, that is the headache must be present to begin with.

A presumptive diagnosis of medication overuse headache is based on symptoms and a detailed history of drug use, including over the counter drugs. Many patients with medication overuse headache disorder use large quantities of drug: 35 doses a week on average in one study, and six different agents. Sooner or later, such patients seek prescriptions for "something stronger," bringing them to the general practitioner's attention. However, medication overuse headache is typically confirmed only when symptoms improve after drugs are withdrawn. The headache is oppressive, present, and often at its worst on awakening in the morning. It can be increased after physical exertion. Associated nausea and vomiting are rarely pronounced. A typical history begins with episodic headache up to years earlier (more commonly migraine than tension-type headache), treated with an analgesic or other acute medication. Over time, headache episodes become more frequent, as does drug intake, until both are daily. In the end stage, which not all patients reach, headache persists all day, fluctuating with medication use repeated every few hours. This evolution occurs over a few weeks or much longer, depending largely but not solely on the medication taken.

The International Headache Society defines medication overuse headache (MOH) as a chronic headache (headache frequency >15 days per month) after the intake of analgesics or ergots (more than 15 times per month for at least 3 months), which disappears after withdrawal therapy. It has been described as a self-sustaining, rhythmic, headache medication cycle characterized by daily or near daily headache and irresistible and predictable use of immediate relief medications. Evidence supporting the existence of MOH is widely published in the medical literature.

The pathogenesis of MOH has not been fully elucidated. Some evidence suggests that up regulation of serotonin receptors and subsequent reduction in serotonin levels, which normalize upon cessation of chronic analgesic use, may play a role. The following have also been implicated in the development of MOH: endorphin suppression, central opioid receptor impairment, impaired suppression or downregulation of an already partly suppressed or abnormal antinociceptive system, alterations in density and function of postsynaptic neuronal receptors, and activation of nociceptive "on-cells" in the ventral medulla that facilitate nociceptive reflex responses. A common presentation is a patient with a history of episodic migraine with or without aura, who complains of increased headache frequency and the development of interparoxysmal tension-type headache, that eventually transforms into a daily or near-daily headache lasting for prolonged periods. Patients may alternate between migraine-type and tension-type headaches during this period. Behavioral and psychiatric comorbidities may also be present and are complicating factors. It is common for patients to underestimate their use of analgesics and to use multiple types of agents concomitantly. Initially, pain relief provides negative reinforcement, and in some cases changes in mood incurred from barbiturate and caffeine-containing analgesics, may provide positive reinforcement, resulting in excessive use. Tolerance, characterized by increasing consumption without regard to potential adverse outcomes, and withdrawal symptoms upon abrupt discontinuation, often ensue and result in increased headache frequency and severity with a decrease in analgesic efficacy. Concomitant preventive medications are relatively ineffective, while the patient is using excessive amounts of abortive agents and complete discontinuation of headache medication is the treatment of choice. Detoxification is usually conducted slowly over as many as 8 to 12 weeks and in the most severe cases, may warrant hospitalization.

Medication overuse to treat headache ("MOH") has been recently recognized as a unique disorder diagnosis of the International Classification of Headache Disorders, $2^{nd}$ edition, published in supplement 1, Cephalalgia 2004: volume 24, pages 94-95, wherein, significantly, it is stated that patients with a MOH disorder rarely respond to other preventive medications while they are overusing their acute pain medications.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein* Toxins, pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

[1] Available from Allergan, Inc., of Irvine, Calif. under the tradename BOTOX® in 100 unit vials Seven generally immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type B: Experimental and Clinical Expe-*

*rience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989 a botulinum toxin type A complex has been approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem J* 1; 339 (pt 1):159-65:1999, and *Mov Disord*, 10(3):376: 1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemagglutinin protein and a non-toxin and non-toxic nonhemagglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [$^3$H]Noradrenaline and [$^3$H]GABA From Rat Brain Homogenate*, Experientia 44; 224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56; 80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1\text{-}2 \times 10^8$ $LD_{50}$ U/mg or greater; purified botulinum toxin type B with an approximately 156 kD molecular weight with a specific potency of $1\text{-}2 \times 10^8$ $LD_{50}$ U/mg or greater, and; purified botulinum toxin type F with an approximately 155 kD molecular weight with a specific potency of $1\text{-}2 \times 10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can be stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N—Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249-53:1997.

It has been reported that botulinum toxin type A has been used in clinical settings as follows:
(1) about 75-125 units of BOTOX® per intramuscular injection (multiple muscles) to treat cervical dystonia;
(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intersphincteric injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimis: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Jyons, J., et al., *Tremor-Predominant Parkinson's Disease*, Drugs & Aging 16(4); 273-278: 2000.

It is known that botulinum toxin type A can have an efficacy for up to 12 months (*European J. Neurology* 6 (Suppl 4): S111-S1150:1999), and in some circumstances for as long as 27 months, when used to treat glands, such as in the treatment of hyperhidrosis. See e.g. Bushara K., *Botulinum toxin and rhinorrhea*, Otolaryngol Head Neck Surg 1996; 114(3):507, and *The Laryngoscope* 109:1344-1346:1999. However, the usual duration of an intramuscular injection of Botox® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and Dysport® available from Beaufour Ipsen, Porton Down, England. A Botulinum toxin type B preparation (MyoBloc®) is available from Elan Pharmaceuticals of San Francisco, Calif.

In addition to having pharmacologic actions at the peripheral location, botulinum toxins may also have inhibitory effects in the central nervous system. Work by Weigand et al, *Naunyn-Schmiedeberg's Arch. Pharmacol.* 1976; 292, 161-165, and Habermann, *Naunyn-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

It has been reported that use of a botulinum toxin to treat various spasmodic muscle conditions can result in reduced depression and anxiety, as the muscle spasm is reduced. Murry T., et al., *Spasmodic dysphonia; emotional status and botulinum toxin treatment*, Arch Otolaryngol 1994 March; 120(3): 310-316; Jahanshahi M., et al., *Psychological functioning before and after treatment of torticollis with botulinum toxin*, J Neurol Neurosurg Psychiatry 1992; 55(3): 229-231. Additionally, German patent application DE 101 50 415 A1 discusses intramuscular injection of a botulinum toxin to treat depression and related affective disorders.

A botulinum toxin has also been proposed for or has been used to treat skin wounds (U.S. Pat. No. 6,447,787), various autonomic nerve dysfunctions (U.S. Pat. No. 5,766,605), tension headache, (U.S. Pat. No. 6,458,365), migraine headache pain (U.S. Pat. No. 5,714,468), sinus headache (U.S. patent application Ser. No. 429,069), post-operative pain and visceral pain (U.S. Pat. No. 6,464,986), neuralgia pain (U.S. patent application Ser. No. 630,587), hair growth and hair retention (U.S. Pat. No. 6,299,893), dental related ailments (U.S. provisional patent application Ser. No. 60/418,789), fibromyalgia (U.S. Pat. No. 6,623,742), various skin disorders (U.S. patent application Ser. No. 10/731,973), motion sickness (U.S. patent application Ser. No. 752,869), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), down turned mouth corners (U.S. Pat. No. 6,358,917), nerve entrapment syndromes (U.S. patent application 2003 0224019), various impulse disorders (U.S. patent application Ser. No. 423,380), acne (WO 03/011333) and neurogenic inflammation (U.S. Pat. No. 6,063,768). Controlled release toxin implants are known (see e.g. U.S. Pat. Nos. 6,306,423 and 6,312,708) as is transdermal botulinum toxin administration (U.S. patent application Ser. No. 10/194,805).

Botulinum toxin type A has been used to treat epilepsia partialis continua, a type of focal motor epilepsy. Bhattacharya K., et al., *Novel uses of botulinum toxin type A: two case reports*, Mov Disord 2000; 15(Suppl 2):51-52.

It is known that a botulinum toxin can be used to: weaken the chewing or biting muscle of the mouth so that self inflicted wounds and resulting ulcers can heal (Payne M., et al, *Botulinum toxin as a novel treatment for self mutilation in Lesch-Nyhan syndrome*, Ann Neurol 2002 September; 52(3 Supp 1):5157); permit healing of benign cystic lesions or tumors (Blugerman G., et al., *Multiple eccrine hidrocystomas: A new therapeutic option with botulinum toxin*, Dermatol Surg 2003 May; 29(5):557-9); treat anal fissure (Jost W., *Ten years' experience with botulinum toxin in anal fissure*, Int J Colorectal Dis 2002 September; 17(5):298-302, and; treat certain types of atopic dermatitis (Heckmann M., et al., *Botulinum toxin type A injection in the treatment of lichen simplex: An open pilot study*, J Am Acad Dermatol 2002 April; 46(4):617-9).

Additionally, a botulinum toxin may have an effect to reduce induced inflammatory pain in a rat formalin model. Aoki K., et al, *Mechanisms of the antinociceptive effect of subcutaneous Botox: Inhibition of peripheral and central nociceptive processing*, Cephalalgia 2003 September; 23(7): 649. Furthermore, it has been reported that botulinum toxin nerve blockage can cause a reduction of epidermal thickness. Li Y, et al., *Sensory and motor denervation influences epidermal thickness in rat foot glabrous skin*, Exp Neurol 1997; 147:452-462 (see page 459). Finally, it is known to administer a botulinum toxin to the foot to treat excessive foot sweating (Katsambas A., et al., *Cutaneous diseases of the foot: Unapproved treatments*, Clin Dermatol 2002 November-December; 20(6):689-699, Sevim, S., et al., *Botulinum toxin-A therapy for palmar and plantar hyperhidrosis*, Acta Neurol Belg 2002 December; 102(4):167-70), spastic toes (Suputtitada, A., *Local botulinum toxin type A injections in the treatment of spastic toes*, Am J Phys Med Rehabil 2002 October; 81(10):770-5), idiopathic toe walking (Tacks, L., et al., *Idiopathic toe walking: Treatment with botulinum toxin A injection*, Dev Med Child Neurol 2002; 44(Suppl 91):6), and foot dystonia (Rogers J., et al., *Injections of botulinum toxin A in foot dystonia*, Neurology 1993 April; 43(4 Suppl 2)).

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for ganglioside receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9158:1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is an effective method for preventing headaches and for treating medication overuse disorders. What is also needed is a method for increasing the effectiveness of a triptan to treat a headache, as such a method could permit lower dosages of a triptan to be used.

SUMMARY

The present invention meets this need and provides methods for effectively preventing headaches, treating pain and for treating medication overuse disorders (MOD), by local administration of a Clostridial toxin. Our invention also provides a method for increasing the effectiveness of a triptan to treat a headache.

A method according to our invention can be carried out by administration of a Clostridial toxin to a patient with a MOD. The Clostridial toxin used is preferably a botulinum toxin (as either a complex or as a pure [i.e. about 150 kDa molecule], such as a botulinum toxin A, B, C, D, E, F or G. Administration of the Clostridial toxin can be by a transdermal route (i.e. by application of a Clostridial toxin in a cream, patch or lotion vehicle), subdermal route (i.e. subcutaneous or intramuscular), or intradermal route of administration.

A hypothesized physiological reason for the efficacy of our invention, as explained in greater detail below, is to reduce, inhibit or eliminate sensory input (afferent) from the periphery into the central nervous system (including to the brain) which is perceived by the patient as pain and/or which engenders development of a medication overuse disorder. Such pain sensory input can be attenuated or eliminated by targeting subdermal sensory neurons with a low dose of a Clostridial toxin.

The dose of a Clostridial toxin used according to the present invention is less than the amount of Clostridial toxin (such as a botulinum toxin) that would be used to paralyze a muscle, since an intent of a method according to the present invention is not to paralyze a muscle but to reduce a pain sensory output from sensory neurons located in or on a muscle, or in or under the skin.

The following definitions apply herein:

"About" means approximately or nearly and in the context of a numerical value or range set forth herein means±10% of the numerical value or range recited or claimed.

"Alleviating" means a reduction in the occurrence of a pain, of a headache or of a symptom of a MOD. Thus, alleviating includes some reduction, significant reduction, near total reduction, and total reduction. An alleviating effect may not appear clinically for between 1 to 7 days after administration of a Clostridial toxin to a patient.

"Botulinum toxin" means a botulinum neurotoxin as either pure toxin or complex, and excludes botulinum toxins which are not neurotoxins such as the cytotoxic botulinum toxins $C_2$ and $C_3$.

"Local administration" means administration (i.e. by a subcutaneous, intramuscular, subdermal or transdermal route) of a pharmaceutical agent to or to the vicinity of a muscle or of a subdermal location or in the head of a patient by a non-systemic route. Thus, local administration excludes systemic (i.e. to the blood circulation system) routes of administration, such as intravenous or oral administration. Peripheral administration means administration to the periphery (i.e. to a location on or within a limb, trunk or head of a patient) as opposed to a visceral or gut (i.e. to the viscera) administration.

"Treating" means to alleviate (or to eliminate) at least one symptom of pain (such as a headache pain) or of a MOD, either temporarily or permanently.

The Clostridial neurotoxin is administered in a therapeutically effective amount to alleviate pain, to prevent a headache or to treat a symptom of a MOD. A suitable Clostridial neurotoxin may be a neurotoxin made by a bacterium, for example, the neurotoxin may be made from a *Clostridium botulinum, Clostridium butyricum*, or *Clostridium baratii*. In certain embodiments of the invention, the disorder can be treated by intramuscular (facial) administration a botulinum toxin to the patient. The botulinum toxin may be a botulinum toxin type A, type B, type $C_1$, type D, type E, type F, or type G. The pain and/or MOD alleviating effects of the botulinum toxin may persist for between about 1 month and 5 years. The botulinum neurotoxin can be a recombinantly made botulinum neurotoxins, such as botulinum toxins produced by *E. coli*. In addition or alternatively, the botulinum neurotoxin can be a modified neurotoxin, that is a botulinum neurotoxin which has at least one of its amino acids deleted, modified or replaced, as compared to a native or the modified botulinum neurotoxin can be a recombinant produced botulinum neurotoxin or a derivative or fragment thereof.

A method for treating a MOD according to the present invention can comprise the step of local administration of a botulinum toxin to a patient with a MOD to thereby alleviate the MOD. The botulinum toxin can be selected from the group consisting of botulinum toxin types A, B, C, D, E, F and G. Botulinum toxin type A is a preferred botulinum toxin. The botulinum toxin can be administered in an amount of between about 1 unit and about 3,000 units and the alleviation of the MOD can persist for between about 1 month and about 5 years. The local administration of the botulinum toxin can be to or to a vicinity of where the patient experiences or is predisposed to experience pain. Alternately, the local administration can be by intramuscular injection or to a subdermal location from which the patient perceives the existence of a pain to arise, typically at the forehead.

Another embodiment of our invention is a method for treating a headache in a triptan medication overuse patient. The method can comprise the step of local administration of a botulinum toxin to a patient who is a triptan medication overuse patient, thereby both countering a headache exacerbation caused by triptan medication overuse and reducing the use of triptan medication by the patient to treat a headache.

A further embodiment of our invention is a method for increasing the effectiveness of a triptan medication to treat a headache. The method can comprise the step of administering a triptan to treat a headache and local administration of a botulinum toxin.

DRAWINGS

The following drawings are presented to assist understanding of aspects and features of the present invention.

FIG. 1 is a graph which shows results (mean change in the number of headaches per thirty day period) of a clinical study carried out for use of BOTOX to inter alia treat migraine headache, showing that the patients had fewer headaches after administration of BOTOX. In all the data shown in all the Figures the patients had been administered BOTOX at days 0, 90 and 180.

FIG. 2 is a graph which shows results (mean change in the number of days when the patients were concurrently taking acute headache pain alleviation medication per thirty day period) of a clinical study carried out for use of BOTOX to inter alia treat migraine headache, showing that the patients had fewer days when they were taking acute headache pain alleviation medication after administration of BOTOX.

FIG. 3 shows a decrease in narcotics use in the BOTOX treated patients.

Figure 6:
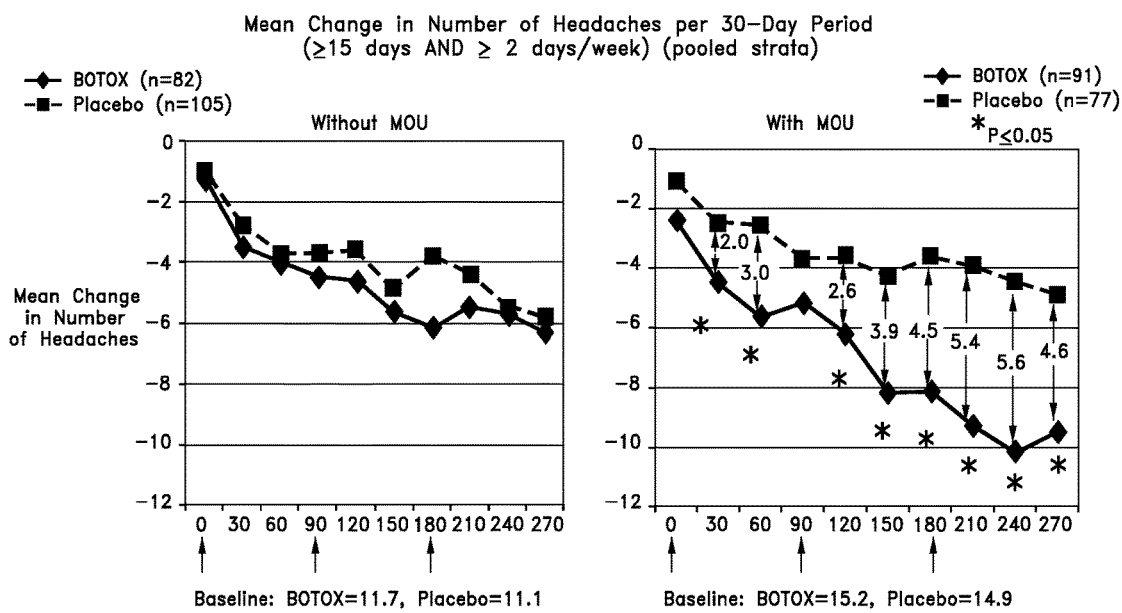

FIG. 6 comprises two graphs which shows the mean change in the number of headaches experienced by patients over a thirty day period after administration of BOTOX, where the patients either did not have a medication overuse disorder ("without MOU") (left hand side graph) or the patients did have a medication overuse disorder (right hand side graph). "≥15 days and ≥2 days/week" are criteria used to determine that a patient had a medication overuse ("MOU") disorder. MOU and MOD are synonymous terms. By definition a patient has a MOU disorder if he or she takes an acute medication 15 or more days per month and at least twice a week in the week that they are experiencing the acute pain.

Figure 7:
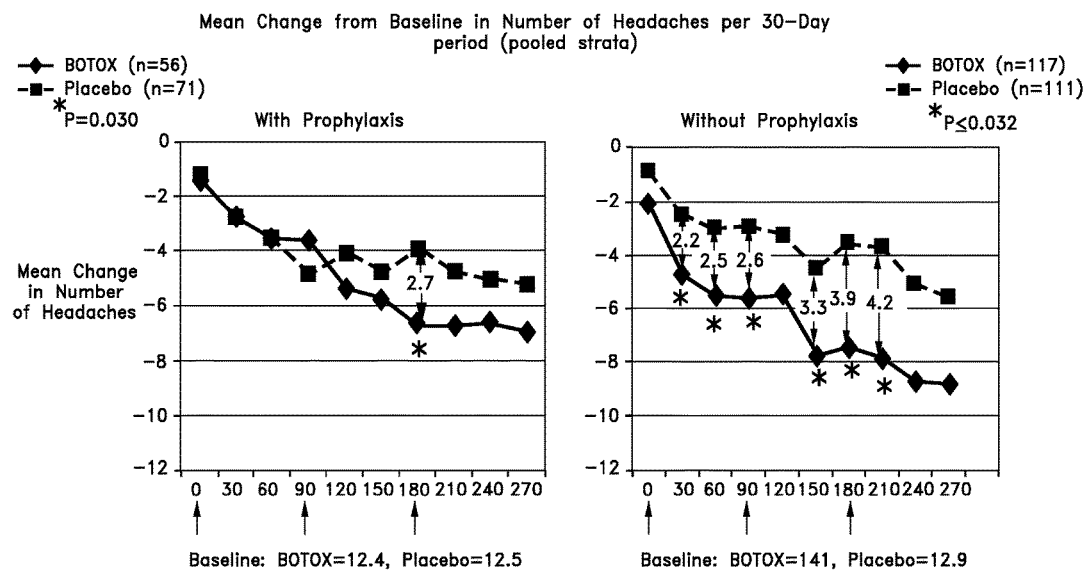

FIG. 7 comprises two graphs which show the mean change from baseline in the frequency of headaches per 30-day period in patients using (graph A) and not using (graph B) prophylactic headache medications at baseline, for a pooled population of patients. The Y-axis represents the mean change in the number of headaches per thirty day period. "n" means the number of patients in the sample of patients evaluated.

Figure 8:
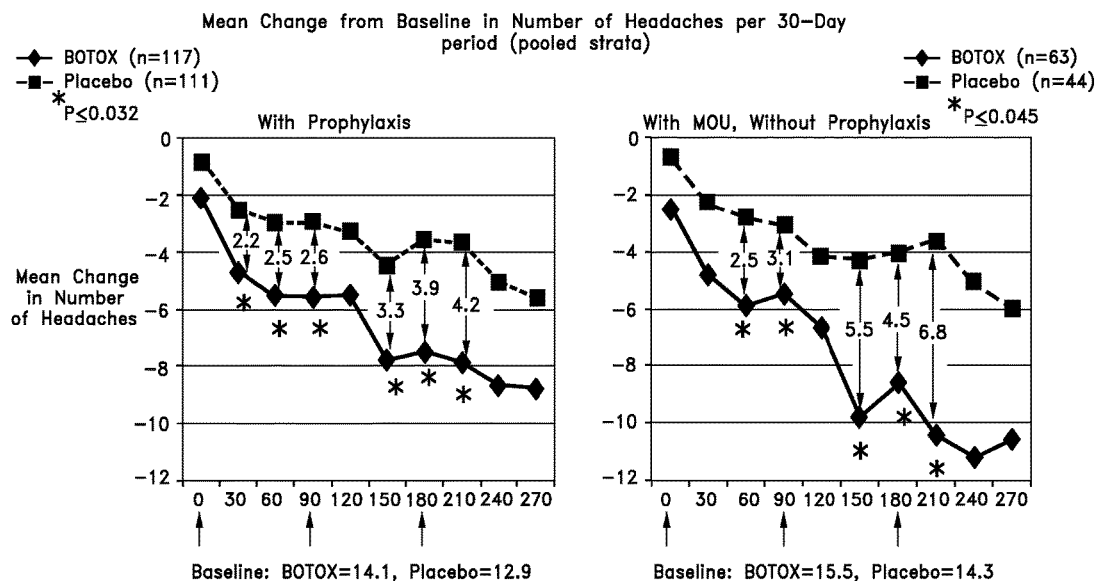

FIG. 8 comprises two graphs which shows the mean change in the number of headaches experienced by patients over a thirty day period after administration of BOTOX, where the patients either were not concurrently using another headache prophylaxis treatment (left hand side graph) or the patients were not concurrently using another headache prophylaxis treatment and did have a medication overuse disorder (right hand side graph). The prophylaxis is used by the patient to prevent the headache and is taken daily by the patient whether or not the patient has a headache. Acute medications are used only as needed to treat a headache. MOU relates only to how frequently the patient uses acute medications.

Figure 9:
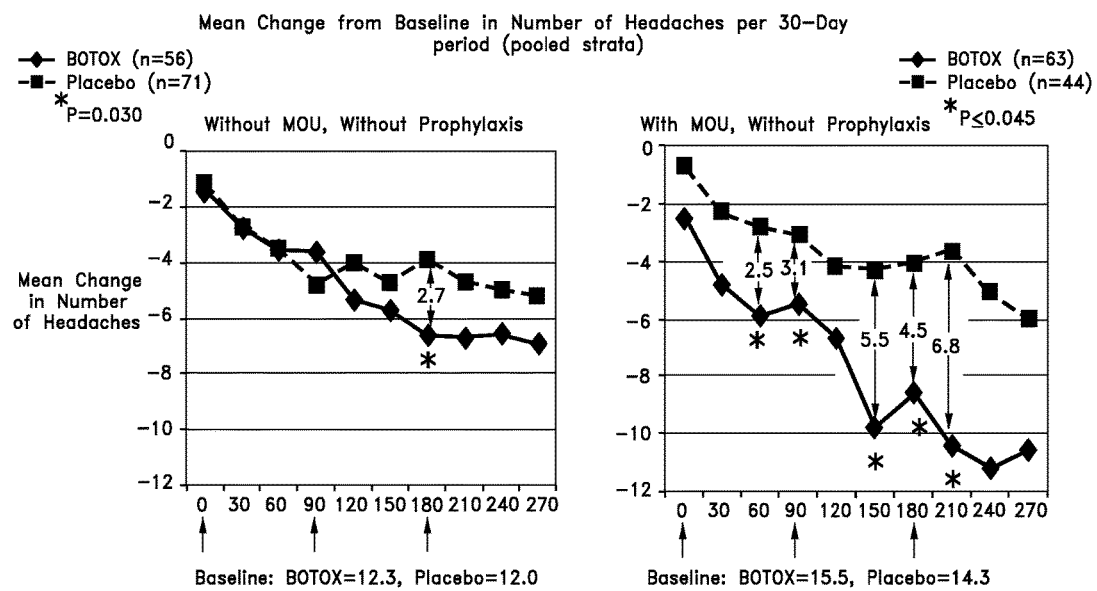

FIG. 9 comprises two graphs which shows the mean change in the number of headaches experienced by patients over a thirty day period after administration of BOTOX, where the patients either were not concurrently using another headache prophylaxis treatment and did not have a medication overuse disorder (left hand side graph) or the patients were not concurrently using another headache prophylaxis treatment and did have a medication overuse disorder (right hand side graph).

Figure 10:
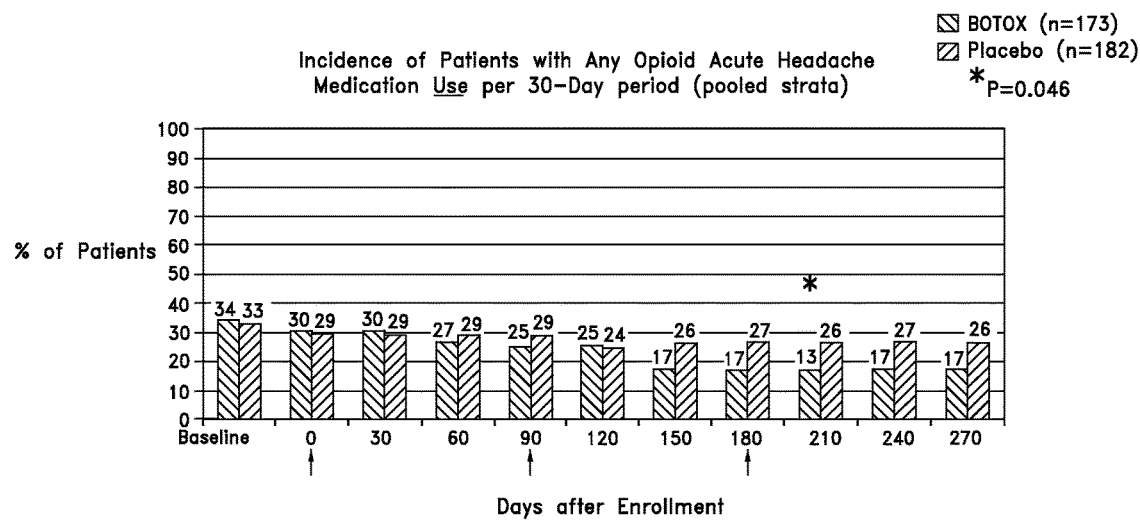

FIG. 10 is a bar chart showing the percentage of patients over a thirty day period after administration of BOTOX who were also using an opioid acute headache medication to control their headaches.

Figure 11:
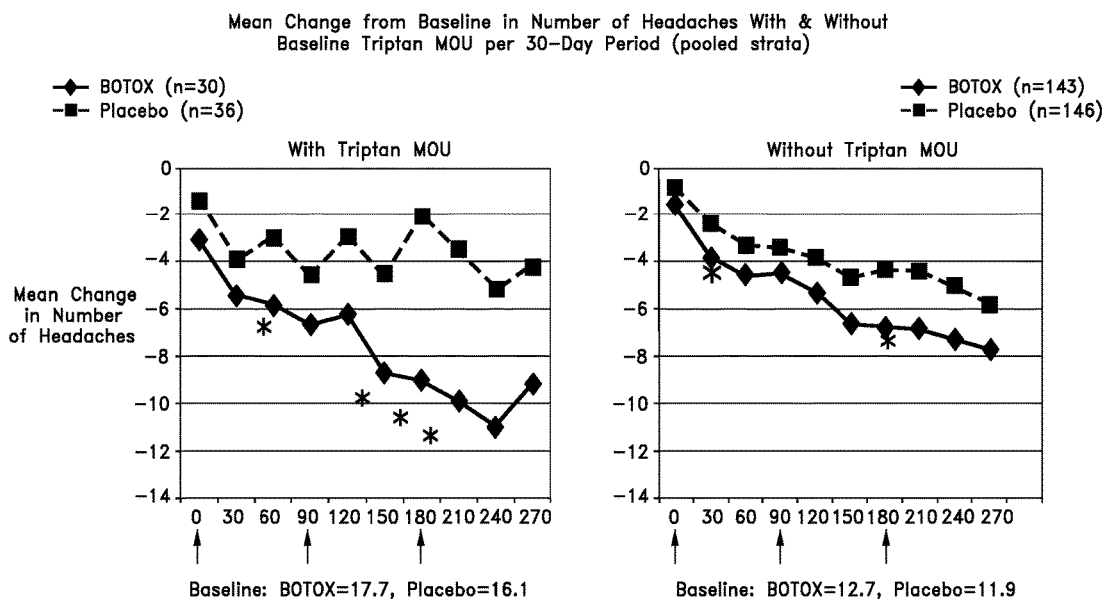

FIG. 11 comprises two graphs which shows the mean change in the number of headaches experienced by patients over a thirty day period after administration of BOTOX, where the patients either were triptan medication overuse patients (left hand side graph) or the patients were not triptan medication overuse patients (right hand side graph).

Figure 12:
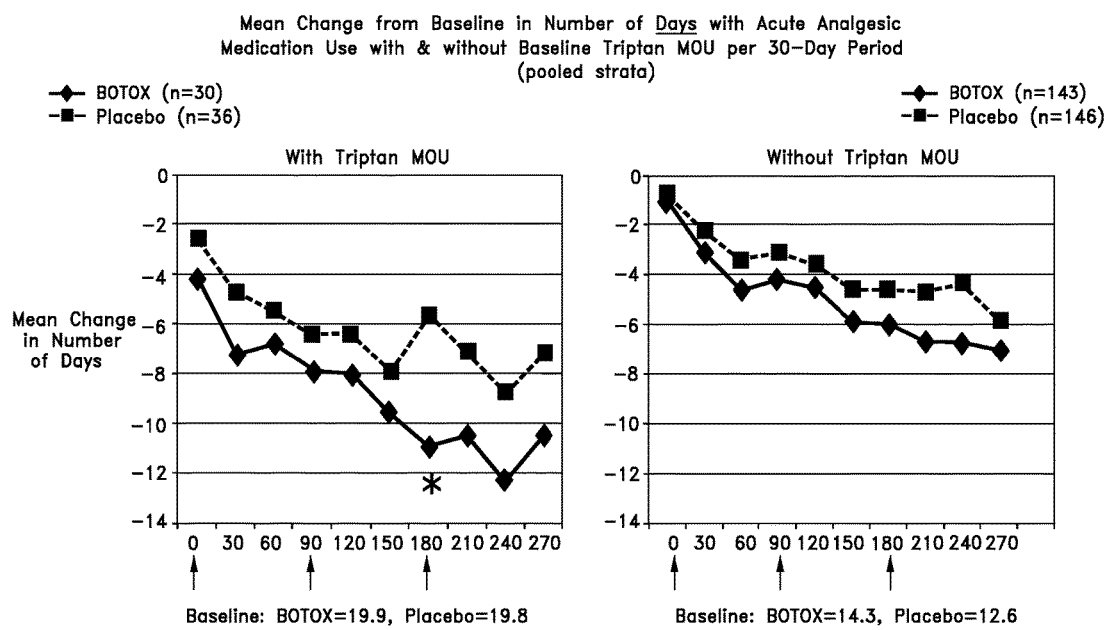

FIG. 12 comprises two graphs which shows the mean change from baseline (after administration of BOTOX) in number of days with acute headache (analgesic) medication use by the patients, where the patients were either triptan medication overuse patients (left hand side graph) or the patients were not triptan medication overuse patients (right hand side graph).

Figure 13:
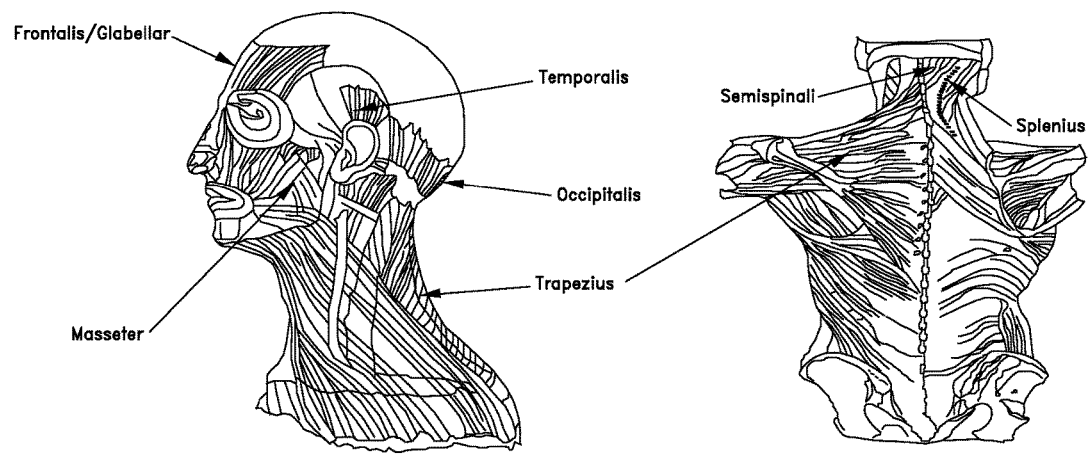

FIG. 13 comprises on the left side, a left side diagrammatic view of human muscle anatomy from the shoulders up, and on the right side of FIG. 13 a diagrammatic view of the back or trunk (including the neck), both views in FIG. 13 showing the anatomy and placement of the muscles with the overlying skin removed.

Figure 14:
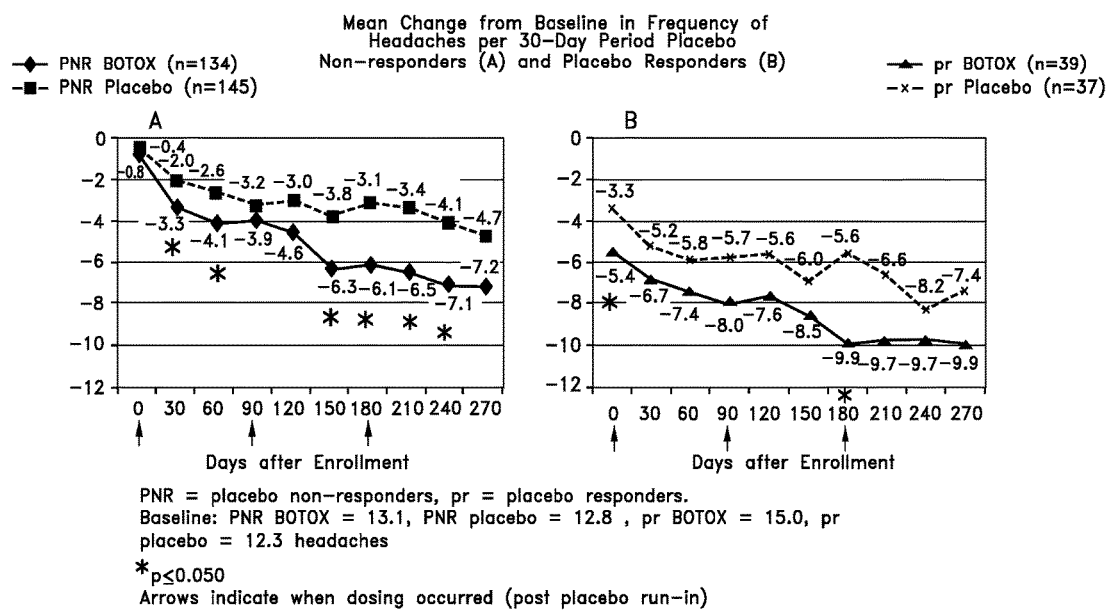

FIG. 14 comprises two graphs which show the mean change from baseline in the frequency of headaches per 30-day period for placebo non-responders (graph A) and placebo responders (graph B).

Figure 15:
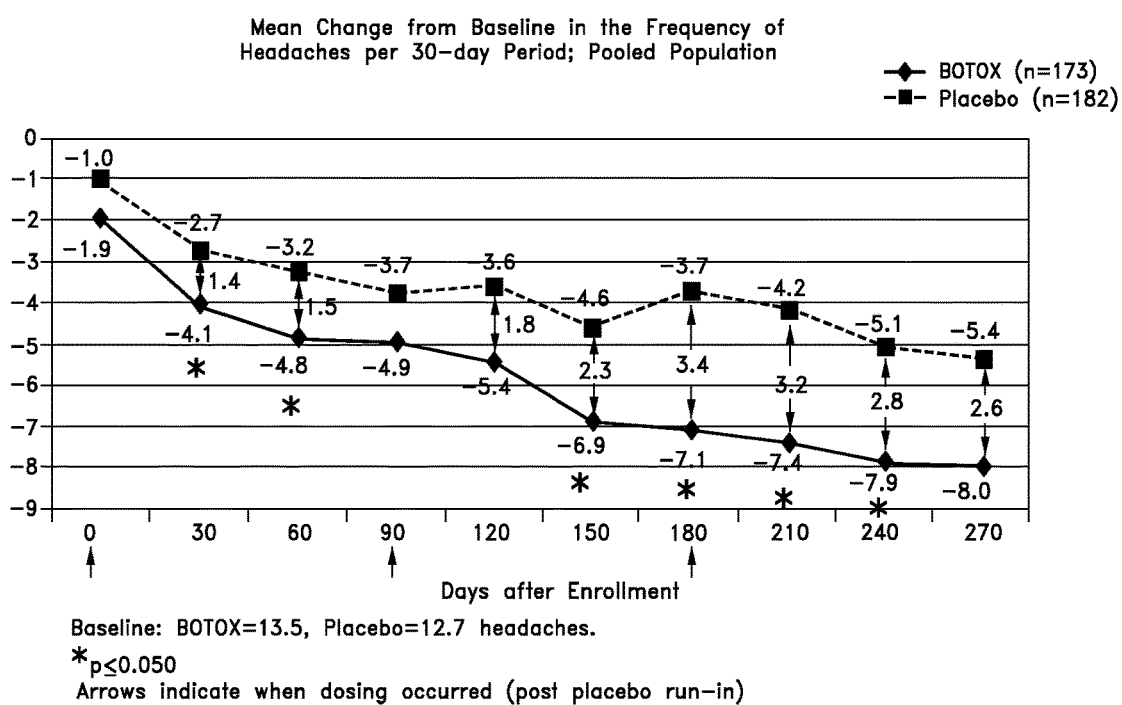

FIG. 15 is a graph which shows the mean change from baseline in the frequency of headaches per 30-day period, for a pooled population of patients.

Figure 16:
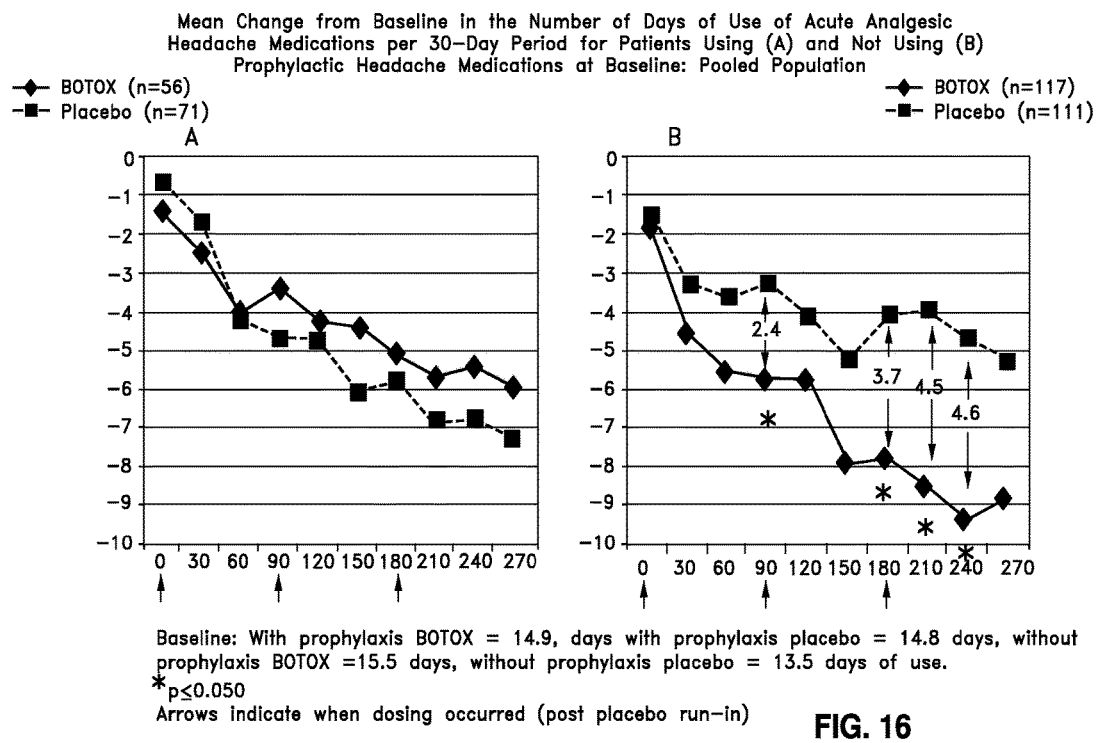

FIG. 16 comprises two graphs which show mean change from baseline in the number of days of use of acute analgesic headache medications per 30-day period for patients using (graph A) and not using (graph B) prophylactic headache medications at baseline, for a pooled population of patients.

DESCRIPTION

Figure 1:
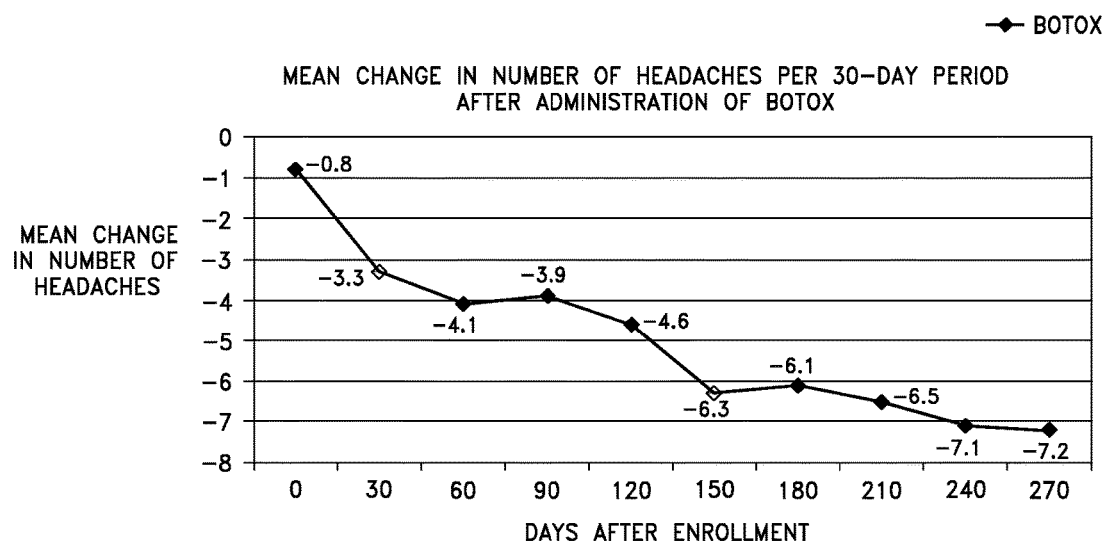
Figure 2:
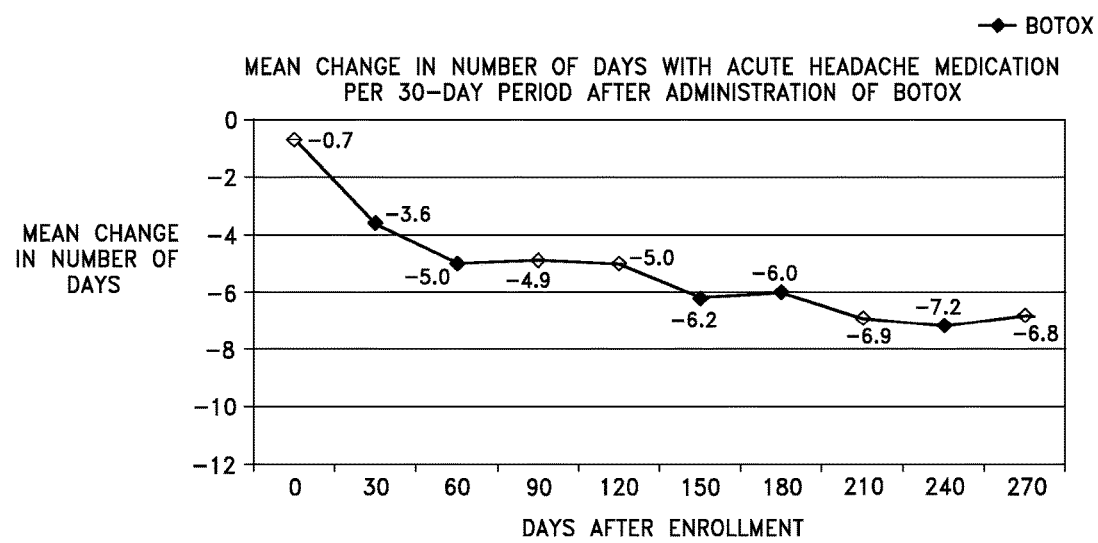
Figure 3:
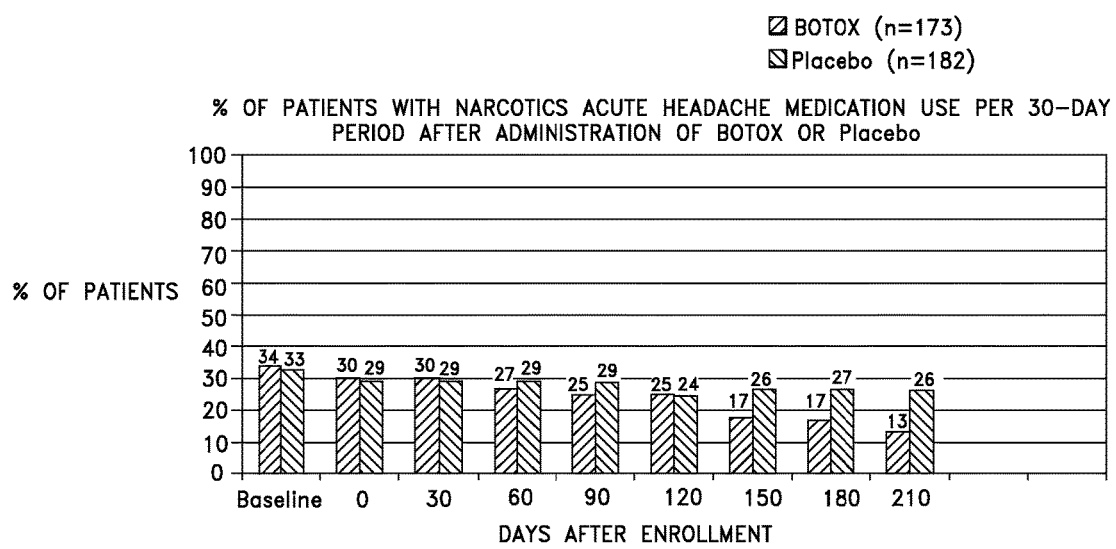
FIG. 3 is a graph which shows a comparison of the percent of patients (some who had been administered BOTOX and some who had been administered a placebo) who were over a thirty day period using narcotics medication to control acute headache pain.

The present invention is based on the discovery that a botulinum toxin can be used to treat a patient who is overusing a pain alleviation medication to treat his or her pain (such as a headache pain), to reduce both (a) the number of headaches experienced by the patient (see FIG. 1) and (b) the daily use of acute headache pain medication by the patient (FIG. 2). In particular we have found (see FIG. 3) that a botulinum toxin can be used to reduce use by patients of narcotic pain medication. Medication overuse to treat headache pain ("MOH") is a recognized disorder.

Figure 4:
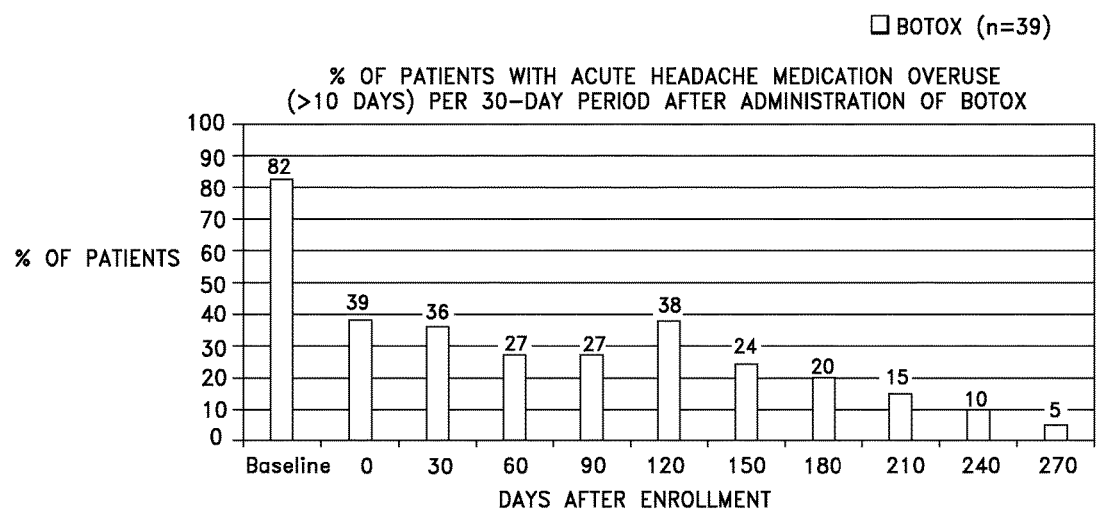
FIG. 4 is a graph which shows results that there was a decrease in the percent of patients who had acute headache medication overuse in a thirty day period after administration of BOTOX.

Additionally, we found that use of a botulinum toxin in patients who were overusing pain alleviation medication experienced a significant reduction in their use of such medications after treatment with a botulinum toxin (see FIG. 4). We also found that there was a significant reduction in the intake of triptan medications in triptan medication overuse patients (see FIG. 5).

Our invention can also be used as part of a detoxification protocol whereby a patient who is being weaned off acute pain medications is facilitated in this goal by concurrent administration of a botulinum toxin. Our invention can also be used to treat other chronic pain conditions (e.g. back pain, neuropathic pain, allodynia, fibromyalgia, etc.) which can include patients that overuse acute medications, specifically narcotics and triptans.

According to our invention, a medication overuse disorder can be treated by local administration of a therapeutically effective amount of a botulinum toxin. Thus, a botulinum toxin (such as a botulinum toxin serotype A, B, $C_1$, D, E, F or G) can be injected (i.e. intramuscular injection) into or in the vicinity where a patient is experiencing the pain to thereby suppress the pain or prevent its occurrence. Alternately, the botulinum toxin can be administered to an intradermal or subdermal pain sensory neuron thereby suppressing and treating such a medication overuse disorder.

Our invention is preferably practised by administering a botulinum toxin directly to a location where a patient is or is predisposed to experience pain. Without wishing to be bound by theory a physiological mechanism can be proposed for the efficacy of the present invention. It is known that muscles have a complex system of innervation and sensory output. Thus, anterior motor neurons located in each segment of the anterior horns of the spinal cord gray matter give rise to efferent alpha motor neurons and efferent gamma motor neurons that leave the spinal cord by way of the anterior roots to innervate skeletal (extrafusal) muscle fibers. The alpha motor neurons cause contraction of extrafusal skeletal muscle fibers while the gamma motor neurons innervate the intrafusal fibers of skeletal muscle. As well as excitation by these two type of efferent anterior motor neuron projections, there are additional, afferent sensory neurons which project from muscle spindle and golgi tendon organs and act to transmit information regarding various muscle parameter status to the spinal cord, cerebellum and cerebral cortex. These afferent motor neurons which relay sensory information from the muscle spindle include type Ia and type II sensory afferent neurons. See e.g. pages 686-688 of Guyton A. C. et al., *Textbook of Medical Physiology*, W.B. Saunders Company 1996, ninth edition.

Significantly, it has been determined that a botulinum toxin can act to reduce transmission of sensory information from muscle type Ia afferent neurons. Aoki, K., *Physiology and pharmacology of therapeutic botulinum neurotoxins*, in Kreyden, O., editor, Hyperhidrosis and botulinum toxin in dermatology, Basel, Karger; 2002; 30: pages 107-116, at 109-110. And it has been hypothesized that botulinum toxin can have a direct effect upon muscle cell sensory afferents and modify signals from these afferents to the central nervous system. See e.g. Brin, M., et al., *Botulinum toxin type A: pharmacology*, in Mayer N., editor, Spasticity: etiology, evaluation, management and the role of botulinum toxin, 2002; pages 110-124, at 112-113; Cui, M., et al., *Mechanisms of the antinociceptive effect of subcutaneous BOTOX®: inhibition of peripheral and central nociceptive processing*, Naunyn Schmiedebergs Arch Pharmacol 2002; 365 (suppl 2): R17; Aoki, K., et al., *Botulinum toxin type A and other botulinum toxin serotypes: a comparative review of biochemical and pharmacological actions*, Eur J. Neurol 2001: (suppl 5); 21-29. Thus, it has been demonstrated that botulinum toxin can cause an altered sensory output from muscle to CNS and brain.

Importantly, the sensory neurons from which afferent output is to be inhibited by a method according to the present invention need not be located on or within a muscle, but can be in an intradermal or subdermal location.

Thus, pain can be due to sensory input from afferent facial area neurons. Administration of a botulinum toxin to a facial muscles or skin to reduce sensory output from the muscle can result in alleviation of and prevention of pain.

It is our hypothesis, as may be the case in the treatment of a migraine headache with a botulinum toxin, that signals transmitted by afferent pain nerves in or on muscle tissue (i.e. muscle spindle fibers and muscle pain fibers) or as a part of sensory structures in the skin or subdermally induce the pain sensation. That is, afferent signal from muscles or skin structures provide sensory information to the brain which then leads to the generation of pain. Thus, a local administration of a botulinum toxin to muscle spindle fibers, pain fibers or other sensors in or in the vicinity of a muscle can act to alter the neural signal afferent output from these muscles to the brain and thereby decrease the sensation of pain.

Important elements of our invention are firstly that is practiced by use of a local administration of low dose of a botulinum toxin. The selected low dose may not cause a muscle paralysis. Secondly, the invention can be practiced by local administration of the low dose of the botulinum toxin to the muscle or to the muscle group which initiates the pain sensation.

The amount of the Clostridial toxin administered according to a method within the scope of the disclosed invention can vary according to the particular characteristics of the pain being treated, including its severity and other various patient variables including size, weight, age, and responsiveness to therapy. To guide the practitioner, typically, no less than about 1 unit and no more than about 25 units of a botulinum toxin type A (such as BOTOX®) is administered per injection site (i.e. to each muscle portion injected), per patient treatment session. For a botulinum toxin type A such as DYSPORT®, no less than about 2 units and no more about 125 units of the botulinum toxin type A are administered per injection site, per patient treatment session. For a botulinum toxin type B such as MYOBLOC®, no less than about 40 units and no more about 1500 units of the botulinum toxin type B are administered per injection site, per patiMore preferablyent treatment session. Less than about 1, 2 or 40 units (of BOTOX®, DYSPORT® and MYOBLOC® respectively) can fail to achieve a desired therapeutic effect, while more than about 25, 125 or 1500 units (of BOTOX®, DYSPORT® and MYOBLOC® respectively) can result in significant muscle hypotonicity, weakness and/or paralysis.

More preferably: for BOTOX® no less than about 2 units and no more about 20 units of a botulinum toxin type A; for DYSPORT® no less than about 4 units and no more than about 100 units, and; for MYOBLOC®, no less than about 80 units and no more than about 1000 units are, respectively, administered per injection site, per patient treatment session.

Most preferably: for BOTOX® no less than about 5 units and no more about 15 units of a botulinum toxin type A; for DYSPORT® no less than about 20 units and no more than about 75 units, and; for MYOBLOC®, no less than about 200 units and no more than about 750 units are, respectively, administered per injection site, per patient treatment session. It is important to note that there can be multiple injection sites (i.e. a pattern of injections) for each patient treatment session.

Generally, the total amount of BOTOX®, DYSPORT® or MYOBLOC®, suitable for administration to a patient according to the methods of the invention disclosed herein should not exceed about 300 units, about 1,500 units or about 15,000 units respectively, per treatment session.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). For example, the route and dosage for administration of a neurotoxin according to the present disclosed invention can be selected based upon criteria such as the solubility characteristics of the neurotoxin chosen as well as the intensity of pain perceived.

The present invention is based on the discovery that local administration of a Clostridial toxin can provide significant and long lasting relief and prevention of pain and treatment of a medication overuse disorder. The Clostridial toxins used in accordance with the invention disclosed herein can inhibit transmission of chemical or electrical signals between select neuronal groups that are involved in generation of pain. The Clostridial toxins preferably are not cytotoxic to the cells that are exposed to the Clostridial toxin. The Clostridial toxin can inhibit neurotransmission by reducing or preventing exocytosis of neurotransmitter from the neurons exposed to the Clostridial toxin. Or the applied Clostridial toxin can reduce neurotransmission by inhibiting the generation of action potentials of the neurons exposed to the toxin. The headache and headache pain prevention and alleviation effects provided by the Clostridial toxin can persist for a relatively long period of time, for example, for more than two months, and potentially for several years.

Examples of Clostridial toxins within the scope of the present invention include neurotoxins made by *Clostridium botulinum, Clostridium butyricum* and *Clostridium baratii* species. In addition, the botulinum toxins used in the methods of the invention may be a botulinum toxin selected from a group of botulinum toxin types A, B, C, D, E, F, and G. In one embodiment of the invention, the botulinum neurotoxin administered to the patient is botulinum toxin type A. Botulinum toxin type A is desirable due to its high potency in humans, ready availability, and known use for the treatment of skeletal and smooth muscle disorders when locally administered by intramuscular injection. The present invention also includes the use of (a) Clostridial neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Although the composition may only contain a single type of neurotoxin, such as botulinum toxin type A, as the active ingredient to suppress neurotransmission, other therapeutic compositions may include two or more types of neurotoxins, which may provide enhanced therapeutic treatment of a headache. For example, a composition administered to a patient may include botulinum toxin type A and botulinum toxin type B. Administering a single composition containing two different neurotoxins may permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the $GABA_A$ receptor. The $GABA_A$ receptor inhibits neuronal activity by effectively shunting current flow across the cell membrane. $GABA_A$ receptor modulators may enhance the inhibitory effects of the $GABA_A$ receptor and reduce electrical or chemical signal transmission from the neurons. Examples of $GABA_A$ receptor modulators include benzodiazepines, such as diazepam, oxazepam, lorazepam, prazepam, alprazolam, halazepam, chlordiazepoxide, and clorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat pain can include one or more neurotoxins, such as botulinum toxins, in addition to ion channel receptor modulators that may reduce neurotransmission.

The neurotoxin may be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a botulinum toxin within a tissue appears to be a function of dose and can be graduated. Jankovic J., et al *Therapy With Botulinum Toxin*, Marcel Dekker, Inc., (1994), page 150. Thus, diffusion of botulinum toxin can be controlled to reduce potentially undesirable side effects that may affect the patient's cognitive abilities. For example, the neurotoxin can be administered so that the neurotoxin primarily effects neural systems believed to be involved in the generation of pain and/or inflammation, and does not have negatively adverse effects on other neural systems.

A polyanhydride polymer, Gliadel® (Stolle R & D, Inc., Cincinnati, Ohio) a copolymer of poly-carboxyphenoxypropane and sebacic acid in a ratio of 20:80 has been used to make implants, and has been intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al, *Placebo-Controlled Trial of Safety and Efficacy of Intraoperative Controlled*

*Delivery by Biodegradable Polymers of Chemotherapy for Recurrent Gliomas*, Lancet 345; 1008-1012:1995.

Implants useful in practicing the methods disclosed herein may be prepared by mixing a desired amount of a stabilized neurotoxin (such as non-reconstituted BOTOX®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58; 672-684:1998.

Local administration of a Clostridial toxin, such as a botulinum toxin, can provide a high, local therapeutic level of the toxin. A controlled release polymer capable of long term, local delivery of a Clostridial toxin to a target muscle permits effective dosing of a target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

Local administration of a botulinum toxin, according to the present invention, by injection or implant to a target tissue provides a superior alternative to systemic administration of pharmaceuticals to patients to alleviate pain and to treat a MOD such as MOH.

The amount of a Clostridial toxin selected for local administration to a target tissue according to the present disclosed invention can be varied based upon criteria such as the severity of the pain or type of headache or MOD being treated, the extent of muscle tissue to be treated, solubility characteristics of the neurotoxin toxin chosen as well as the age, sex, weight and health of the patient. For example, the extent of the area of muscle tissue influenced is believed to be proportional to the volume of neurotoxin injected, while the quantity of the suppressant effect is, for most dose ranges, believed to be proportional to the concentration of a Clostridial toxin administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill).

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality and general health perceptions. Scores obtained can be compared to published values available for various general and patient populations.

EXAMPLE

The following non-limiting example provides those of ordinary skill in the art with specific preferred methods to treat conditions within the scope of the present invention and are not intended to limit the scope of the invention. In the following examples various modes of non-systemic administration of a Clostridial neurotoxin can be carried out. For example, by intramuscular injection, subcutaneous injection or by implantation of a controlled release implant.

Example 1

Botulinum Toxin Type A Therapy for Headache Pain and for a Medication Overuse Headache Disorder Summary of the Study A clinical study was carried out which included patients who complained of headache pain and who took frequent acute pain medications, such as narcotics and triptans to control the pain. Some of these patients were diagnosed with medication overuse headache (MOH) disorder. A botulinum toxin (BOTOX) was administered to the patients in the study at three times during the clinical study: at day 0, at day 90 and at day 180. The BOTOX injections were administered intramuscularly in an average of 20 separate injections to each patient at each of the three injection sessions. The BOTOX was administered to up to seven different muscles (i.e. 20 total injections into 7 muscles).

From 105 to 260 units of the BOTOX was administered to each patient at each of the three treatment sessions. It was found that the patients experienced a reduction in both (a) the number of headaches experienced by such patients (FIG. 1), and; (b) the daily use of acute headache pain medication by these patients (FIG. 2). In particular it was found (FIG. 3) that a botulinum toxin can be used to reduce use by these patients of narcotic pain medication.

Figure 5:
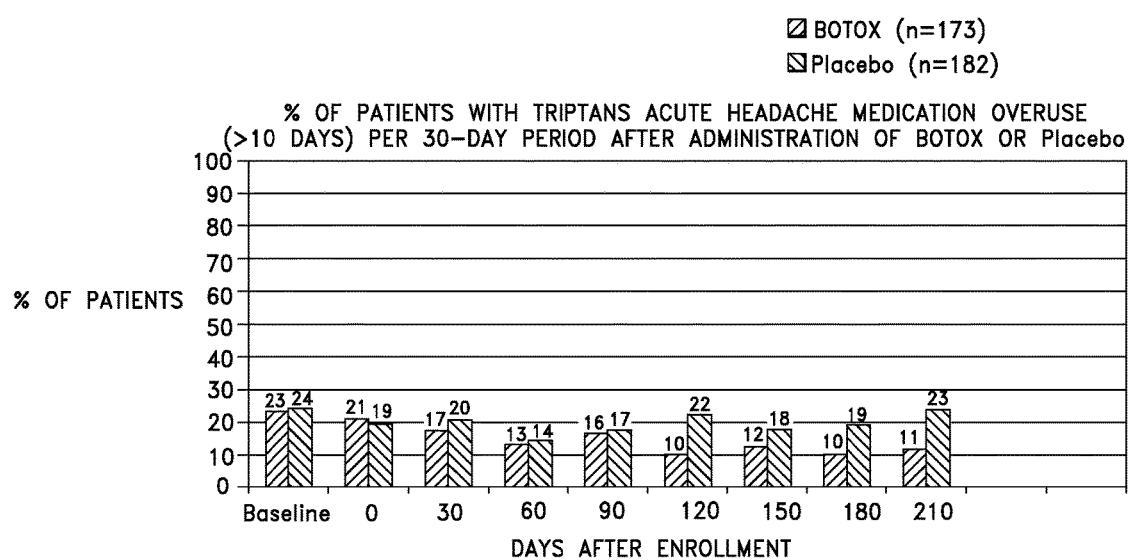
FIG. 5 is a graph which shows that there was a decrease in the percent of patients who had triptans acute headache medication overuse in a thirty day period after administration of BOTOX.

Additionally, it was found that use of a botulinum toxin in patients who were overusing pain alleviation medication resulted in a significant reduction in their use of such medications after treatment with a botulinum toxin (see FIG. 4). It was also found that there was a significant reduction in the intake of triptan medications in overuse patients (FIG. 5). Thus, this clinical study surprisingly showed that a botulinum toxin can be used to treat a medication overuse headache disorder (MOH).

As set forth above, the study carried out showed that a botulinum toxin was effective to treat headache in a patients overusing medications (referred to below as "MOU", meaning medication overuse patients). To reiterate, and as shown in FIG. 6, use of a botulinum toxin permitted a significant reduction in number of headaches in the population that was overusing medication at baseline (i.e. at initiation of the study).

The study also demonstrated (see FIG. 7) that a botulinum toxin was more effective in patients who were not using a concurrent headache prophylaxis treatment (i.e. BOTOX monotherapy) regardless of any medication overuse issue.

Additionally, the same study showed (see FIGS. 8 and 9) that a botulinum toxin was more effective in the patients who were not using a concurrent headache prophylaxis treatment ("without prophylaxis") (i.e. a botulinum toxin [i.e. BOTOX monotherapy) and were overusing medication (i.e. "MOU" patients). This is a discovery in addition to our discovery that a botulinum toxin can be used to treat headache in a patient overusing acute medication, without regard to the fact that the patient is being treated with a botulinum toxin monotherapy or that he or she is being treated for headache with other headache prophylaxis medications.

Furthermore, with regard to acute medication use in patients (not overuse, but any use) the study showed that treatment of headache with a botulinum toxin resulted in a significant decrease in use of narcotics by these patients (see eg day 210 in FIG. 10).

Finally, and significantly the study also showed (see FIGS. 11 and 12) that after treatment with a botulinum toxin (such as BOTOX) there was a greater decrease in the frequency of headache and as well in the number of days acute analgesic medications were required in the patients who were overusing triptans headache medication at baseline (i.e. upon study initiation), as compared to the patients who were not overusing triptan medications. This indicates that triptans are more effective to treat headache when used in conjunction with a botulinum toxin. Thus a method for increasing the effectiveness of a triptan to treat a headache can be carried out by using a triptan and a botulinum toxin concurrently to treat a headache.

As is well known, triptans don't prevent headaches from occurring. Instead they act only to treat the pain associated with a headache that a patient is currently experiencing. See eg Gladstone J P., et al., *Newer formulations of the triptans: advances in migraine management*, Drugs. 2003; 63(21): 2285-305. Clinically, triptan medication overuse appears to actually cause or to exacerbate headache pain, as opposed to the alleviation of headache pain which can result from normal triptan use. See eg Relja G., et al., *Headache induced by chronic substance use: analysis of medication overused and minimum dose required to induce headache*, Headache. 2004 February; 44(2):148-53. Therefore, it was a surprising discovery, as set forth by FIGS. 11 and 12, for us to find that administration of a botulinum toxin helps to prevent headaches in a patient population who have headaches, more frequent headaches or exacerbated headaches due to triptan medication overuse. This discovery is demonstrated by study results and patient observations showing that triptan MOU patients needed less triptan medication after botulinum toxin administration.

Detailed Study Description

The study carried out was a multicenter, double-blind, randomized, placebo-controlled, parallel group study of multiple treatments of BOTOX® (botulinum toxin type A purified neurotoxin complex) for the prophylactic treatment of headaches in a chronic headache population.

ABBREVIATIONS AND DEFINITION OF TERMS

AGN 191622 Botulinum Toxin, Type A Purified Neurotoxin Complex
ANOVA Analysis of variance
ANCOVA Analysis of covariance
ATC Anatomical-Therapeutic-Chemical drug thesaurus
Baseline period First 30-day period during which patient enter the screening period (Day −60 to Day −30)
BOTOX® BOTOX® (Botulinum Toxin Type A) Purified Neurotoxin Complex
bpm Beats per minute
CDH Chronic daily headache
CFR Code of Federal Regulations
CGRP Calcitonin gene-related peptide
COSTART Coding symbols for thesaurus of adverse reaction terms
CRF Case report form
CSR Clinical study report
CTTH Chronic tension type headache
FDA United States Food and Drug Administration
GCP Good Clinical Practice
GLP Good Laboratory Practice
HCG Human chorionic gonadotropin
HIQ Headache Impact Questionnaire
Hemicrania continua Rare, indomethacin-responsive headache disorder characterized by a continuous but fluctuating, moderately-severe, unilateral headache
HPSQOL Headache Pain Specific Quality of Life Questionnaire
ICHD International Classification of Headache Disorders
IEC Independent Ethics Committee
IHS International Headache Society
IVRS Interactive Voice Response System
IRB Institutional Review Board
$LD_{50}$ Calculated median lethal dose
MIDAS Migraine Disability Assessment
Month 30 day period
MS-QOL Migraine-Specific Measure of Quality of Life
NA Not available; not applicable
New daily persistent Acute onset of constant unremitting headache with no history of headache CTTH or migraine
NOS Not otherwise specified
NSAIDs Nonsteroidal anti-inflammatory drugs
QOL Quality of life
RBC Red blood cell
Run-in period Day −30 to Day −1, when all patients received placebo treatment
SD Standard deviation
SGOT Serum glutamic-oxaloacetic transaminase
SGPT Serum glutamic-pyruvic transaminase
Transformed Chronic daily headache evolving from episodic migraine Migraine
Treatment 1 Visit at which patients received injection of placebo and entered the placebo run-in, also called Day −30 (Visit 2)
Treatment 2 Visit at which patients were randomized to receive either BOTOX® or placebo, also called Day 0 (Visit 3)
Treatment 3 Visit at which patients received either second treatment of BOTOX® or third treatment of placebo, also called Day 90 (Visit 6)
Treatment 4 Visit at which patients received either third treatment of BOTOX® or fourth treatment of placebo, also called Day 180 (Visit 9)
U Unit (1 U corresponds to the calculated median lethal intraperitoneal dose [$LD_{50}$] in mice)
WBC White blood cell
WHO World Health Organization

LITERATURE REFERENCES CITED BELOW

Aoki K R. Evidence for antinociceptive activity of botulinum toxin type A in pain management. Headache 2003; 43 Suppl 1:S9-15.
Aoki K R. Pharmacology and immunology of botulinum toxin serotypes. J Neurol 2001; 248 Suppl 1:1/3-1/10.
Bigal M E, Sheftell F D, Rapoport A M, et al. Chronic daily headache in a tertiary care population: correlation between International Headache Society diagnostic criteria and proposed revisions of criteria for chronic daily headache. Cephalalgia 2002; 22:432-438.

Binder W J, Brin M F, Blitzer A. Botulinum toxin type A (BOTOX) for treatment of migraine headaches: an open-label study. Otolaryngol Head Neck Surg 2000; 123(6): 669-676.

Blumenfeld A M. Botulinum toxin type A as an effective prophylactic treatment in primary headache disorders. Headache 2003; 43:853-860.

Blumenfeld A M, Dodick D W, Silberstein S D. Botulinum neurotoxin for the treatment of migraine and other primary headache disorders. Dermatol Clin 2004; 22:167-175.

BOTOX® (package insert). Irvine, Calif.: Allergan Inc; 2004.

Brandes J L, Saper J R, Diamond M, et al. Topiramate for migraine prevention: a randomized controlled trial. JAMA; 2004; 291:965-973.

Brin M F, Fahn S, Moskowitz C, et al. Localized injections of botulinum toxin for the treatment of focal dystonia and hemifacial spasm. Movement Dis 1987; 2:237-254.

Brin M F, Swope D M, O'Brien C, et al. BOTOX® for migraine: double-blind, placebo-controlled, region-specific evaluation. Cephalalgia 2000; 20:421-422.

Castillo J P, Munoz P, Guitera V, et al. Epidemiology of chronic daily headache in the general population. Headache 1999; 39:190-196.

Cheshire W P, Abashian S W, Mann J D. Botulinum toxin in the treatment of myofascial pain syndrome. Pain 1994; 59:65-69.

Colas R, Munoz P, Temprano R, et al. Chronic daily headache with analgesic overuse: epidemiology and impact on quality of life. Neurology 2004; 62:1338-1342.

Couch J R. Placebo effect and clinical trials in migraine therapy. Meth Prob Migraine Trials, Neuroepid 1987; 6:178-185.

Cui M, Khanijou S, Rubino J, et al. Subcutaneous administration of botulinum toxin A reduces formalin-induced pain. Pain 2004; 107:125-133.

Depakote® ER (package insert). Abbott Laboratories; 2003.

Durham P L, Cady Ryan, Cady Roger. Regulation of calcitonin gene-related peptide secretion from trigeminal nerve cells by botulinum toxin type A: implications for migraine therapy. Headache 2004; 44:35-42.

Elashoff J D. nQuery Advisor Version 4.0 User's Guide, Los Angeles, 2000.

European Agency for the Evaluation of Medicinal Products. Note for guidance on clinical investigation of medicinal products for the treatment of migraine. December 2003.

Foster L, Clapp L, Erickson M, Jabbari B. Botulinum toxin A and chronic low back pain. A randomized, double-blind study. Neurol 2001; 56:1290-1293.

Freund B J, Schwartz M. Use of botulinum toxin in chronic whiplash-associated disorder. Clin J Pain 2002; 18(6 Suppl):5163-5168.

Headache Classification Subcommittee of the International Headache Society. The international classification of headache disorders, 2$^{nd}$ ed. Cephalalgia 2004; 24 Suppl 1:1-151.

Headache Classification Committee of the International Headache Society. Classification and diagnostic criteria for headache disorders, cranial neuralgias and facial pain. Cephalalgia 1988; 8 Suppl 7:1-96.

Hering R, Gardiner I, Catarci T, Witmarch T, Steiner T, de Belleroche J. Cellular adaptation in migraineurs with chronic daily headache. Cephalalgia 1993; 13:261-6.

Holroyd K A, Stensland M, Lipchik G L, et al. Psychosocial correlates and impact of chronic tension-type headaches. Headache 2000; 40:3-16.

International Headache Society committee on Clinical Trials in Migraine. Guidelines for controlled trials of drugs in migraine. First edition. Cephalalgia 1991; 11:1-12.

Klapper J A, Mathew N T, Klapper A et al. Botulinum toxin type A (BTX-A) for the prophylaxis of chronic daily headache. Cephalalgia 2000; 20:292-293.

Linde M, Limmroth V, Dahlöf C, on behalf of the Headache Masters Programme. Ethical aspects of placebo in migraine research. Cephalalgia 2003; 23:491-495.

Linton-Dahlöf, M Linde, Dahlöf C. Withdrawal therapy improves chronic daily headache associated with long-term misuse of headache medication: a retrospective study. Cephalalgia 2000; 20:658-662.

Lipton R B, Bigal M E. Chronic daily headache: is analgesic overuse a cause or a consequence? Neurology 2003; 61:154-155.

Lipton R B, Stewart W F. Migraine headaches: epidemiology and comorbidity. Clin Neuroscience 1998; 5:2-9.

Manzoni G C, Granella F, Sandrini G, et al. Classification of chronic daily headache by International Headache Society criteria: limits and new proposals. Cephalalgia 1995; 15:37-43.

Mathew N T, Reuveni U, Perez F. Transformed or evolutive migraine Headache 1987; 27:102-106.

Mathew N, Kaup A, Kailasam J. botulinum toxin type A modifies chronic migraine further long-term (3 years) experience with up to ten sets of treatments. Headache 2003; 43:576.

Monzon M J, Lainez M J A. Quality of life in migraine and chronic daily headache patients. Cephalalgia 1998; 18:638-643.

Mauskop A. Botulinum toxin in the treatment of chronic daily headaches. Cephalalgia 1999; 19:453.

O'Brien P C, Fleming T R. A multiple testing procedure for clinical trials. Biometrics 1979; 35:549-556.

Ondo W G, Vuong K D, Derman H S. Botulinum toxin A for chronic daily headache: a randomized, placebo-controlled, parallel design study. Cephalalgia 2004; 24:60-5.

Purkiss J, Welch M, Doward S, et al. Capsaicin-stimulated release of substance P from cultured dorsal root ganglion neurons: involvement of two distinct mechanisms. Biochem Pharmacol 2000; 59:1403-1406.

Rahimtoola H, Buurma H, Tijssen C C, et al. Migraine prophylactic medication usage patterns in The Netherlands. Cephalalgia 2003; 23:293-301.

Saper J R, Lake A E III, Cantrell D T, et al. Chronic daily headache prophylaxis with tizanidine: a double-blind, placebo-controlled, multicenter outcome study. Headache 2002; 42:470-482.

Scher A I, Stewart W F, Liberman J, et al. Prevalence of frequent headache in a population sample. Headache 1998; 38:497-506.

Schwartz B S, Stewart W F, Lipton R B. Loss of workdays and decreased work effectiveness associated with headache in the workplace. J Occup Environ Med 1997; 39:320-327.

Siegel S. Non-parametric statistics for the behavioral sciences. New York: McGraw-Hill Book Company, 1956: 96:116-127.

Silberstein S D, Lipton R B. Chronic daily headache. Curr Opin Neurol 2000; 13:277-283.

Silberstein S D, Lipton R B. Chronic daily headache, including transformed migraine, chronic tension-type headache, and medication overuse. In: Silberstein S D, Lipton R B, Dalessio D J, eds. Wolff's headache and other head pain, 7$^{th}$ ed. New York, N.Y.: Oxford University Press; 2001:247-282.

Silberstein S D, Lipton R B, Sliwinski M. Classification of daily and near-daily headaches: field trial of revised IHS criteria. Neurology 1996; 47:871-875.

Silberstein S D, Lipton R B, Solomon S, Mathew N T. Classification of daily and near-daily headaches: proposed revisions to the IHS criteria. Headache 1994; 34:1-7.

Silberstein S D, Neto W, Schmitt J, et al. Topiramate in migraine prevention. Arch Neurol 2004; 61:490-495.

Silberstein S D, Silberstein M M. New concepts in the pathogenesis of headache. Part III. Pain Man 1990; 3:334-342.

Silvestrini M, Bartolini M, Coccia M, et al. Topiramate in the treatment of chronic migraine. Cephalalgia 2003; 23:820-824.

Smuts J A, Baker M K, Smuts H M, et al. Prophylactic treatment of chronic tension-type headache using botulinum toxin type A. Eur J Neurol 1999; 6(Suppl 4):599-5102.

Solomon G D, Sokbieranda F G, Genzen J R. Quality of life assessment among migraine patients treated with Sumatriptan. Headache 1995; 35:449-454.

Spira P J, Beran R G. Gabapentin in the prophylaxis of chronic daily headache: a randomized, placebo-controlled study. Neurology 2003; 61:1753-1759.

Stewart W F, Lipton R B, Celentano D D, et al. Prevalence of migraine headaches in the United States. Relation to age, income, race and other sociodemographic factors. JAMA 1992; 267:64-69.

Troost B T. Botulinum toxin type A (Botox) in the treatment of migraine and other headaches. Expert Rev Neurotherap 2004; 4:27-31.

Wang S J, Fuh J L, Lu S R, et al. Chronic daily headache in Chinese elderly: prevalence, risk factors and biannual follow-up. Neurology 2000; 54:314-319.

Wang S J, Fuh J L, Lu S R, et al. Quality of life differs among headache diagnoses: analysis of SF-36 survey in 901 headache patients. Pain 2001; 89:285-292.

Welch K M A, Nagesh V, Rozell K, et al. Functional MRI of chronic daily headache. Cephalalgia 1999; 19:462-463.

Welch K M, Goadsby P J. Chronic daily headache: nosology and pathophysiology. Curr Opin Neurol 2002; 15:287-95. Review.

Wissel J, Muller J, Dressnandt J, Heinen F, Naumann M, Topka H, Poewe W. Management of spasticity associated pain with botulinum toxin A. J Pain Symptom Manage 2000; 20:44-9.

This was a multicenter study, with investigators at 13 U.S. sites. Headache is probably the most common neurological symptom in clinical practice (Castillo et al, 1999). In the United States in 1 year, most of the population will have a headache and over 5% will seek medical aid (Silberstein and Silberstein, 1990). Headaches can be either episodic (less than or equal to 15 headache days per month) or chronic (greater than 15 headache days per month) (Silberstein and Lipton, 2001). Recurrent headaches are symptoms of a chronic primary headache disorder.

Chronic daily headache (CDH) is a heterogeneous disorder, affecting 4% to 5% of the general population (Castillo et al, 1999; Scher et al, 1998; Wang et al 2000). Chronic daily headache is the most common headache seen in headache specialty clinics (Silberstein et al, 1994). Although not included in the International Headache Society (IHS) classification (Headache Classification Subcommittee of the International Headache Society, 1988, revised 2004), the concept of CDH is well recognized (Silberstein and Lipton, 2000). Some investigators have suggested a revision of the IHS classification to include a defined CDH entity (Manzoni et al, 1995; Silberstein et al, 1994).

More than 90% of CDH patients initially report episodic headaches (Silberstein and Lipton, 2000). Patients in whom episodic migraines have progressed into chronic daily headache are described as having "transformed migraine" (Silberstein et al, 1994). Mathew et al (1987) reported that patients with CDH who evolved from initially episodic migraine differed from patients with episodic headaches alone regarding abnormal personality profile, elevated depression scores, identifiable stress, medication overuse and hypertension. Most patients with CDH report their role functioning and well-being as frequently and severely impaired (Holroyd et al, 2000), highlighting the importance of this group of headaches on quality of life (Monzon and Lainez, 1998; Wang et al, 2001). Very few studies have evaluated headache prophylactic treatment in patients with CDH (Saper et al, 2002; Slivestrini et al, 2003; Spira et al, 2003). To date, no drug has received regulatory authority approval for the prophylaxis of headaches in migraine patients with CDH. There appears to be an unmet medical need in this debilitated patient population.

BOTOX® therapy has been reported to alleviate pain associated with various conditions with or without concomitant excess muscle contractions (Aoki, 2001). This includes cervical dystonia (Brin et al, 1987), spasticity (Wissel et al, 2000), tension-associated headache (Smuts et al, 1999), chronic whiplash-associated neck pain (Freund and Schwartz, 2002), myofascial pain (Cheshire et al, 1994), migraine prophylaxis (Blumenfeld et al, 2004), and back pain (Foster et al, 2001). The toxin is known to inhibit the release of the neurotransmitter, acetylcholine, at the neuromuscular junction, thereby inhibiting striated muscle contractions. In the majority of pain syndromes where BOTOX® has been studied, inhibiting muscle spasms is an important component of its activity. However, the reduction of pain often occurs before the decrease in muscle contractions suggesting that BOTOX® has a more complex mechanism of action than initially hypothesized (Aoki, 2003). Data has been published which suggests a pain-reducing effect of BOTOX® separate from its neuromuscular activity. BOTOX® appears to act both peripherally (directly) and centrally (indirectly) on sensory nerves. The hypothesis that BOTOX® mediates an antinociceptive activity peripherally is supported by its inhibition of neurotransmitters such as glutamate (Cui et al, 2004), CGRP (calcitonin gene-related peptide) (Purkiss et al, 2000; Welch et al, 2000), and substance P (Durham et al, 2004). An indirect reduction of central sensitization is supported by studies investigating the stimulation of the immediate early gene, c-fos, using the formalin-challenged rat model. In these studies activation of the c-fos gene and expression of its protein product, Fos, indicate rapid neuronal firing in response to stimuli. BOTOX® treatment reduced Fos expression after formalin challenge in a dose-dependent manner indicating an indirect central effect in reducing pain (Cui et al, 2004).

The objective of this study was to evaluate the safety and efficacy of multiple treatments of BOTOX® compared with placebo for the prophylactic treatment of headaches in the chronic headache population.

This was a multicenter, double-blind, randomized, placebo-controlled, parallel-group clinical study of multiple treatments of BOTOX® compared with placebo in the management of patients with chronic daily headache. The overall duration of the study for each patient was 11 months.

Patients were screened at Day −60 (baseline period). During this period data were collected daily from the patient regarding specified characteristics of their headache episodes and headache medication use for 30 days using electronic telephone diaries. Following the baseline period, patients returned at Day −30 (Treatment 1) for the placebo run-in period. At this visit, patients meeting the inclusion/exclusion criteria were injected with single-masked placebo, and again recorded specified characteristics of their headache episodes for 30 days using electronic diaries. Treatment 1 injections were in a minimum of 6 muscle areas and 23 to 58 injection sites within these areas as specified in Table 9.4.1 and Figure 9.4.1 (see Section 9.4.1), dependent upon the location and severity of pain. The investigator also had the option to inject the masseter if the patient was experiencing pain in that muscle.

After 30 days (at Day 0) patients returned to be randomized for Treatment 2. Prior to randomization, using diary information collected during the placebo run-in period, patients were classified as a placebo responder if they had <16 headache days or had a ≥30% decrease from baseline in the frequency of headache days. All other patients were considered placebo non-responders. Patients within each stratum (responders, non-responders) were randomized to receive either BOTOX® or placebo at Day 0 (Treatment 2).

Patients received additional treatments at Day 90 (Treatment 3) and Day 180 (Treatment 4). Patients returned for follow-up visits at 30-day intervals following each treatment through Day 270. If a patient exited the study at any visit prior to Day 270 (exit), all exit procedures and evaluations were to be completed at that visit. For Treatments 2, 3, and 4, patients were injected with BOTOX® or placebo using the same dose and volume and in the same muscle areas and sites as in Treatment 1. The schedule of study visits and measurements is shown in Table 2.

The study design included the recognized elements of a well-controlled clinical trial that are necessary for an unbiased evaluation of the treatment effect. The study was randomized and double-blind to minimize investigator and patient bias. Blinding was ensured by the similarity in appearance of the vials of study medication and requiring that an individual at each study center who had no other study involvement reconstituted the study medication and filled the syringes for injection. A placebo-controlled, parallel-group design eliminated possible confounding effects that are inherent in other study designs. The design of this study generally conformed to the recommendations of the International Headache Society (IHS) for studies in the prophylactic treatment of migraine (IHS Committee on Clinical Trials in Migraine, 1991).

The present study was conducted to assess the potential benefit of BOTOX® in headache prophylaxis in the adult chronic daily headache population. The term chronic daily or chronic near-daily headache has been used to refer to very frequent headaches (i.e., 16 or more headache days a month) not related to a structural or systemic illness (Silberstein and Lipton, 2001). The key requirement for entry into the current study was primary headache disorder with 16 headache days per month by history and confirmed by electronic diary during baseline. Headache disorder could include any combination of episodic/chronic tension-type headaches, migraines with or without aura, and/or migrainous headaches (as defined by IHS criteria [Headache Classification Subcommittee of the IHS, 1988, revised 2004], and/or chronic daily headache as defined by Silberstein and Lipton, 2001).

In contrast to the fixed site/fixed dosage treatment approach used in previous clinical studies in the episodic migraine population, physicians participating in this study were allowed to use a more individualized or patient-tailored treatment approach depending on the location of the patient's head pain. Specifically, physicians were given the opportunity to determine the number of injection sites and the dosage within a protocol-specified range to be administered for the specified frontal and posterior muscle areas of the head and neck, depending on the location and severity of a patient's headache. Maximum dose levels allowed in this study also were higher than those used in previous studies due to the addition of injection of larger, posterior pericranial and neck muscles.

Due to the high placebo response rate seen in the previous studies, a placebo run-in period was implemented in the present study to stratify patients into 2 groups (placebo responders and placebo non-responders). During the placebo run-in period patients were not informed as to whether they were injected with BOTOX® or placebo. Furthermore, the study protocol was amended to include 3 double-blinded treatment cycles since, based on clinicians' clinical experience multiple treatments are needed to demonstrate benefit from this treatment. Treatment of other conditions such as spasticity and glabellar lines have shown an increased benefit in patients upon repeated injections with BOTOX®. In addition, it was anticipated that the placebo response would stabilize or diminish over time and multiple treatments.

Efficacy criteria were as follows. For the primary variable, a difference of 3 headache-free days between BOTOX® and placebo in the mean change from baseline in the frequency of headache-free days per month at Day 180 was considered clinically significant.

Injections and evaluations were to be performed by the same investigator throughout the study whenever possible. If it was not possible to use the same investigator to follow a given patient, then injections and evaluations were to overlap between the investigators for at least 1 visit whenever possible.

The clinical hypotheses for this study were that BOTOX® was more effective than placebo, as measured by the difference between groups in the change from baseline in the frequency of headache-free days per month, and that BOTOX® had an acceptable safety profile.

In this study several additional supplemental analyses were conducted after database lock to further understand and evaluate the effects of BOTOX® treatment. Many of these analyses were based on the updated information on the classification of headaches and a better understanding/definition of concomitant medications used by headache patients provided in the International Classification of Headache Disorders (ICHD) (Headache Classification Subcommittee of the IHS, 2004).

All patients enrolled in this study met at least the following inclusion criteria:
Male or female, 18 to 65 years old
Primary headache disorder with 16 headache days per month by history and confirmed by diary during baseline, which could include any combination of migraines with or without aura, episodic/chronic tension-type headaches, and/or migrainous headaches (as defined by 1988 IHS criteria) (Headache Classification Subcommittee of the IHS, 1988)
Willing and able to give written informed consent
Stable medical condition Stable chronic medications, if any, including non-acute, prophylactic migraine medications, for at least 3 months immediately prior to Day −60

Willing and able to stay on current medications during the course of the study

Willing and able to complete the entire course of the study and to comply with study instructions, including diary phone system.

The patients included in this study were suitable for the study purposes as their diagnosis met the definition of headache as outlined by the IHS (Headache Classification Committee of the IHS, 1988) and their baseline headache characteristics were sufficient to detect a change following treatment.

A dose range of units to be injected into each muscle area was defined, except for the occipitalis muscle where the dosage was fixed. The number of injection sites (total of 23 to 58 injection sites) within each specified muscle area (6 to 7 muscle areas) and dose injected (105 U to 260 U) was determined by the physician based on the pain distribution pattern and the severity of pain in the particular muscle area. Patients were to be injected in a minimum of 6 muscle areas, which included the frontal/glabellar, occipitalis, temporalis, semispinalis, splenius capitis, and trapezius muscles, as specified in Table 1 and FIG. 13. It was optional to inject the masseter muscle. Patients were to be injected with the same dose and in the same muscle areas and sites for treatments 1, 2, 3, and 4. Whenever possible, treatments for each patient were to be performed by the same physician throughout the study.

TABLE 1

Study Medication Dose and Injection Sites

| Muscle Area | Number of Units [a] | Bilateral Injection | Total Dose (U) |
|---|---|---|---|
| Frontal/Glabellar | 25-40 | No | 25-40 |
| Occipitalis | 10 | Yes | 20 |
| Temporalis | 10-25 | Yes | 20-50 |
| Masseter (optional) | 0-25 | Yes | 0-50 |
| Trapezius | 10-30 | Yes | 20-60 |
| Semispinalis | 5-10 | Yes | 10-20 |
| Splenius capitis | 5-10 | Yes | 10-20 |
| Total Dose Range | | | 105-260 |

Note:
Patients were injected with BOTOX ® or placebo in the specified muscles with doses determined by the investigator.
[a] Patients randomized to the placebo group received 0 U of BOTOX ®.

Each vial of BOTOX® (Allergan, Irvine, Calif.) contained 100 U of *Clostridium botulinum* toxin type A, 0.5 mg albumin (human), and 0.9 mg sodium chloride in a sterile, vacuum-dried form without a preservative. One U corresponds to the calculated median lethal intraperitoneal dose ($LD_{50}$) in mice. Each vial of placebo contained 0.9 mg sodium chloride in a sterile, vacuum-dried form without a preservative.

The vials were stored in a freezer between −20° C. and −5° C. before use. Directions for reconstitution with the diluent, 0.9% sterile saline (without preservatives), for injection were provided in the protocol. Each vial of BOTOX® or placebo was reconstituted with 2.0 mL of saline per vial for a concentration of 50 U/mL. An individual with no other study involvement reconstituted the study medication and filled the syringes. Reconstituted study medication that was not used immediately was to be stored in a refrigerator (2° C. to 8° C.) for no more than 4 hours.

A screening number was assigned to each patient at Day −60 to be used as patient identification for the electronic diary and on all documentation until Day 0. At Day 0, following the placebo run-in period, patients were classified as placebo responders if they reported <16 headache days or a ≥30% decrease in the frequency of headache days based on the diary information collected during the placebo run-in period. All other patients were classified as placebo non-responders. Using a stratified randomization, patients were then randomized within each stratum (placebo non-responder or placebo responder) to Treatment 2 (BOTOX® or placebo). The patient number assigned at Day 0 was provided to the site via a central validated Interactive Voice Response System (IVRS) randomization. This patient number was used on all subsequent documentation.

Randomization schedules were generated by using procedures developed and validated at Allergan (PLAN procedure in SAS® software, version 8.2). Patients were randomized to receive BOTOX® or placebo in a ratio of 1:1 in blocks of 4.

The randomization number assigned the patient to receive either BOTOX® (not a specific dose level) or placebo. The independent staff person (who did not know the identity of the treatment) reconstituted 3 vials of study medication and drew the study drug into the syringes for administration, even if the total dose for a patient was only going to require 2 vials. The syringes were then given to the investigator for injection.

In this study, in contrast to the fixed site/fixed dosage treatment approach used in previous studies, physicians were allowed to use a more individualized or patient-tailored treatment approach. Specifically, the number of injection sites (23 to 58 injection sites) within each specified muscle area (6 to 7 muscle areas) and dose injected (total dose of 105 to 260 U) was determined by the physician based on the patient's usual pain distribution pattern and the severity of pain in the particular muscle area. Total dose levels used were higher than those used in previous studies since more units were injected and additional muscles were added (posterior pericranial and neck muscles trapezius, semispinalis, and splenius capitis muscles). Such an approach was anticipated to more closely approximate what is reported in clinical practice. The choice of the higher doses used in this study was further supported by the results of earlier studies in which BOTOX® at doses of up to 360 U was found to be safe and effective in the treatment of patients with cervical dystonia.

As this study was ongoing information gathered from clinical experts and reports within the literature (eg, Troost 2004) pointed to the fact that it may take several treatment cycles to observe the clinical benefit of BOTOX®. With this in mind, the protocols were amended to include a total of 3 treatment cycles (following the placebo run-in) and the primary endpoint was changed to Day 180 in the placebo non-responder stratum. By the time these amendments were put in place, a significant number of subjects had exited the original study at the planned Day 120 time point. Therefore, enrollment was extended to ensure that at least 90 placebo non-responder patients (45 per treatment group) were available for the Day 180 analysis.

Based on the learnings of the early Phase 2 studies it was thought that a dosing interval of every 4 months may be too long. Additionally, treatment intervals of 3 months for other BOTOX® muscle-related indications has been shown to be optimal. Therefore, in the current studies the treatment cycles were shortened to every 3 months. A total of 3 double-blind treatment cycles were included because, based on physicians' clinical experience, it was anticipated that multiple treatments would be needed to demonstrate benefit for this treatment. This hypothesis was supported by spasticity studies and glabellar lines studies in which an increased benefit was observed in patients upon repeated injections with BOTOX®.

The placebo run-in was a single-masked treatment whereby the investigator, but not the patient, knew that the treatment administered was to be placebo. Starting at Day 0, this was a double-blind study and neither the investigator nor the patient was to know which treatment was to be administered at Day 0, Day 90, and Day 180. To maintain this blinding, an individual, with no other study responsibilities, reconstituted the study medication and filled the syringes for injection. Treatment blinding was also protected by not describing the randomization block size for the study.

If necessary for the safety and proper treatment of the patient, the investigator could have unblinded the patient's treatment assignment to determine which treatment the patient had received and institute appropriate follow-up care.

The use of any concurrent medication (eg, prescription or over-the-counter, including herbal remedies) was recorded on the patient's CRF along with the reason the medication was taken. In addition, medications that the patient had taken for treatment of his or her headaches since 7 days prior to Day −60 were recorded on the appropriate medication CRF. During the study, the patient was to report any use of concomitant medication for headache treatment using the electronic telephone daily diary.

Patients taking concurrent therapies were to maintain a stable dose and dose regimen during the study, particularly with regard to the use of non-acute, prophylactic migraine medications. Medications that were considered necessary for the patient's welfare could be given at the discretion of the investigator. The administration of all medications was to be reported on the CRFs.

During the course of the study, patients were not to take or receive aminoglycoside antibiotics, cholinergic antagonists, curare-like agents, or agents that might interfere with neuromuscular function. The occasional use of muscle relaxants was permissible at the discretion of the investigator. However, patients were not to take muscle relaxants on a chronic basis in the 3 months prior to study entry and/or during the study. Lastly, patients were not to change their chronic medications during the study unless it was medically necessary.

The decision to administer a prohibited medication/treatment was to be done with the safety of the study participant as the primary consideration. The investigator administered study medication to each patient by intramuscular injection.

Efficacy Measures

Efficacy measures were variables derived from information recorded by patients for the duration of the study using a validated electronic headache diary using a telephone interactive voice response system (IVRS) and the patient's global assessment of response to treatment obtained from CRFs. Electronic diaries were to be completed on a daily basis throughout the study. Patients recorded start/stop times of headaches, maximum and average severity of headaches, location and type of headache pain, effect on physical activity, presence of aura, presence of associated symptoms of headaches (nausea, vomiting, photo/phonophobia), and headache medications and doses used.

The primary efficacy measure was the change from baseline in the frequency of headache-free days in a 30-day period. The primary visit for determination of efficacy was Day 180, with the evaluation reflecting the prior 30-day period. Baseline for the efficacy measures was defined as the frequency of headache-free days during the first 30-days of the screening period. A difference of 3 headache-free days between BOTOX® and placebo in the mean change from baseline in the frequency of headache-free days per 30-day period at Day 180 was considered clinically significant.

The secondary efficacy measure was the proportion of patients with a decrease from baseline of 50% or more in the frequency of headache days per 30-day period at Day 180.

Other efficacy variables included the following:
proportion of patients with a decrease from baseline of 50% or more in the frequency of headaches per 30-day period
frequency of headaches of any severity (per 30-day period)
frequency of migraine headaches of any severity (per 30-day period)
proportion of patients with a decrease from baseline of 50% or more in the frequency of migraine headaches per 30-day period
proportion of patients with a decrease from baseline of 2 or more migraine headaches per 30-day period
moderate to severe migraine headache frequency (per 30-day period)
patient's global assessment of response to treatment from baseline, as follows:
−4=very marked worsening (about 100% worse or greater)
−3=marked worsening (about 75% worse)
−2=moderate worsening (about 50% worse)
−1=slight worsening (about 25% worse)
0=unchanged
+1=slight improvement (about 25% improvement)
+2=moderate improvement (about 50% improvement)
+3=marked improvement (about 75% improvement)
+4=clearance of signs and symptoms (about 100% improvement)
number of days per 30-day period with non-migraine headaches
maximum and average headache severity (none, mild, moderate, severe)
number of days that acute headache medication was used during the study
number of uses (intakes) of acute headache mediation during the study Other variables included the following:
Treatment Assessment Questionnaire: This questionnaire was designed to collect information from the patients regarding the treatment they thought they had received (BOTOX® or placebo). The questionnaire was administered on Day 90 (asking patients to indicate what treatment they thought they had received at Day −30 and at Day 0), Day 180 (asking patients to indicate what treatment they thought they had received at Day 90), and Day 270 or when patients exited the study (asking patients to indicate what treatment they thought they had received at Day −180).

Pain Diagram: Patients completed a pain diagram at baseline and exit to illustrate the muscle areas where their headache originated and where it ended.

Headache Count Recall: Patients reported how many headaches they thought they had experienced in the last 30 days at every visit starting at Day 30. This information was to be used as backup data in the event that the electronic diary data were unavailable.

Health Outcomes Measures: The questionnaires were given to patients to complete in as quiet an area as possible prior to any queries regarding their health or condition and prior to any study procedures being performed. Patients were instructed to initial and date the last page of each questionnaire in the space provided at the time of completion. Study site personnel reviewed the questionnaires to assure completeness and requested that patients complete any unanswered questions if unintentionally left blank.

Migraine Disability Assessment (MIDAS)

The MIDAS was administered at Days −60, 90, 180 and 270. The questionnaire collected information on the effect of headaches on productivity and activity over the previous 3-month period.

Headache Pain-Specific Quality of Life Questionnaire

This questionnaire was administered at Days −60, 0, 90, 180 and 270. This series of questions was originally adapted from the Medical Outcomes Trust Patient Assessment Questionnaire (Stewart et al, 1992). These questions previously have been used with migraine patients (referring to pain, not migraine pain specifically) to assess how much pain interfered with four domains of a patient's life (i.e., daily activities, emotional health, physical health, and work) over a 4-week period (Solomon et al, 1995). The questions were measured on a 5-point scale (not at all, a little, moderately, quite a bit, extremely).

SF-36 Health Survey

This survey was administered at Days −60, 0, 90, 180 and 270. The SF-36 is a general health-related quality of life questionnaire, containing 8 domains; Physical Functioning, Role Physical, Bodily Pain, General Health, Vitality, Social Functioning, Role Emotional, and Mental Health. The SF-36 may be reported using the domains or the 2 summary scales (Physical Component Scale and Mental Component Scale).

Headache Impact Questionnaire (HIQ)

The HIQ Version 3.0.1 is designed to collect information from patients on how their migraines may affect various aspects of their life. Data were collected in 2 sections:

Resource Utilization: Patients reported the frequency of resources utilized due to migraine symptoms and treatments (eg, frequency of doctor visits, emergency room visits, and hospitalization). Resource utilization was assessed at Day −60 only.

Patient Satisfaction: Patients rated their satisfaction with various aspects of treatment (i.e., overall effectiveness of acute and prophylactic medications, effect of treatments on frequency and severity of symptoms, ability to avoid and manage symptoms, and amount spent on treatments) on a 5-point scale (very satisfied, somewhat satisfied, neutral, somewhat dissatisfied, very dissatisfied). Satisfaction was assessed at Days −60, 0, 90, 180, and 270 or exit.

Primary Chronic Daily Headache Assessment: On Day 180, the investigator indicated the predominant diagnosis for the patient by choosing 1 of 4 types of primary chronic daily headache experienced by the patient (i.e., transformed migraine, chronic tension-type headache, new daily persistent headache, hemicrania continua) using the Silberstein diagnostic criteria for chronic daily headache subtypes (Silberstein and Lipton, 2001).

Schedule of Assessments

The frequency and timing of study visits and measurements are outlined in Table 2. Additional examinations were performed as necessary to ensure the safety and well-being of patients during the study.

TABLE 2

Schedule of Assessments

|  | Visit 1 (Baseline Period) Day −60 | Visit 2 (Placebo Run-In/ Treatment 1) Day −30 | Visit 3 (Randomization/ Treatment 2) Day 0 | Visit 4 Day 30 | Visit 5 Day 60 | Visit 6 (Treatment 3) Day 90 | Visit 7 Day 120 | Visit 8 Day 150 | Visit 9 (Treatment 4) Day 180 | Visit 10 Day 210 | Visit 11 Day 240 | Visit 12 (Exit) Day 270 |
|---|---|---|---|---|---|---|---|---|---|---|---|---|
| View Video/Obtain Informed Consent | √ | | | | | | | | | | | |
| Inclusion/Exclusion Criteria | √ | √ | √ | | | | | | | | | |
| Review Medical and Medication History | √ | √ | √ | | | | | | | | | |
| Physical Examination | √ | | | | | | | | | | | √ |
| Vital Signs | √ | √ | √ | √ | √ | √ | √ | √ | √ | √ | √ | √ |
| Headache Diary Instructions and Review | √ | √ | √ | √ | √ | √ | √ | √ | √ | √ | √ | |
| Injection of Study Medication | | √ | √ | | | √ | | | √ | | | |
| Patient Global Assessment | | | √ | √ | √ | √ | √ | √ | √ | √ | √ | √ |
| Pain Diagram | √ | | | | | | | | | | | √ |
| Headache Count Recall | | | | √ | √ | √ | √ | √ | √ | √ | √ | √ |
| Beck Depression Inventory | √ | | | | | | | | | | | |
| Primary Chronic Headache Assessment | | | | | | | | | √ | | | |
| Treatment Assessment Questionnaire | | | | | | √ | | | √ | | | √ |
| MIDAS | √ | | | | | √ | | | √ | | | √ |
| Headache-Pain Specific Quality of Life Questionnaire | √ | | √ | | | √ | | | √ | | | √ |
| Headache Impact Questionnaire | √ | | √ | | | √ | | | √ | | | √ |
| SF-36 Health Survey | √ | | √ | | | √ | | | √ | | | √ |
| Medical Events | √ | √ | √ | | | | | | | | | |

TABLE 2-continued

Schedule of Assessments

| | Visit 1 (Baseline Period) Day -60 | Visit 2 (Placebo Run-In/ Treatment 1) Day -30 | Visit 3 (Randomi- zation/ Treatment 2) Day 0 | Visit 4 Day 30 | Visit 5 Day 60 | Visit 6 (Treat- ment 3) Day 90 | Visit 7 Day 120 | Visit 8 Day 150 | Visit 9 (Treat- ment 4) Day 180 | Visit 10 Day 210 | Visit 11 Day 240 | Visit 12 (Exit) Day 270 |
|---|---|---|---|---|---|---|---|---|---|---|---|---|
| Adverse Events | | | √ | √ | √ | √ | √ | √ | √ | √ | √ | √ |
| Toxin Neutralizing Antibody Titer Blood Draw | √ | | | | | √ | | | √ | | | √ |
| CBC/Blood Chemistry | √ | | | | | | | | | | | √ |
| Urine Pregnancy Test | | √ | √ | | | √ | | | √ | | | √ |
| Menstrual Cycle Data | √ | √ | √ | √ | √ | √ | √ | √ | √ | √ | √ | √ |

Appropriateness of Measurements

The efficacy measurements used in this study have been utilized in other studies of headache prophylaxis treatments (including BOTOX®) and were considered to be appropriate for this study in CDH patients. The assessment of safety by adverse events, vital signs, and clinical laboratory tests is standard practice in Phase 2 studies.

Primary Efficacy Variable(s)

The primary endpoint was the change from baseline in the frequency of headache-free days in a 30-day period the placebo non-responder stratum Day 180.

Statistical Analysis

The "as-treated" population for both the safety and efficacy analyses included all patients treated with the second injection at Day 0 (randomization/Treatment 2), regardless of subsequent injections. For comparisons of all variables, patients who were randomized and treated were analyzed according to the treatment they received at the second injection (i.e., Day 0/Treatment 2). They were analyzed in the responder/non-responder stratum indicated by baseline and placebo run-in data, regardless of which stratum they were assigned to during randomization.

The primary efficacy variable was the change in the frequency of headache-free days from a 30-day baseline period (Day –60 to Day –31). Headache-free days in each 30-day period were determined from data recorded in the telephone electronic diary. Data recorded in the diaries included headache start date and time and headache stop date and time, and the following headache characteristics: usual headache pain (mild, moderate, severe); worst headache pain (mild, moderate, severe); side of the head (unilateral/bilateral); type of pain (pulsating/throbbing or pressing/squeezing); and effect of physical activity on pain (worse, not worse). It also included headache symptoms: aura (yes or no); interference of activities (yes or no); and other symptoms (nausea, vomiting, sensitivity to light [photophobia], sensitivity to noise [phonophobia]). The diary data also included acute medication taken for the headache (yes or no) and the name and dose of the medication.

A headache episode was determined by the recording in the diary of headache start and/or stop times and/or headache characteristics, headache symptoms and/or medications taken for headaches. To calculate the duration of headaches, missing start and/or stop times were estimated as follows:

If a start time was recorded with no corresponding stop time, the stop time was set as 6 AM the following day, following the last contiguous recording of any headache characteristics, headache symptoms, or use of headache medication.

If a stop time was recorded with no corresponding start time, the start time was set as 6 AM the same day. If the stop time preceded the start time (i.e., stop time before 6 AM), the stop date was reset to the day after the start date.

If a headache was recorded with neither a start time nor a stop time, the start and stop times were set according to the preceding 2 rules. Such a headache was indicated by the recording of any of the headache characteristics, headache symptoms, or use of headache medications.

For migraine headaches, an overriding rule was that if for 2 consecutive migraine headaches there was less than 24 hours between the stop time of the first headache and the start time of the second headache, they were considered to be 1 continuous migraine headache.

A headache day was defined as the occurrence of a headache episode in the 24-hour period from midnight (inclusive) at the start of the day to midnight (not inclusive) at the end of the day, and did not depend on the frequency of headache episodes during that day. The counting of headache days (and thus, headache-free days) was done independent of the above 24-hour rule for migraines.

A headache-free day was defined as a day that was not a headache day. If a continuing patient had diary data for a given day that was missing and remained missing after implementation of the missing headache time rules given above, it was assumed to be a headache-free day. If a patient recorded diary data at least 10 days but less than 30 days into a 30-day study period, the frequency of headache-free days for the 30-day period was prorated accordingly and rounded to a whole number. For example, if a patient's 'baseline' period was 26 days, the frequency of headache-free days was multiplied by 30/26. If a patient's recorded diary data extended less than 10 days into a 30-day period, the patient was not included in the summary tables for that 30-day period. If the baseline period between the screening visit and the placebo run-in injection exceeded 30 days, the baseline period only included the first 30 days. The same conventions applied to other 30-day periods.

The primary efficacy variable was the change from baseline in the frequency of headache-free days in a 30-day period. The primary assessment time was Day 180. The primary interest was in the comparison of BOTOX® and placebo in the non-responder stratum. The primary analysis used "observed" data, as modified by the above missing headache time rules and rules for prorating the frequency of headache days.

The primary null hypothesis was that BOTOX® treatment and placebo were equally effective as measured by the change in frequency of headache-free days in the 30-day period ending at Day 180 in the non-responder stratum. The 2-sided alternative hypothesis was that BOTOX® and placebo were not equally effective. Analogous hypotheses applied to other efficacy variables.

All hypothesis tests were 2-sided. For the interim analysis at Day 90, statistical significance for the primary variable was declared only for a p-value <0.005. Multiple comparison adjustments were made by using the O'Brien-Fleming group sequential method to set the significance level at 0.048 for the primary analysis at Day 180. No adjustments for multiplicity were made for the exploratory final analysis at Day 270. All other hypothesis tests used a type-I error of alpha=0.05 to determine statistical significance, except that treatment-by-subgroup interactions were examined at the 0.10 level.

For the frequency of headache-free days at baseline and its change from baseline in the non-responder stratum, comparisons between treatment groups were done with the Wilcoxon rank-sum test (Siegel, 1956). If there had been significant baseline differences between treatments in the primary variable, the baseline value of the variable would have been included as a covariate in an analysis of covariance of the ranks of the variable.

To justify the pooling of data over multiple clinical sites, an examination was made of treatment-by-clinical site interaction effects in the analysis of the primary efficacy variable (change from baseline in the frequency of headache-free days per 30-day period). This analysis was performed using an analysis of variance (with type III sums of squares) modeling response as a function of clinical site, treatment, and their interaction. In this analysis, clinical sites were pooled (as a pseudo center) if they had fewer than 6 patients in either of the responder or non-responder stratum for the final 30-day period of the analysis (Days 90, 180 or 270). All small centers were pooled regardless of the size of the resulting pooled center. However, in some of the exploratory supplemental by-investigator tables, small centers were excluded from analysis.

Similar analyses to evaluate treatment-by-subgroup interactions were performed for age, gender, race, time since disease onset, chronic daily headache subtype, baseline menstrual headache, baseline MIDAS total days score, baseline prophylactic treatment, baseline beta blocker use, baseline calcium channel blocker use, baseline anticonvulsant use, and baseline antidepressant use.

Comparison of the treatment groups in the responder stratum was a secondary objective of the analysis. Supplemental analyses included analyses of data pooled across strata, and with and without concomitant headache prophylaxis treatment.

Secondary endpoints included the changes from baseline to other time points (Days 30, 60, 90, 120, 150, 210, 240, and 270) in the frequency of headache-free days per 30-day period in each stratum. The statistical methods used to analyze these other time points were the same as for the primary time point.

In addition to the "observed cases" analyses, supplemental analyses were performed using imputed data for missing values. Detailed methodology regarding how missing data were imputed is included in Section 5.3.1 of the analyses plan (Appendix 16.1.9).

There was 1 secondary efficacy variable to be summarized for each 30-day diary period associated with each visit, namely, the proportion of patients with a decrease from baseline of 50% or more headache days per 30-day period for the placebo non-responder stratum at Day 180. This variable was analyzed using the observed data with Pearson's chi square test. For this secondary efficacy variable, as for the primary variable, supplemental analyses using imputed data for missing values were performed. Comparison of the treatment groups in the responder stratum was a secondary objective of the analysis. Supplemental analyses included analyses of data pooled across strata, and subgroup by treatment interaction, including with and without concomitant headache prophylaxis treatment.

Other continuous protocol-specified efficacy variables to be summarized for each 30-day period included the following: frequency of headaches of any severity, frequency of migraine headaches of any severity, frequency of moderate to severe migraine headaches (as determined by the "worst" headache severity rather than the "usual" headache severity), worst headache severity (mild, moderate severe), usual headache severity (mild, moderate severe), number of days with non-migraine headaches, number of days with use of acute analgesic headache medication, and patient's global assessment of response to treatment. The change from baseline for continuous variables was analyzed as described for ordinal variables.

Analyses also were performed for the following protocol-specified efficacy variables for each 30-day period: proportion of patients with a decrease from baseline of 50% or more headaches, proportion of patients with a decrease from baseline of 50% or more migraine headaches, and proportion of patients with a decrease from baseline of 2 or more migraine headaches. As in the analysis of a decrease from baseline of at least 50% in the frequency of headaches, separate analyses also were performed for decreases of 30%, 40%, 60%, 70%, 80%, 90% and 100% for headaches, headache day, migraines, and moderate or worse migraines.

In addition, analyses were performed of the proportions of patients with a sustained 50% decrease from baseline in the frequency of headache days. Within a treatment cycle, a patient was considered to be a sustained responder if the patient had at least a 50% decrease during 2 consecutive 30-day periods within the cycle. A sustained decrease over the study meant there was a sustained decrease within each post-randomization treatment cycle.

The analyses of the proportions of patients were the same as those described for nominal variables.

Analyses to evaluate treatment-by-subgroup interactions were performed for frequency of headache-free days, days of headache, frequency of headaches, days of migraine, frequency of migraines, days of migraines or probable migraines, frequency of migraines or probable migraines, days of headache (no prophylaxis group), frequency of headaches by baseline prophylaxis group, days of migraines or probable migraines (no prophylaxis group), frequency of migraines or probable migraines (no prophylaxis group), days with acute analgesic headache medication use (no prophylaxis group), and uses of acute analgesic headache medication (no prophylaxis group). Additional post hoc analyses were performed as described below.

To detect a difference between treatments of 3.0 or more headache-free days in the mean change from baseline, approximately 45 patients per treatment were necessary in the placebo non-responder stratum. This estimate assumed the usual 2-sided error level of alpha=0.05 and 80% power. It also took into account a standard deviation of 5 units for headache-free days. The calculation was performed by using nQuery Advisor (Elashoff, 2000).

Approximately 494 patients were to be screened at 7 to 15 investigative sites to achieve a minimum of 90 patients (45 patients per treatment group) who would receive a third treatment (Day 180) in the placebo non-responder stratum.

Of the 494 patients, it was estimated that approximately 40% would drop out from Day −60 to Day 0, and 15% would drop out between Day 0 and Day 90. The patient drop out rate between Day 90 and Day 180 also was expected to be 15%. Using these dropout rates, it was estimated that with 494 patients screened at Day −60, 296 patients would remain in the study at Day 0, 252 patients at Day 90, and 129 patients at Day 180. Of the patients remaining at Day 180, it was expected that 90 would be placebo non-responders, with 45 patients in each treatment group. The remaining 39 patients at Day 180 were expected to be placebo-responders.

Of the 571 patients screened and assessed over the Day −60 to Day −30 baseline period, 355 were enrolled/randomized at Day 0. At the end of the run-in period (Day 0), 279 patients were classified as placebo non-responders and 76 patients as placebo responders. Subsequently patients were randomized within each stratum (placebo non-responders and placebo responders) to receive either BOTOX® or placebo treatment. Within the placebo non-responder stratum, 134 patients received BOTOX® and 145 patients received placebo. Within the placebo responder stratum, 39 patients received BOTOX® and 37 patients received placebo. A total of 76.9% of patients ($273/355$) completed the study, including 132 patients who completed the original protocol requiring only 1 post-randomization treatment. Of the patients who discontinued early (22.8% [$81/355$]): 5.1% ($18/355$) for lack of efficacy, 1.4% ($5/355$) for adverse events, 0.3% ($1/355$) for inability to follow study instructions, 1.1% ($4/355$) for personal reasons, and 2.8% ($10/355$) were lost to follow up.

All safety and efficacy analyses were performed using the "as-treated" population, consisting of all patients who received treatment at Day 0 (Treatment 2). Patients were analyzed according to the treatment actually received (Day 0), not the treatment they were randomized to receive. The "as-treated" population included all 355 randomized patients.

There were no significant differences between treatment groups in demographic characteristics. Overall, patients were 19 to 65 years of age (mean, 43.5 years), 84.5% ($300/355$) were female, and 87.9% ($312/355$) were Caucasian.

There were no significant differences between treatment groups in baseline characteristics (Table 3). The mean time from onset of chronic daily headaches was 14.5 years and the mean age at onset was 28.4 years. The average baseline MIDAS score was 57.6 (indicating severe disability) and Beck Depression Inventory score was 7.8 (indicating no clinical depression). The headache diagnosis subtype assigned by the investigator was not recorded for approximately half the patients, since this was part of a protocol amendment initiated midway through the study. In those for whom it was recorded, the most frequent subtype was transformed migraine. Based on telephone data, headache prophylactic treatment was used by 35.8% ($127/355$) of patients. No patients had reported predominantly menstrually-associated headaches.

TABLE 3

Baseline Characteristics (As-Treated Population)

| Baseline Characteristic | BOTOX® 105 U to 260 U (N = 173) | Placebo (N = 182) | Total (N = 355) | P-value |
|---|---|---|---|---|
| Years since onset, mean (SD) | 14.8 (12.4) | 14.2 (12.5) | 14.5 (12.4) | 0.655 [a] |
| Age at onset, mean years (SD) | 27.5 (12.3) | 29.2 (13.6) | 28.4 (13.0) | 0.301 [a] |
| Frequency of migraines/probable migraines per 30-day period at baseline | 11.2 (6.6) | 10.8 (7.9) | 11.0 (7.3) | 0.274 |
| Use of prophylactic treatment, n (%) | 56 (32.4) | 71 (39.0) | 127 (35.8) | 0.192 [b] |
| Experience menstrual headaches, n (%) | 0 (0.0) | 0 (0.0) | 0 (0.0) | >0.999 [b] |
| Baseline MIDAS score, mean (SD) | 55.3 (49.6) | 59.8 (59.6) | 57.6 (55.0) | 0.997 [a] |
| Baseline Beck Depression Inventory score, mean (SD) | 7.8 (6.9) | 7.9 (6.8) | 7.8 (6.9) | 0.847 [a] |
| Mean total dose for the second treatment cycle | 190.8 U | NA | NA | NA |

SD = standard deviation, NA = not applicable, MIDAS = Migraine Disability Assessment.
[a] P-values for treatment comparisons from the Wilcoxon rank-sum test.
[b] P-values for treatment comparisons from Pearson's chi-square or Fisher's exact tests.

The most common locations where head pain historically started and ended, as reported by patients at baseline, are presented in Table 4.

TABLE 4

Location where Headache Pain Historically Starts and Ends Reported at Baseline (Number (%) of Patients)

| Location | BOTOX® 105 U to 260 U (N = 173) | Placebo (N = 182) | Total (N = 355) | P-value |
|---|---|---|---|---|
| Historical Location Where Pain Starts | | | | |
| Frontal/glabellar | 125 (72.7) | 140 (76.9) | 265 (74.9) | 0.357 |
| Temporalis | 100 (58.1) | 114 (62.6) | 214 (60.5) | 0.387 |
| Occipitalis | 80 (46.5) | 85 (46.7) | 165 (46.6) | 0.971 |

TABLE 4-continued

Location where Headache Pain Historically Starts and
Ends Reported at Baseline (Number (%) of Patients)

| Location | BOTOX® 105 U to 260 U (N = 173) | Placebo (N = 182) | Total (N = 355) | P-value |
|---|---|---|---|---|
| Historical Location Where Pain Ends | | | | |
| Frontal/glabellar | 123 (71.9) | 145 (79.7) | 268 (75.9) | 0.089 |
| Temporal is | 98 (57.3) | 113 (62.1) | 211 (59.8) | 0.360 |
| Occipitalis | 97 (56.7) | 111 (61.0) | 208 (58.9) | 0.416 |

Other than headache, the most common medical history findings recorded at the baseline visit for all patients were migraine (61.4% [218/355]), gynecologic disorders (58.7% of females [176/300]), musculoskeletal disorders (44.8% [159/355]), psychiatric disorders (43.9% [156/355]), gastrointestinal disorders (34.1% [121/355]), ear, nose, and throat disorders (33.5% [119/355]), allergies (31.8% [113/355]), and drug sensitivities (23.7% [84/355]) (Table 14.1-4.1). There were no statistically significant differences in medical histories between the treatment groups.

Use of prophylactic headache medication prior to study entry was reported at the baseline visit for 32.4% (56/173) of the patients treated with BOTOX® and 39.0% (71/182) treated with placebo (Table 14.1-3.4) Acute analgesic medication overuse (≥15 days and ≥2 days/week per 30-day period) was seen in 52.6% (91/173) of the patients treated with BOTOX® and 42.3% (77/182) of the patients treated with placebo (Table 14.2-76.3). There were no statistically significant differences between the treatment groups.

The protocol specified a secondary efficacy variable as the number of patients with a 50% or more decrease from baseline in headache days per 30-day period with an associated primary time point (Day 180) and group (placebo non-responders). Several other protocol-specified efficacy variables were examined to determine which patient population was most responsive to treatment with BOTOX® and which efficacy variable(s) best demonstrated the efficacy of BOTOX® over placebo (summarized for each 30-day period).

Secondary Endpoint: Decrease from Baseline of 50% or More Headache Days Per 30-Day Period In the placebo non-responder stratum, a significantly higher (p=0.027) percentage of BOTOX® compared with placebo patients had at least a 50% decrease from baseline in the frequency of headache days per 30-day period at Day 180 (32.7% versus 15.0%).

Other Secondary and Exploratory Analyses

In the analyses of the frequency of headaches per 30-day period, a statistically significant change in the frequency of headaches per 30-day period was observed at Days 30, 60, 150, 180, 210, and 240 for placebo non-responders and at Day 180 for placebo responders (Table 5). FIG. 14 presents the mean baseline and the mean changes from baseline in the frequency of headaches per 30-day period for placebo non-responders and placebo responders.

TABLE 5

Mean (Standard Deviation) at Baseline and Change from Baseline in the Frequency of Headaches per 30-Day Period for Placebo Non-responders and Placebo Responders

| | Placebo Non-Responders | | | Placebo Responders | | |
|---|---|---|---|---|---|---|
| Time Period | BOTOX® (N = 134) | Placebo (N = 145) | p-value [a] | BOTOX® (N = 39) | Placebo (N = 37) | p-value [a] |
| Baseline | 13.1 (8.4) | 12.8 (9.0) | 0.780 | 15.0 (5.0) | 12.3 (4.9) | 0.021 |
| Treatment 1: Placebo (followed by a 30-day run-in period) | | | | | | |
| Treatment 2 | | | | | | |
| Day 30 | −3.3 (5.0) | −2.0 (4.8) | 0.028 | −6.7 (6.5) | −5.2 (4.7) | 0.705 |
| Day 60 | −4.1 (5.5) | −2.6 (5.3) | 0.018 | −7.4 (5.7) | −5.8 (4.4) | 0.855 |
| Day 90 | −3.9 (5.6) | −3.2 (5.9) | 0.307 | −8.0 (6.3) | −5.7 (4.5) | 0.534 |
| Treatment 3 | | | | | | |
| Day 120 | −4.6 (5.2) | −3.0 (6.3) | 0.118 | −7.6 (5.2) | −5.6 (3.3) | 0.412 |
| Day 150 | −6.3 (6.0) | −3.8 (6.2) | 0.039 | −8.5 (5.3) | −6.9 (4.6) | 0.851 |
| Day 180 | −6.1 (5.5) | −3.1 (6.8) | 0.013 | −9.9 (4.9) | −5.6 (2.8) | 0.013 |
| Treatment 4 | | | | | | |
| Day 210 | −6.5 (6.9) | −3.4 (7.0) | 0.021 | −9.7 (5.8) | −6.6 (4.9) | 0.259 |
| Day 240 | −7.1 (7.3) | −4.1 (6.5) | 0.035 | −9.7 (6.1) | −8.2 (4.5) | 0.948 |
| Day 270 | −7.2 (7.4) | −4.7 (7.3) | 0.172 | −9.9 (4.7) | −7.4 (5.4) | 0.488 |

Source: Tables 14.2-12.3 and 14.2-12.4.

[a] Between treatment comparison from Wilcoxon rank-sum test.

In the analyses of other protocol-designated efficacy variables, there were statistically significant differences between BOTOX® and placebo in the placebo non-responder and placebo responder groups. Additionally, subgroups of patients were identified for which there was a consistently better response to BOTOX® than to placebo.

As a part of the process of identifying patient populations for which there was a consistent response to treatment, analyses were performed to identify significant interaction effects of treatment and various baseline patient characteristics. The placebo non-responder and placebo responder strata were pooled and the resulting data were analyzed to compare BOTOX® with placebo (pooled population). In the following sections analyses are presented only for the pooled population.

Frequency of Headaches, Pooled Population

A statistically significant change in the frequency of headaches per 30-day period was observed at multiple time points (Days 30, 60, 150, 180, 210, and 240) (Table 6). FIG. 15 presents the mean baseline and the mean changes from baseline in the frequency of headaches per 30-day period.

The analysis of frequency of headaches demonstrated statistically significant differences between BOTOX® and placebo that favored BOTOX®.

TABLE 6

Mean (Standard Deviation) at Baseline and Change from Baseline in the Frequency of Headaches per 30-Day Period; Pooled Population

| Time Period | BOTOX® N = 173 | Placebo N = 182 | p-value [a] |
|---|---|---|---|
| Baseline | 13.5 (7.7) | 12.7 (8.3) | 0.339 |
| Treatment 1: Placebo (followed by a 30-day run-in period) | | | |
| Post Placebo Run-in | −1.9 (4.7) | −1.0 (4.0) | 0.336 |
| Treatment 2 | | | |
| Day 30 | −4.1 (5.6) | −2.7 (4.9) | 0.021 |
| Day 60 | −4.8 (5.7) | −3.2 (5.3) | 0.010 |
| Day 90 | −4.9 (6.0) | −3.7 (5.7) | 0.135 |
| Treatment 3 | | | |
| Day 120 | −5.4 (5.3) | −3.6 (5.8) | 0.061 |
| Day 150 | −6.9 (5.8) | −4.6 (6.0) | 0.033 |
| Day 180 | −7.1 (5.6) | −3.7 (6.1) | 0.001 |
| Treatment 4 | | | |
| Day 210 | −7.4 (6.7) | −4.2 (6.7) | 0.005 |
| Day 240 | −7.9 (7.0) | −5.1 (6.3) | 0.035 |
| Day 270 | −8.0 (6.8) | −5.4 (7.0) | 0.080 |

[a] Between treatment comparison from Wilcoxon rank-sum test.

As seen in Table 6 and FIG. 15, the time of the first statistically significant difference between treatment groups in the frequency of headaches per 30-day period was at 30 days after the first treatment following placebo run-in. At this time point, there was a significant difference (p=0.021) between BOTOX® and placebo demonstrating a rapid onset of effect. The mean changes from baseline were −4.1 for BOTOX® and −2.7 for placebo.

The percentage of patients with at least a 50% decrease from baseline in the frequency of headaches per 30-day period was significantly greater for BOTOX® compared with placebo at Days 180 and 210 (Table 7). In the BOTOX® group, at all time points after Day 120 at least 50% of patients had at least a 50% decrease from baseline in the frequency of headaches per 30-day period.

TABLE 7

Number (Percentage) of Patients with a Decrease from Baseline of 50% or More Headaches per 30-Day Period; Pooled Population

| Time Period | BOTOX® | Placebo | p-value [a] |
|---|---|---|---|
| Treatment 1: Placebo (followed by a 30-day run-in period) | | | |
| Post Placebo Run-in | 23/173 (13.3) [b] | 20/182 (11.0) | 0.506 |
| Treatment 2 | | | |
| Day 30 | 45/172 (26.2) | 47/182 (25.8) | 0.942 |
| Day 60 | 60/164 (36.6) | 49/166 (29.5) | 0.172 |
| Day 90 | 54/149 (36.2) | 49/157 (31.2) | 0.352 |
| Treatment 3 | | | |
| Day 120 | 33/80 (41.3) | 28/82 (34.1) | 0.351 |
| Day 150 | 38/75 (50.7) | 33/80 (41.3) | 0.240 |
| Day 180 | 39/72 (54.2) | 30/79 (38.0) | 0.046 |
| Treatment 4 | | | |
| Day 210 | 40/70 (57.1) | 28/77 (36.4) | 0.012 |
| Day 240 | 39/70 (55.7) | 32/71 (45.1) | 0.206 |
| Day 270 | 40/69 (58.0) | 38/69 (55.1) | 0.731 |

[a] Between treatment comparison from Person's chi square test or Fisher's exact test.
[b] Number of patients with response/number of patients evaluated at time period (percentage).

The percentage of patients with at least a 30% decrease from baseline in the frequency of headaches per 30-day period was significantly greater for BOTOX® compared with placebo at Days 30 (47.7% versus 37.4%; p=0.050), 60 (53.0% versus 41.0%), p=0.028), 180 (73.6% versus 55.7%; p=0.022), and 210 (72.9% versus 51.9%; p=0.009 Table 14.2-15.3). In the BOTOX® group, at all time points after Day 120 at least 70% of patients had at least a 30% decrease from baseline in the frequency of headaches per 30-day period.

Table 8 presents the mean baseline and the mean changes from baseline in the frequency of headaches per 30-day period for patients who completed 2 and 3 treatment cycles after the placebo run-in period. The 138 patients (69 BOTOX®, 69 placebo) who completed 3 treatment cycles had a sustained response to treatment. Over the 270 day treatment period the response to treatment with BOTOX® generally continued to improve while the response to treatment with placebo remained relatively stable.

TABLE 8

Mean (Standard Deviation) at Baseline and Change from Baseline in the Frequency of Headaches per 30-Day Period for Patients Who Completed 2 or 3 Injection Cycles After the Placebo Run-in; Pooled Population

| Time Period | Completed 2 Treatment Cycles After Placebo Run-in | | | Completed 3 Treatment Cycles After Placebo Run-in | | |
|---|---|---|---|---|---|---|
| | BOTOX® N = 72 | Placebo N = 79 | p-value [a] | BOTOX® N = 69 | Placebo N = 69 | p-value [a] |
| Baseline | 14.3 (7.5) | 12.8 (8.3) | 0.183 | 14.4 (7.5) | 12.6 (8.1) | 0.136 |
| | Treatment 1: Placebo followed by a 30-day run-in period) | | | | | |
| | Treatment 2 | | | | | |
| Day 30 | −4.7 (5.3) | −3.4 (5.0) | 0.072 | −4.7 (5.4) | −3.4 (5.1) | 0.098 |
| Day 60 | −5.3 (5.3) | −3.5 (5.4) | 0.037 | −5.3 (5.4) | −3.7 (5.6) | 0.091 |
| Day 90 | −4.8 (5.6) | −3.5 (5.6) | 0.198 | −4.7 (5.7) | −3.4 (5.8) | 0.229 |
| | Treatment 3 | | | | | |
| Day 120 | −5.8 (5.2) | −3.6 (5.8) | 0.023 | −5.7 (5.2) | −3.6 (6.0) | 0.036 |
| Day 150 | −6.8 (5.8) | −4.5 (5.9) | 0.042 | −6.8 (5.9) | −4.5 (6.1) | 0.056 |
| Day 180 | −7.1 (5.6) | −3.7 (6.1) | 0.001 | −7.1 (5.6) | −3.7 (6.3) | 0.001 |
| | Treatment 4 | | | | | |
| Day 210 | −7.4 (6.8) | −4.2 (6.7) | 0.008 | −7.5 (6.7) | −3.9 (6.8) | 0.004 |
| Day 240 | −7.9 (7.1) | −5.1 (6.3) | 0.030 | −7.9 (7.0) | −5.0 (6.3) | 0.025 |
| Day 270 | −8.0 (6.8) | −5.4 (7.0) | 0.041 | −8.0 (6.8) | −5.4 (7.0) | 0.042 |

[a] Between treatment comparison from a Wilcoxon rank-sum test.

Table 9 presents the mean baseline and the mean changes from baseline in the number of headaches with a duration ≥4 hours and <4 hours per 30-day period. Over the 270-day treatment period, in headaches ≥4 hours in duration, the changes from baseline headache count were significantly greater for BOTOX® than for placebo at every return visit (p≤0.044; Table 14.5-325). A significant difference between the groups was not seen at any return visit for headaches <4 hours in duration.

which there were clinically meaningful differences between BOTOX® and placebo in this subpopulation subgroup included:
- A 50% reduction from baseline in the frequency of headaches per 30-day period
- A 30% reduction from baseline in the frequency of headaches per 30-day period
- Frequency of migraines or probable migraines per 30-day period

TABLE 9

Mean Baseline and Change from Baseline in the Frequency of Headaches for Headaches of a Durations >4 Hours and <4 Hours per 30-Day Period

| Time Period | Headaches of a Duration ≥4 Hours | | | Headaches of a Duration <4 Hours | | |
|---|---|---|---|---|---|---|
| | BOTOX® N = 173 | Placebo N = 182 | p-value [a] | BOTOX® N = 173 | Placebo N = 182 | p-value [a] |
| Baseline | 9.6 | 9.2 | 0.186 | 3.9 | 3.5 | 0.488 |
| | Treatment 1: Placebo (followed by a 30-day run-in period) | | | | | |
| | Treatment 2 | | | | | |
| Day 30 | −2.9 | −1.2 | 0.001 | −1.2 | −1.5 | 0.307 |
| Day 60 | −3.4 | −1.9 | 0.017 | −1.4 | −1.3 | 0.784 |
| Day 90 | −3.3 | −2.0 | 0.024 | −1.6 | −1.7 | 0.848 |
| | Treatment 3 | | | | | |
| Day 120 | −3.8 | −2.0 | 0.013 | −1.6 | −1.6 | 0.867 |
| Day 150 | −4.8 | −2.8 | 0.044 | −2.0 | −1.8 | 0.906 |
| Day 180 | −4.6 | −2.2 | 0.005 | −2.5 | −1.6 | 0.134 |
| | Treatment 4 | | | | | |
| Day 210 | −5.1 | −2.4 | 0.003 | −2.3 | −1.7 | 0.688 |
| Day 240 | −5.1 | −3.0 | 0.016 | −2.7 | −2.1 | 0.309 |
| Day 270 | −5.5 | −3.1 | 0.013 | −2.4 | −2.2 | 0.872 |

[a] Between treatment comparison from a Wilcoxon rank-sum test.

Post hoc analyses found that for the subpopulation subgroup of patients who were not using prophylactic headache medications at baseline there was greater separation and preservation of statistical significance of BOTOX® versus placebo at most timepoints in the analyses of the frequency of headaches per 30-day period. Other efficacy variables for

- Number of days and number of uses of acute analgesic headache medication per 30-day period The subpopulation subgroup of patients not using prophylactic headache medications at baseline included 67.6% ($117/173$) of the patients randomized to and treated with BOTOX® and 61.0% ($111/182$) of the patients randomized to and treated with placebo. The demographic characteristics of BOTOX® and placebo patients using and not using prophylactic headache medications at baseline are given in Table 10. For both of the subgroups of patients, there were no statistically significant differences between the 2 treatment groups with respect to their baseline characteristics, except for gender in the subgroup of patients not using prophylactic medications (p=0.025). Patients not using prophylactic headache medications at baseline compared with those who were using prophylactic headache medications were younger (mean age, 42.4 vs. 45.6; p=0.010), had an earlier age of onset of chronic daily headache (mean age, 26.9 vs. 31.1 years; p=0.005), had lower Beck Depression Inventory scores (mean score, 7.1 vs. 9.0; p=0.004), and were similar with respect to all other baseline variables.

days per 30-day period are presented in Table 11 and FIG. 16 for the populations of patients using and not using prophylactic headache medications at baseline. The types of prophylactic headache medications used at baseline included beta blockers, calcium channel blockers, anticonvulsants, and antidepressants (excluding serotonin uptake inhibitors [eg, PROZAC®] since there is no evidence of any effect in headache for this class).

For patients who were using prophylactic headache medications at baseline, the mean changes from baseline in the frequency of headaches per 30-day period were greater for BOTOX® compared with placebo at Day 120 through Day 270 by 1.0 to 2.7. The differences in the changes from baseline were statistically significantly different only at Day 180. For patients who were not using prophylactic headache medications at baseline, the mean changes from baseline

TABLE 10

Baseline Characteristics of Patients Using and Not Using Prophylactic Headache Medications at Baseline; Pooled Population

|  | Prophylactic Headache Medications at Baseline | | | | | |
|---|---|---|---|---|---|---|
|  | No | | | Yes | | |
| Baseline Characteristic | BOTOX® (N = 117) | Placebo (N = 111) | P-Value | BOTOX® (N = 56) | Placebo (N = 71) | P-Value |
| Age, mean years (SD) | 42.2 (10.4) | 42.5 (11.5) | 0.978 [a] | 44.4 (8.5) | 46.5 (10.3) | 0.232 [a] |
| Sex, n (%) | | | | | | |
| Male | 11 (9.4) | 22 (19.8) | 0.025 [b] | 11 (19.6) | 11 (15.5) | 0.540 [b] |
| Female | 106 (90.6) | 89 (80.2) | | 45 (80.4) | 60 (84.5) | |
| Race, n (%) | | | | | | |
| Caucasian | 102 (87.2) | 93 (83.8) | 0.466 [b] | 52 (92.9) | 65 (91.5) | >0.999 [b] |
| Non-Caucasian | 15 (12.8) | 18 (16.2) | | 4 (7.1) | 6 (8.5) | |
| Years since onset, mean (SD) | 15.3 (13.2) | 14.3 (12.8) | 0.656 [a] | 13.8 (10.7) | 14.2 (12.1) | 0.864 [a] |
| Age at onset, mean years (SD) | 26.2 (12.2) | 27.6 (13.1) | 0.562 [a] | 30.1 (12.1) | 31.8 (13.9) | 0.407 [a] |
| Prophylactic headache medications, n (%) | | | | | | |
| Beta blockers | NA | NA | NA | 16 (28.6) | 21 (29.6) | 0.901 |
| Calcium channel blockers | NA | NA | NA | 9 (16.1) | 18 (25.4) | 0.204 |
| Anticonvulsants | NA | NA | NA | 23 (41.1) | 27 (38.0) | 0.727 |
| Antidepressants | NA | NA | NA | 31 (55.4) | 43 (60.6) | 0.555 |
| Baseline MIDAS score, mean (SD) | 54.0 (44.4) | 55.7 (60.3) | 0.302 [a] | 58.0 (59.7) | 66.1 (58.8) | 0.264 [a] |
| Baseline Beck Depression Inventory score, mean (SD) | 6.9 (6.6) | 7.3 (7.0) | 0.945 [a] | 9.5 (7.4) | 8.6 (6.4) | 0.739 [a] |

SD = standard deviation,
NA = not applicable,
NC = not computed.
[a] P-values for treatment comparisons from the Wilcoxon rank-sum test.
[b] P-values for treatment comparisons from Pearson's chi-square or Fisher's exact tests.

Frequency of Headaches in Patients Using and not Using Prophylactic Headache Medications at Baseline The mean baseline and mean changes from baseline to each assessment time point in the frequency of headache were greater for BOTOX® compared with placebo by 2.2 to 4.2. The differences between treatment groups were either statistically significant (p≤0.032) or marginally statistically significant (p≤0.072) at all time points.

TABLE 11

Mean (Standard Deviation) at Baseline and Change from Baseline in the Frequency of Headaches per 30-Day Period by Use of Prophylactic Headache Medications at Baseline; Pooled Population

| | Use of Prophylactic Headache Medications at Baseline | | | | | |
|---|---|---|---|---|---|---|
| | Yes | | | No | | |
| Time Period | BOTOX ® N = 56 | Placebo N = 71 | p-value [a] | BOTOX ® N = 117 | Placebo N = 111 | p-value [a] |
| Baseline | 12.4 (7.5) | 12.5 (8.6) | 0.855 | 14.1 (7.9) | 12.9 (8.2) | 0.205 |
| Treatment 1: Placebo (followed by a 30-day run-in period) | | | | | | |
| Treatment 2 | | | | | | |
| Day 30 | −2.8 (4.1) | −2.8 (3.7) | 0.887 | −4.7 (6.1) | −2.5 (5.6) | 0.004 |
| Day 60 | −3.5 (4.4) | −3.5 (4.6) | 0.836 | −5.5 (6.1) | −3.0 (5.7) | 0.005 |
| Day 90 | −3.6 (5.0) | −4.8 (4.9) | 0.201 | −5.6 (6.3) | −3.0 (6.1) | 0.011 |
| Treatment 3 | | | | | | |
| Day 120 | −5.3 (4.3) | −4.0 (4.9) | 0.255 | −5.5 (6.0) | −3.3 (6.5) | 0.072 |
| Day 150 | −5.7 (5.1) | −4.7 (5.3) | 0.564 | −7.8 (6.2) | −4.5 (6.6) | 0.032 |
| Day 180 | −6.6 (5.0) | −3.9 (4.7) | 0.030 | −7.5 (6.0) | −3.6 (7.3) | 0.007 |
| Treatment 4 | | | | | | |
| Day 210 | −6.7 (5.5) | −4.7 (5.1) | 0.138 | −7.9 (7.4) | −3.7 (7.9) | 0.023 |
| Day 240 | −6.6 (6.0) | −5.0 (5.5) | 0.279 | −8.7 (7.6) | −5.1 (7.1) | 0.062 |
| Day 270 | −6.9 (6.3) | −5.2 (5.5) | 0.369 | −8.8 (7.1) | −5.6 (8.1) | 0.062 |

[a] Between treatment comparison from a Wilcoxon rank-sum test.

Compared with patients who used prophylactic headache medications at baseline, patients who did not use prophylactic headache medications at baseline had mean changes from baseline that generally were greater for BOTOX®-treated patients and smaller for placebo-treated patients.

Analyses by Type of Prophylactic Headache Medication Used at Baseline

Analyses of the frequency of headaches per 30-day period were performed for the baseline use of beta-blockers, calcium channel blockers, anticonvulsants, and antidepressants.

There were no statistically significant differences between treatment groups at any time point in the mean change from baseline in the frequency of headaches per 30-day period for patients using beta-blockers at baseline or calcium channel blockers at baseline. At baseline, 37 patients (16 BOTOX®, 21 placebo) were using beta-blockers and 27 patients (9 BOTOX®, 18 placebo) were using calcium channel blockers. The analyses of patients not using beta blockers at baseline and analyses of patients not using calcium channel blockers at baseline showed statistically significant differences between treatment groups at multiple time points that were comparable to those for the larger group of patients not using prophylactic headache medications at baseline (Table 11).

For patients using anticonvulsants at baseline (23 BOTOX®, 27 placebo) there were no statistically significant differences between treatment groups at any time point, except at Day 180 (p=0.006), in the change from baseline in the frequency of headaches per 30-day period. From Day 120 through Day 270, the mean decrease from baseline was greater for BOTOX® by 2.2 to 4.9 headaches per 30-day period. For patients not using anticonvulsants at baseline, the changes from baseline were significantly greater (p≤0.026) for BOTOX® at Days 30, 60, 180, and 210. At these time points the mean changes were greater for BOTOX® by 1.6 to 3.2 headaches per 30-day period.

For patients using antidepressants at baseline (31 BOTOX®, 43 placebo) there were no statistically significant differences between treatment groups at any time point, except at Day 210 (p=0.048), in the change from baseline in the frequency of headaches per 30-day period. From Day 120 through Day 270, the mean decrease from baseline was greater for BOTOX® by 1.6 to 3.7 headaches per 30-day period. For patients not using antidepressants at baseline, from Day 60 through Day 270, the mean decrease from baseline was greater for BOTOX® by 1.7 to 3.6 headaches per 30-day period. The changes from baseline were significantly greater (p≤0.020) for BOTOX® at Days 30, 60, and 180.

Decrease from Baseline of 50% or More Headaches Per 30-Day Period in Patients with and without Concomitant Headache Prophylaxis Using and not Using Prophylactic Headache Medications at Baseline The percentages of patients at each assessment time point with at least a 50% decrease from baseline in the frequency of headaches per 30-day period (defined as a responder) are presented in Table 12 for patients using and not using prophylactic headache medications at baseline.

For patients using prophylactic headache medications at baseline, there were no statistically significant differences between BOTOX® and placebo. For patients not using prophylactic headache medications at baseline, from Day 150 through Day 270 at least 50% of BOTOX®-treated patients were responders. The differences between BOTOX® and placebo were statistically significant at Days 150 and 210. At these time points, the response rate for BOTOX® was greater than the response rate for placebo by at least 20%.

TABLE 12

Number (Percentage) of Patients with a Decrease from Baseline of 50% or More Headaches per 30-Day Period by Use of Prophylactic Headache Medications at Baseline; Pooled Population

| | Using Prophylactic Headache Medications at Baseline | | | | | |
|---|---|---|---|---|---|---|
| | Yes | | | No | | |
| Time Period | BOTOX® N = 56 | Placebo N = 71 | p-value [a] | BOTOX® N = 117 | Placebo N = 111 | p-value [a] |
| Treatment 1: Placebo followed by a 30-day run-in period) | | | | | | |
| Post Placebo Run-in | 4/56 (7.1%) [b] | 7/71 (9.9%) | 0.754 | 19/117 (16.2%) | 13/111 (11.7%) | 0.325 |
| Treatment 2 | | | | | | |
| Day 30 | 10.56 (17.9%) | 17/71 (23.9%) | 0.405 | 35/116 (30.2%) | 30/111 (27.0%) | 0.600 |
| Day 60 | 15/54 (27.8%) | 20/66 (30.3%) | 0.762 | 45/110 (40.9%) | 29/100 (29.0%) | 0.071 |
| Day 90 | 15/53 (28.3%) | 22/63 (34.9%) | 0.446 | 39/96 (40.6%) | 27/94 (28.7%) | 0.085 |
| Treatment 3 | | | | | | |
| Day 120 | 17/34 (50.0%) | 17/39 (43.6%) | 0.584 | 16/46 (34.8%) | 11/43 (25.6%) | 0.345 |
| Day 150 | 13/30 (43.3%) | 19/38 (50.0%) | 0.584 | 25/45 (55.6%) | 14/42 (33.3%) | 0.037 |
| Day 180 | 16/28 (57.1%) | 15/38 (39.5%) | 0.155 | 23/44 (52.3%) | 15/41 (36.6%) | 0.146 |
| Treatment 4 | | | | | | |
| Day 210 | 18/29 (62.1%) | 17/38 (44.7%) | 0.159 | 22/41 (53.7%) | 11/39 (28.2%) | 0.021 |
| Day 240 | 18/29 (62.1%) | 17/35 (48.6%) | 0.280 | 21/41 (51.2%) | 15/36 (41.7%) | 0.402 |
| Day 270 | 16/29 (55.2%) | 19/33 (57.6%) | 0.849 | 24/40 (60.0%) | 19/36 (52.8%) | 0.526 |

[a] Between treatment comparison from Person's chi-square test or Fisher's exact test.
[b] Number of patients with response/number of patients evaluated at time period (percentage).

Decrease from Baseline of 30% or More Headaches Per 30-Day Period in Patients Using and not Using Prophylactic Headache Medications at Baseline The percentages of patients at each assessment time point with at least a 30% decrease from baseline in the frequency of headaches per 30-day period are presented in Table 13 for patients using and not using prophylactic headache medications at baseline.

For patients using prophylactic headache medications at baseline, there were no statistically significant differences between BOTOX® and placebo. For patients not using prophylactic headache medications at baseline, from Day 30 through Day 270 at least 50% of BOTOX®-treated patients had at least a 30% decrease in the frequency of headaches per 30-day period. The differences between BOTOX® and placebo were statistically significant at Days 30, 60, 150, 180, and 210. At these time points, the response rates for BOTOX® was greater than the response rates for placebo by 16.4 to 26.2%.

TABLE 13

Number (Percentage) of Patients with a Decrease from Baseline of 30% or More Headaches per 30-Day Period by Use of Prophylactic Headache Medications at Baseline; Pooled Population

| | Use of Prophylactic Headache Medications at Baseline | | | | | |
|---|---|---|---|---|---|---|
| | Yes | | | No | | |
| Time Period | BOTOX® | Placebo | p-value [a] | BOTOX® | Placebo | p-value [a] |
| Treatment 1: Placebo followed by a 30-day run-in period) | | | | | | |
| Post Placebo Run-in | 15/56 (26.8%) | 18/71 (25.4%) | 0.855 | 24/117 (20.5%) | 29/111 (26.1%) | 0.316 |
| Treatment 2 | | | | | | |
| Day 30 | 21/56 (37.5%) | 28/71 (39.4%) | 0.824 | 61/116 (52.6%) | 40/111 (36.0%) | 0.012 |
| Day 60 | 25/54 (46.3%) | 28/66 (42.4%) | 0.671 | 62/110 (56.4%) | 40/100 (40.0%) | 0.018 |
| Day 90 | 21/53 (39.6%) | 36/63 (57.1%) | 0.060 | 59/96 (61.5%) | 47/94 (50.0%) | 0.112 |
| Treatment 3 | | | | | | |
| Day 120 | 20/34 (58.8%) | 23/39 (59.0%) | 0.990 | 26/46 (56.5%) | 20/43 (46.5%) | 0.345 |
| Day 150 | 18/30 (60.0%) | 26/38 (68.4%) | 0.471 | 35/45 (77.8%) | 24/42 (57.1%) | 0.040 |
| Day 180 | 20/28 (71.4%) | 24/38 (63.2%) | 0.481 | 33/44 (75.0%) | 20/41 (48.8%) | 0.013 |

TABLE 13-continued

Number (Percentage) of Patients with a Decrease from Baseline of 30% or More Headaches per 30-Day Period by Use of Prophylactic Headache Medications at Baseline; Pooled Population

| | Use of Prophylactic Headache Medications at Baseline | | | | | |
|---|---|---|---|---|---|---|
| Time | Yes | | | No | | |
| Period | BOTOX® | Placebo | p-value[a] | BOTOX® | Placebo | p-value[a] |
| | Treatment 4 | | | | | |
| Day 210 | 23/29 (79.3%) | 22/38 (57.9%) | 0.064 | 28/41 (68.3%) | 18/39 (46.2%) | 0.045 |
| Day 240 | 22/29 (75.9%) | 23/35 (65.7%) | 0.376 | 31/41 (75.6%) | 22/36 (61.1%) | 0.171 |
| Day 270 | 20/29 (69.0%) | 23/33 (69.7%) | 0.950 | 30/40 (75.0%) | 23/36 (63.9%) | 0.292 |

[a] Between treatment comparison from Person's chi-square test.

Frequency of Headaches by Disease Onset (10 to 20, >20 Years)

Analyses of the frequency of headaches per 30-day period for patients who were 10 to 20 years and >20 years since disease onset are given in Table 14. The response to BOTOX® was consistently better than the response to placebo over the entire treatment period for patients with disease onset of 10 to 20 years with a statistically significant difference only at Day 180 and for patients with disease onset of >20 years with statistically significant differences at Days 30, 60, and 210. Of note is the observation that for the >20 years subgroup of patients the response to placebo treatment was consistently and considerably lower compared with the response to treatment for the 10 to 20 years subgroup of patients.

Frequency of Headaches by Baseline Headache Day Frequency (20 to 24 and 25 to 30 Headache-Days Per 30-Day Period)

Analyses of the frequency of headaches per 30-day period by headache-day frequency at baseline (20 to 24 and 25 to 30 headache-days) are summarized in Table 15. The response to BOTOX® was consistently better than the response to placebo over the entire treatment period for patients with a baseline headache-day frequency of 20 to 24 with statistically significant differences at Days 60 and 180, and for patients with a baseline headache-day frequency of 25 to 30 with statistically significant differences at Days 30, 60, and 180. At each time point, the difference between the mean changes for BOTOX® and placebo were greater for patients with a baseline headache-day frequency of 25 to 30.

TABLE 14

Mean (Standard Deviation) Baseline and Change from Baseline in the Frequency of Headaches per 30-Day Period by Time from Disease Onset (10 to 20 and >20 Years); Pooled Population

| | Disease Onset 10 to 20 Years | | | Disease Onset >20 Years | | |
|---|---|---|---|---|---|---|
| Time Period | BOTOX® N = 53 | Placebo N = 53 | p-value[a] | BOTOX® N = 46 | Placebo N = 48 | p-value[a] |
| Baseline | 13.2 (7.1) | 11.5 (8.1) | 0.170 | 14.1 (7.9) | 14.2 (9.5) | 0.931 |
| | Treatment 1: Placebo (followed by a 30-day run-in period) | | | | | |
| | Treatment 2 | | | | | |
| Day 30 | −3.6 (5.0) | −3.4 (5.1) | 0.472 | −4.7 (5.0) | −1.9 (4.2) | 0.014 |
| Day 60 | −4.9 (5.0) | −4.1 (4.9) | 0.269 | −5.8 (5.8) | −1.8 (5.2) | 0.003 |
| Day 90 | −4.9 (5.6) | −4.4 (4.9) | 0.693 | −5.4 (5.4) | −2.8 (6.2) | 0.078 |
| | Treatment 3 | | | | | |
| Day 120 | −6.2 (5.8) | −4.5 (5.3) | 0.205 | −6.1 (4.7) | −2.5 (6.3) | 0.107 |
| Day 150 | −7.7 (6.2) | −5.7 (5.1) | 0.244 | −6.3 (5.1) | −3.5 (6.6) | 0.146 |
| Day 180 | −8.1 (6.4) | −4.8 (5.2) | 0.045 | −6.1 (4.6) | −2.3 (6.3) | 0.055 |
| | Treatment 4 | | | | | |
| Day 210 | −8.3 (6.8) | −6.4 (5.7) | 0.256 | −6.7 (6.9) | −1.4 (6.9) | 0.025 |
| Day 240 | −8.2 (6.7) | −6.1 (5.6) | 0.278 | −8.1 (7.8) | −3.4 (6.7) | 0.074 |
| Day 270 | −7.4 (6.2) | −6.3 (6.1) | 0.481 | −8.8 (8.5) | −4.8 (6.9) | 0.209 |

[a] Between treatment comparison from a Wilcoxon rank-sum test.

TABLE 15

Mean (Standard Deviation) at Baseline and Change from Baseline in the Frequency of Headaches per 30-Day Period for Patients with Headache-Day Frequency of 20 to 24 and 25 to 30 per 30-Day Period at Baseline; Pooled Population

| Time Period | Headache-Day Frequency of 20 to 24 Per 30-Day Period | | | Headache-Day Frequency of 25 to 30 Per 30-Day Period | | |
|---|---|---|---|---|---|---|
| | BOTOX® N = 53 | Placebo N = 54 | p-value [a] | BOTOX® N = 70 | Placebo N = 81 | p-value [a] |
| Baseline | 16.6 (5.9) | 14.8 (6.3) | 0.127 | 11.5 (10.0) | 11.5 (10.7) | 0.769 |
| | Treatment 1: Placebo (followed by a 30-day run-in period) | | | | | |
| | Treatment 2 | | | | | |
| Day 30 | −5.7 (5.1) | −4.2 (5.4) | 0.248 | −3.5 (6.4) | −1.2 (4.5) | 0.014 |
| Day 60 | −6.9 (5.7) | −4.7 (5.6) | 0.036 | −3.9 (6.2) | −1.4 (4.9) | 0.015 |
| Day 90 | −6.5 (6.1) | −4.6 (5.7) | 0.158 | −4.0 (6.4) | −2.9 (5.9) | 0.318 |
| | Treatment 3 | | | | | |
| Day 120 | −6.9 (5.9) | −4.6 (6.1) | 0.166 | −4.1 (5.7) | −2.5 (5.9) | 0.154 |
| Day 150 | −9.0 (6.0) | −6.4 (5.7) | 0.137 | −6.2 (6.5) | −2.7 (5.6) | 0.059 |
| Day 180 | −8.9 (6.0) | −5.0 (6.0) | 0.038 | −6.0 (6.0) | −2.5 (5.8) | 0.019 |
| | Treatment 4 | | | | | |
| Day 210 | −9.6 (7.4) | −6.3 (6.1) | 0.064 | −6.5 (7.6) | −2.4 (6.1) | 0.104 |
| Day 240 | −10.1 (7.2) | −6.8 (5.5) | 0.125 | −7.5 (8.6) | −3.1 (6.5) | 0.057 |
| Day 270 | −10.0 (6.1) | −7.3 (6.1) | 0.080 | −7.6 (9.1) | −3.3 (7.7) | 0.139 |

[a] Between treatment comparison from a Wilcoxon rank-sum test.

Frequency of Headaches by Baseline Analgesic Acute Headache Medication Overuse

Medication overuse was defined as use of any acute analgesic medication for ≥15 days and ≥2 days/week. Based on this definition, for patients who did not have overuse of acute analgesic medications at baseline there were no statistically significant differences between BOTOX® and placebo in the changes from baseline in the frequency of headaches per 30-day period at any time point (Table 16). For patients with overuse of acute analgesic medications at baseline, except for Day 90, the difference in the decrease from baseline were significantly greater for BOTOX® than placebo. The mean decreases from baseline were greater for BOTOX® by 2.0 to 5.6 headaches at all time points, except at Day 90 (Table 16).

TABLE 16

Mean (Standard Deviation) at Baseline and Change from Baseline in the Frequency of Headaches per 30-Day Period for Patients with Acute Analgesic Headache Medication Overuse (No, Yes) at Baseline; Pooled Population

| Time Period | Any Analgesic Overuse for ≥15 Days and ≥2 Days/Week, No | | | Any Analgesic Overuse for ≥15 Days and ≥2 Days/Week, Yes | | |
|---|---|---|---|---|---|---|
| | BOTOX® N = 82 | Placebo N = 105 | p-value [a] | BOTOX® N = 91 | Placebo N = 77 | p-value [a] |
| Baseline | 11.7 (6.7) | 11.1 (7.5) | 0.477 | 15.2 (8.2) | 14.9 (8.9) | 0.592 |
| | Treatment 1: Placebo (followed by a 30-day run-in period) | | | | | |
| | Treatment 2 | | | | | |
| Day 30 | −3.5 (4.8) | −2.8 (5.0) | 0.320 | −4.5 (6.1) | −2.5 (4.9) | 0.020 |
| Day 60 | −4.0 (5.3) | −3.7 (5.4) | 0.756 | −5.6 (5.9) | −2.6 (5.2) | 0.001 |
| Day 90 | −4.5 (5.5) | −3.7 (5.8) | 0.726 | −5.2 (6.4) | −3.7 (5.6) | 0.168 |
| | Treatment 3 | | | | | |
| Day 120 | −4.6 (3.9) | −3.6 (6.3) | 0.342 | −6.2 (6.4) | −3.6 (5.2) | 0.044 |
| Day 150 | −5.6 (4.7) | −4.9 (5.7) | 0.585 | −8.2 (6.6) | −4.3 (6.3) | 0.018 |
| Day 180 | −6.1 (4.7) | −3.8 (6.0) | 0.088 | −8.1 (6.3) | −3.6 (6.4) | 0.003 |
| | Treatment 4 | | | | | |
| Day 210 | −5.5 (5.6) | −4.4 (7.1) | 0.495 | −9.3 (7.3) | −3.9 (6.2) | 0.003 |
| Day 240 | −5.7 (4.9) | −5.5 (6.6) | 0.885 | −10.1 (8.1) | −4.5 (6.1) | 0.007 |
| Day 270 | −6.3 (4.9) | −5.8 (7.5) | 0.800 | −9.5 (8.0) | −4.9 (6.4) | 0.017 |

[a] Between treatment comparison from a Wilcoxon rank-sum test.

Frequency of Headaches by Baseline MIDAS Score of Moderate and Severe

Few patients had baseline MIDAS scores of minimal (8 BOTOX®, 10 placebo) or mild (9 BOTOX®, 16 placebo). For patients with a baseline MIDAS score of moderate (21 BOTOX®, 25 placebo), at all time points there were no statistically significant differences between BOTOX® and placebo. However, after Day 60, the mean decreases from baseline were greater for BOTOX® by 2.1 to 5.8 headaches per 30-day period. For patients with a baseline MIDAS score of severe (134 BOTOX®, 131 placebo), the decreases in the frequency of headaches per 30-day period were significantly greater ($p \leq 0.046$) for BOTOX® at Days 30, 60, 180, 210, and 240. At these time points, the mean decreases were greater for BOTOX® by 1.3 to 3.2 headaches per 30-day period.

Type of Headaches

Each headache was classified as migraine (ICHD 1.) or non-migraine (ICHD 2; eg, tension-type headache). All patients experienced at least 1 migraine during the baseline period, suggesting that all patients may actually have a diagnosis of migraine even though this diagnosis was not recognized by the investigator for all patients. It is not unusual for migraine patients to be under diagnosed (Lipton and Stewart, 1998). During the study, patients experienced both migraine and non-migraine headaches. The majority of headaches in both treatment groups were classified as migraine (per the ICHD criteria).

Migraine

The mean baseline and mean changes from baseline in the frequency of migraine (ICHD 1.1 or 1.2) or probable migraine (ICHD 1.5.1) headaches per 30-day period are shown in Table 17. At all time points the decreases from baseline were greater for BOTOX® compared with placebo and were significantly greater ($p \leq 0.048$) at Days 120, 180, and 210. At these time points the mean decreases from baseline were greater for BOTOX® by 1.6 to 2.8 headaches.

TABLE 17

Mean (Standard Deviation) at Baseline and Change from Baseline in the Frequency of Migraine and Probable Migraine Headaches per 30-Day Period; Pooled Population

| Time Period | BOTOX® N = 173 | Placebo N = 182 | p-value [a] |
|---|---|---|---|
| Baseline | 11.2 (6.6) | 10.8 (7.9) | 0.274 |
| Treatment 1: Placebo (followed by a 30-day run-in period) Treatment 2 | | | |
| Day 30 | −3.2 (4.9) | −2.7 (4.4) | 0.335 |
| Day 60 | −3.9 (5.2) | −3.1 (5.0) | 0.134 |
| Day 90 | −3.9 (5.6) | −3.5 (5.3) | 0.768 |
| Treatment 3 | | | |
| Day 120 | −4.7 (5.0) | −3.1 (5.5) | 0.048 |
| Day 150 | −5.7 (5.2) | −3.7 (6.0) | 0.057 |
| Day 180 | −5.8 (5.4) | −3.0 (5.7) | 0.002 |
| Treatment 4 | | | |
| Day 210 | −5.9 (5.9) | −3.3 (6.3) | 0.018 |
| Day 240 | −6.0 (5.6) | −4.2 (5.7) | 0.083 |
| Day 270 | −6.4 (5.8) | −4.3 (6.5) | 0.067 |

[a] Between treatment comparison from a Wilcoxon rank-sum test.

Non-Migraine Headaches

The mean frequency of non-migraine headaches per 30-day period at baseline was 2.3 and 1.8 in the BOTOX® and placebo groups, respectively. There were no statistically significantly differences ($p \geq 0.065$) between BOTOX® and placebo in the changes from baseline in the frequency of non-migraine headaches per 30-day period at all time points except at Day 90 ($p = 0.034$). At all time points after the run-in period, the mean decreases from baseline were greater for BOTOX® by 0.3 to 1.0 non-migraine headaches. At Day 90 the mean decrease was 1.0 for BOTOX® and 0.2 for placebo.

Acute Headache Medication Use

Acute Analgesic Headache Medication Use and Overuse

There were few statistically significant differences between treatment groups in the use of any acute headache medication (eg, triptans, opioids, etc) during any 30-day treatment period. There were also no statistically significant between-group differences for the individual categories of medication, i.e., ergotamines, triptans, simple analgesics, or anti-emetics. There were significant differences between treatment groups for opioids at Day 210 (11.4% [8/70], BOTOX®, 24.7% [19/77] placebo; p=0.038 and for combination therapies at Day 210 (34.3% [24/70] BOTOX®, 18.2% [14/77] placebo; p=0.026) and Day 240 (32.9% [23/70] BOTOX®, 18.3% [13/71] placebo; p=0.048.

Acute medication overuse was defined as ≥15 days/month and ≥2/week for any medication use, simple analgesics, and antiemetics, and ≥10 days per month and ≥2/week for triptans, ergotamines, opioids and combination acute medications. For acute medication overuse, there were no statistically significant between group differences for any acute analgesic, ergotamines, triptans, opioids, combinations, or anti-emetics. Statistically significant between-group differences were observed in the category of simple analgesics at Day 90 (10.1% [15/149] of BOTOX® patients and 3.8% [6/157] of placebo patients [p=0.031]).

Acute Analgesic Headache Medication Use (Number of Days and Number of Uses)

There were no statistically significant differences between the BOTOX® and placebo groups in the number of days with any acute analgesic headache medication use or in the number of uses of any acute analgesic headache medication use at any time point. At all time points, the number of days with any acute analgesic headache medication use and the number of uses of any acute analgesic headache medications was decreased in both treatment groups with greater decreases in the BOTOX® group.

The baseline characteristics of patients overusing and not overusing acute analgesic headache medication at baseline at summarized in Table 18. Patients overusing acute analgesic headache medications were significantly older at baseline (mean age, 45.6 versus 41.6 years; p=0.001), otherwise there were no statistically significant differences between the demographic characteristics of overusers and non-overusers of acute analgesic headache medications at baseline.

TABLE 18

Baseline Characteristics of Patients With and Without Analgesic Headache Medication Overuse at Baseline; Pooled Population

| Baseline Characteristic | Analgesic Headache Medication Overuse [a] at Baseline | | |
|---|---|---|---|
| | Yes N = 168 | No 187 | P-Value |
| Age, mean years (SD) | 45.6 (9.6) | 41.6 (11.0) | 0.001 [b] |
| Sex, n (%) | | | |
| Male | 32 (19.0) | 23 (12.3) | 0.079 [c] |
| Female | 136 (81.0) | 164 (87.7) | |
| Race, n (%) | | | |
| Caucasian | 151 (89.9) | 161 (86.1) | 0.275 [c] |
| Non-Caucasian | 17 (10.1) | 26 (13.9) | |
| Years since onset, mean (SD) | 15.7 (12.6) | 13.5 (12.2) | 0.075 [b] |

TABLE 18-continued

Baseline Characteristics of Patients With and Without Analgesic Headache Medication Overuse at Baseline; Pooled Population

| | Analgesic Headache Medication Overuse [a] at Baseline | | |
|---|---|---|---|
| Baseline Characteristic | Yes N = 168 | No 187 | P-Value |
| Age at onset, mean years (SD) | 29.3 (12.4) | 27.5 (13.4) | 0.153 [b] |
| Prophylactic headache medications, n (%) | 61 (36.3) | 66 (35.3) | 0.842 [c] |
| Beta blockers | 16 (9.5) | 21 (11.2) | 0.599 [c] |
| Calcium channel blockers | 14 (8.3) | 13 (7.0) | 0.624 [c] |
| Anticonvulsants | 23 (13.7) | 27 (14.4) | 0.840 [c] |
| Antidepressants | 38 (22.6) | 36 (19.3) | 0.435 [c] |
| Baseline MIDAS score, mean (SD) | 54.3 (54.7) | 60.6 (55.2) | 0.144 [b] |

TABLE 18-continued

Baseline Characteristics of Patients With and Without Analgesic Headache Medication Overuse at Baseline; Pooled Population

| | Analgesic Headache Medication Overuse [a] at Baseline | | |
|---|---|---|---|
| Baseline Characteristic | Yes N = 168 | No 187 | P-Value |
| Baseline Beck Depression Inventory score, mean (SD) | 7.9 (6.6) | 7.8 (7.1) | 0.577 [b] |

SD = standard deviation.
[a] Overuse = use for ≥15 days and ≥2 days/week
[b] P-values for treatment comparisons from the Wilcoxon rank-sum test.
[c] P-values for treatment comparisons from Pearson's chi-square or Fisher's exact tests.

There were no statistically significant differences between the 2 treatment groups in the change from baseline in the number of uses or in the number of days of use of acute analgesic headache medications at all time points. In both treatment groups, the number of uses and days of use were decreased from baseline and, at all time points there was a greater decrease for BOTOX®-treated than for placebo-treated patients.

Use of any Acute Analgesic Headache Medications in Patients without Headache Prophylaxis Use at Baseline The number of uses of any acute analgesic headache medications and the number of days these medications were used for patients who were not using prophylactic headache medications at baseline and for each 30-day treatment period are summarized in Table 19 and in FIG. 16, respectively.

At all postbaseline time points, in the BOTOX® compared with the placebo group there was a greater decrease in the number of uses of acute analgesic headache medications, with a statistically significant difference at Days 90 and 210 ($p \leq 0.047$). This also was observed in the analysis of the mean number of days acute analgesic headache medications were used, with statistically significant differences at Days 90, 180, 210, and 240 ($p \leq 0.033$).

TABLE 19

Mean (Standard Deviation) at Baseline and Change from Baseline in the Number of Uses and Days of Use of Acute Analgesic Headache Medications per 30-Day Period for Patients Not Using Prophylactic Headache Medications at Baseline; Pooled Population

| | Number of Uses of Analgesic Acute Headache Medications | | | Days with Analgesic Acute Headache Medication Use | | |
|---|---|---|---|---|---|---|
| Time Period | BOTOX® N = 117 | Placebo N = 111 | p-value [a] | BOTOX® N = 117 | Placebo N = 111 | p-value [a] |
| Baseline | 25.1 (17.7) | 21.0 (15.9) | 0.058 | 15.5 (8.4) | 13.5 (8.3) | 0.069 |
| Treatment 1: Placebo (followed by a 30-day run-in period) | | | | | | |
| Treatment 2 | | | | | | |
| Day 30 | −8.7 (13.3) | −5.7 (10.2) | 0.096 | −4.5 (6.3) | −3.3 (5.9) | 0.206 |
| Day 60 | −10.3 (14.8) | −6.4 (10.1) | 0.076 | −5.5 (7.0) | −3.6 (6.6) | 0.052 |
| Day 90 | −10.3 (14.2) | −6.2 (9.9) | 0.047 | −5.7 (6.7) | −3.3 (6.8) | 0.025 |
| Treatment 3 | | | | | | |
| Day 120 | −10.0 (16.7) | −7.7 (9.0) | >0.999 | −5.7 (6.9) | −4.1 (5.9) | 0.427 |
| Day 150 | −13.2 (16.5) | −8.7 (10.6) | 0.199 | −7.9 (6.8) | −5.2 (6.7) | 0.098 |
| Day 180 | −12.9 (15.5) | −7.9 (11.4) | 0.110 | −7.8 (6.3) | −4.1 (6.6) | 0.015 |
| Treatment 4 | | | | | | |
| Day 210 | −14.6 (17.3) | −7.4 (11.3) | 0.018 | −8.5 (7.6) | −4.0 (7.4) | 0.011 |
| Day 240 | −15.8 (18.1) | −8.5 (9.5) | 0.151 | −9.3 (8.1) | −4.7 (7.0) | 0.033 |
| Day 270 | −15.6 (15.9) | −9.2 (11.3) | 0.093 | −8.8 (7.6) | −5.2 (7.3) | 0.086 |

[a] Between treatment comparison from a Wilcoxon rank-sum test.

The study compared BOTOX® and placebo; there was no active control. A range of BOTOX® doses to be used was specified (105 to 260 U), therefore, the exact dose used was not fixed. Depending on the location and severity of the patients' headache pain, the number of injection sites and the dosage to be administered for the specified frontal and posterior muscle areas, could be customized for each patient (within a specified range). Therefore, a dose-response effect could not be evaluated. The same dose and injection administered for treatment 1 was to be replicated at each subsequent treatment.

Overall, 97.7% ($^{347}/_{355}$) of patients received acute headache medications while in the study, with similar proportions in each treatment group: 98.3% ($^{170}/_{173}$) of patients in the BOTOX® group and 97.3% ($^{177}/_{182}$) in the placebo group.

The most common classes of concomitant acute headache medications (>10%) taken during the study were selective 5HT1-receptor agonists (67.0%, $^{238}/_{355}$), anilides (62.3%, $^{221}/_{355}$), propionic acid derivatives (55.2%, $^{196}/_{355}$), all other therapeutic products (39.4%, $^{140}/_{355}$), natural opium alkaloids (22.3%, 79/355), unknown class (15.8%, 56/355), salicylic acid and derivatives (14.6%, 52/355), and hypnotics and sedatives (13.5%, 48/355). There were no notable differences in the types or frequencies of acute headache medication use between the BOTOX® and placebo groups.

Overall, 87.6% (311/355) of patients received concomitant medications (other than acute headache medications), with similar proportions in each treatment group: 90.2% (156/173) of patients in the BOTOX® group and 85.2% (155/182) in the placebo group.

The most common classes of concomitant medications (>10%) taken during the study were selective serotonin reuptake inhibitors (21.4%, 76/355), non-selective monoamine reuptake inhibitors (16.9%, 60/355), natural and semisynthetic estrogens (15.2%, 54/355), thyroid hormones (11.5%, 41/355), benzodiazepine derivatives (11.3%, 40/355), and progestogens and estrogens/fixed combinations (11.0%, 39/355). There were no notable differences in the types or frequencies of concomitant medication use between the BOTOX® and placebo groups.

A total of 35.8% (127/355) of patients were taking a headache prophylaxis medication during baseline. These included 10.4% (37/355) on beta blockers, 7.6% (27/355 on calcium channel blockers, 14.1% (50/355) on anti-convulsants, and 20.8% (74/355) on anti-depressants. There were no statistically significant differences between the BOTOX® and placebo groups in the number of patients using any of the aforementioned headache prophylactic medications.

Efficacy Conclusions

In this phase 2 study the secondary endpoint of the proportion of patients with a decrease from baseline of 50% or more headache days per 30-day period in the non-responder strata was met. There were occasional statistically significant differences in the analyses of other protocol-designated variables (eg, frequency of headaches, incidence of subjects with a decrease from baseline of 50% or more headaches per 30-day period, frequency of migraines per 30-day period) when analyses were performed on both placebo non-responders and placebo responder subpopulations. No treatment-by responder interaction was statistically significant; therefore, stratification by respond/nonresponder was not necessary.

Further post hoc analyses were performed that identified the following patient populations that were most responsive to treatment with BOTOX® relative to placebo:

The pooled placebo non-responder and placebo responder stratum (pooled population).
Patients not using prophylactic headache medication at baseline compared with patients using prophylactic headache medications at baseline.
Patients with more frequent days of headache at baseline (i.e., 20 to 24 and 25 to 30 headache days) compared with those with less frequent days of headache at baseline (i.e., <20 headache days).
Patients with more years of chronic headache disease (i.e., >20 years) compared with those with less chronicity (i.e., <10 years and 10 to 20 years).
Patients with acute analgesic medication overuse at baseline compared with those without acute analgesic medication overuse.

From the post hoc analyses of the pooled population of patients, it is concluded that:

There was a persistent statistically significant decrease in the frequency of headaches for patients treated with BOTOX® compared with placebo at multiple timepoints. There was an accompanying decrease in the use of and days of use of any acute analgesic headache medications for patients treated with BOTOX® compared with those treated with placebo.

The efficacy endpoint that best demonstrated BOTOX® efficacy over placebo was the frequency of headaches per 30-day period.

During the placebo run-in period (first treatment cycle 1, Day −30 to Day 0) all patients received placebo on Day −30. On Day 0, patients were randomized to receive 3 treatment cycles of intramuscular injections of BOTOX® or placebo. Of the 355 patients enrolled in the study, 173 received 105 U to 260 U BOTOX® and 182 received placebo. The maximum dose of BOTOX® that patients could have received according to the protocol was 260 U per treatment cycle for each of 3 treatment cycles for a total cumulative exposure of 780 U.

Dose

The mean (median) total dose of BOTOX® for the second, third, and fourth treatment cycles was 190.8 U (200 U), 190.9 U (200 U), and 190.5 U (200 U), respectively. The mean and median doses of BOTOX® injected into each muscle group for the second, third, and fourth treatment cycles are presented in Table 20. Of note is the observation that the optional injection of the masseter was administered to less than half of the patients in both the BOTOX® and placebo groups.

TABLE 20

Mean (Median) Dose of BOTOX ® Injected into Each Muscle Group per Treatment

| Muscle Injected (Allowable Dose Range) | Treatment Cycle 2 (Day 0) | Treatment Cycle 3 (Day 90) | Treatment Cycle 4 (Day 180) |
|---|---|---|---|
| Frontal/glabellar (25 to 40 U) | 38.0 U (40 U) | 37.3 U (40 U) | 37.1 U (40 U) |
| Occipitalis (20 U) | 19.8 U (20 U) | 19.8 U (20 U) | 19.7 U (20 U) |
| Temporalis (20 to 50 U) | 42.0 U (40 U) | 42.7 U (45 U) | 43.7 U (45 U) |
| Masseter (optional; 0 to 50 U) | 8.0 U (0 U) | 7.6 U (0 U) | 6.5 U (0 U) |
| Trapezius (20 to 60 U) | 47.4 U (60 U) | 48.3 U (60 U) | 48.4 U (60 U) |
| Semispinalis (10 to 20 U) | 18.2 U (20 U) | 18.0 U (20 U) | 17.9 U (20 U) |
| Splenius capitis (10 to 20 U) | 18.6 U (20 U) | 18.1 U (20 U) | 18.1 U (20 U) |

Note:
During treatment cycle 1 all patients were treated with placebo.

Number of Sites Injected

The mean (median) total number of sites injected with BOTOX® for the first, second, and third treatments was 32.0 (30), 31.6 (29) and 31.8 (29), respectively. The mean (median) number of sites injected with BOTOX® per muscle group for the first, second, and third injections are presented in Table 21.

TABLE 21

Mean (Median) Number of Sites BOTOX ® Injected per Muscle Group per Treatment Cycle

| Muscle Injected (Allowable Dose Range) | Treatment Cycle 2 (Day 0) | Treatment Cycle 3 (Day 90) | Treatment Cycle 4 (Day 180) |
|---|---|---|---|
| Frontal/glabellar (25 to 40 U) | 9.5 (9.0) | 9.8 (10.0) | 9.7 (10.0) |

TABLE 21-continued

Mean (Median) Number of Sites BOTOX ® Injected per Muscle Group per Treatment Cycle

| Muscle Injected (Allowable Dose Range) | Treatment Cycle 2 (Day 0) | Treatment Cycle 3 (Day 90) | Treatment Cycle 4 (Day 180) |
|---|---|---|---|
| Occipitalis (20 U) | 3.0 (2.0) | 2.8 (2.0) | 2.9 (2.0) |
| Temporalis (20 to 50 U) | 6.5 (6.0) | 6.3 (6.0) | 6.4 (6.0) |
| Masseter (optional; 0 to 50 U) | 1.3 (0.0) | 1.2 (0.0) | 1.2 (0.0) |
| Trapezius (20 to 60 U) | 5.9 (6.0) | 6.0 (6.0) | 6.0 (6.0) |
| Semispinalis (10 to 20 U) | 3.0 (2.0) | 2.9 (2.0) | 2.9 (2.0) |
| Splenius capitis (10 to 20 U) | 3.1 (2.0) | 2.9 (2.0) | 3.0 (2.0) |

Note:
During treatment cycle 1 all patients were treated with placebo.

DISCUSSION

Chronic daily headache refers to a group of disorders characterized by high frequency of headaches, often associated with considerable disability (Welch and Goadsby, 2002). Mathew et al (1987) reported that 78% of CDH patients from their clinic had evolved out of a prior history of episodic migraine. According to Holroyd et al (2000) patients with CDH report their role functioning and well-being as frequently and severely impaired, highlighting the impact of this disease on quality of life (Monzon and Lainez, 1998; Wang et al, 2001). There is still no satisfactory therapeutic approach for these patients (Silvestrini et al, 2003).

Pathophysiological considerations suggest that the possible basis for the shift from episodic to chronic headache can be progressive changes in the activity of central nociceptive system (Hering et al, 1993). BOTOX® has been shown to have antinociceptive effects (Cui, 2004). This observation could explain its efficacy in the treatment of migraine that has been reported in the literature (Binder, et al, 2000; Klapper et al, 2000; Mathew et al, 2003; Mauskop, 1999; Ondo et al, 2004). This study explored the potential benefit of BOTOX® treatment in the CDH population. A modified follow-the-pain treatment paradigm was used in this study. All patients received at least 105 U, the minimum dose, every 3 months for up to 3 treatment cycles. This minimum dose required injection into six specific muscles (bilateral when appropriate) with a minimum dose per muscle specified in the protocol. Investigators were allowed to individualize the treatment for each patient based on the location and severity of their headache pain. The maximum dose allowed into 7 specified muscles was 260 U (for a maximum total exposure of 780 U over the 3 treatment cycles). The protocol specified the maximum dose per muscle and a maximum imbalance for bilateral muscle treatment. In this study the average total dose received was 190 U.

Significant and consistent efficacy favoring BOTOX® over placebo was observed for the change from baseline in the frequency of headaches per 30-day period. These changes were observed in the placebo non-responder and the placebo responder strata, the pooled data, and in the subgroup of patients with no baseline headache prophylactic treatment. Change in the frequency of headache is a preferred primary endpoint in migraine trials (European Agency for the Evaluation of Medicinal Products, 2003). Recent US FDA approved prophylactic treatment for migraine headache also established efficacy by measuring a change in frequency of headaches (Depakote package insert, 2003).

Based on the data for headache frequency, BOTOX® demonstrated an initial onset of action within 30 days of the first active treatment. The response at Day 180 in those patients who completed 2 or 3 injection cycles was similar and ranged from −7.1 to −8.0 headaches in the BOTOX® group (baseline=14) and −3.7 to −5.4 headaches in the placebo group (baseline=13) (p<0.042 from Day 180 through Day 270). A majority of headaches experienced by patients in this study were greater than 4 hours in duration. In addition to showing that BOTOX® treatment resulted in a clinically and statistically significant decrease of all headaches, regardless of duration, there was a clinically and statistically significant difference (favoring BOTOX®) in the change in the frequency of headaches ≥4 hours in duration. The response at Day 180 in those patients with headaches of ≥4 hours duration was −4.6 headaches in the BOTOX® group versus −2.2 in the placebo group (baseline=9.6 and 9.2, respectively; p=0.005). In patients with headaches <4 hours, there was a decrease of −2.5 headaches in the BOTOX® group and −1.6 headaches in the placebo group (baseline=3.9 and 3.5, respectively). This demonstrates that BOTOX® treatment reduced the number of headaches of substantial clinical burden.

The incidence of patients experiencing a decrease in the frequency of headaches per 30-day period provides information on the effectiveness of BOTOX® as a headache prophylaxis treatment for the target population. Although not a requirement for entry, all of the patients in this study had a migraine headache during the baseline period (ICHD level 1), supporting the underlying primary headache diagnosis of migraine and not tension-type headache. Therefore, the actual population studied was migraine patients with CDH.

Significant differences were found between the groups favoring BOTOX® in the percentage of patients with a decrease from baseline of at least 50% or more per 30-day period in the number of headaches at Day 180 (54.2% vs 38.0%, p=0.046) and Day 210 (57.1% vs 36.4%, p=0.012). In addition, the percentage of patients with a 50% decrease in headaches per 30-day period occurred in more than 50% of patients at Days 150, 180, 210, 240, and 270 in the BOTOX® group, while this level was reached only at Day 270 in the placebo group.

The population of patients who were not using a prophylactic headache medication at baseline was a subgroup responding to treatment with BOTOX®. Statistically significant between-group differences were observed for efficacy favoring BOTOX® for the mean change from baseline in the frequency of headaches as well as other efficacy variables such as: 50% reduction from baseline in the frequency of headaches per 30-day period, 30% reduction from baseline in the frequency of headaches per 30-day period, number of headache days, and number of uses and days of use of acute analgesic headache medication per 30-day period.

Frequent use of analgesic medications is an important factor to consider in the CDH population since patients with CDH may be overusing acute analgesic medications (Colas et al, 2004). Currently the definition of "analgesic medication overuse" is under discussion by the headache-research community (Bigal et al, 2002; Silberstein et al, 1994), and the Headache Classification Subcommittee of the International Headache Society (Silberstein [chair of the subcommittee for defining the IHS criteria for medication overuse] verbal communication, June, 2004). The most recently proposed definition under consideration is any use of ≥15 days and ≥2 days per week (Silberstein verbal communication, 2004).

In this study, patients were to be excluded if, in the investigator's opinion, the patient was overusing an analgesic medication. To investigate the ≥15 days and ≥2 days per week definition post hoc in this population, patients were stratified into 2 groups: "yes" (patient is an analgesic medication overuser) or "no" (patient is not an analgesic medication overuser). A total of 52.6% ($^{91}/_{173}$) of BOTOX® patients and 42.3% ($^{77}/_{182}$) of placebo patients in this study met this criterion for analgesic medication overuse at baseline. The mean decreases from baseline in the frequency of headaches per 30-day period in the "yes" analgesic medication overuse subgroup were significantly greater for BOTOX® than for placebo by 2.0 to 5.6 headaches at all time points, except for Day 90.

Frequent analgesic use has been suggested as a cause for CDH (Linton-Dahlöf et al, 2000). However, some have suggested that frequent analgesic use may simply follow the increasing frequency of headache (Lipton and Bigal, 2003). Regardless, analgesic medication overuse is a condition that greatly decreases patients' quality of life and adds significant socioeconomic burden to their care (Colas et al, 2004; Bigal et al, 2002; Schwartz et al, 1997). BOTOX® as a preventative agent for patients with migraine and CDH may prove to be important in reducing the frequency of headaches, as well as reducing analgesic medication use, and possibly analgesic medication overuse.

This study demonstrated that BOTOX® is effective and well tolerated in migraine patients with CDH, and offers an alternative to other prophylactic therapies in which the high incidence and severity of adverse events affects patient compliance.

The secondary endpoint of incidence of patients with 50% or more decrease in frequency of headache days was achieved at Day 180 in the placebo non-responder group. In all efficacy analyses, there was a strong response to treatment with BOTOX®. A priori and post hoc analyses identified several patient populations for whom treatment with BOTOX® showed statistically significant differences over placebo. Statistically significant findings at multiple timepoints for multiple efficacy parameters were found in the subgroup of patients not taking a headache prophylaxis at baseline. With regard to endpoints, the frequency of headaches per 30-day period best demonstrated BOTOX® effectiveness over placebo. Additionally, there was a significantly greater decrease in the use and days of use of acute analgesic headache medications for patients treated with BOTOX® compared to those treated with placebo, particularly in the subgroup of patients not taking a headache prophylaxis at baseline. BOTOX® was also shown to be safe and well tolerated in this modified follow-the-pain regimen, when administered every 3 months in doses up to 260 U per treatment cycle.

A botulinum toxin type B, C, D, E, F or G can be substituted for the botulinum toxin type A used above, for example by use of about 10,000 units of a botulinum toxin type B, that is by use of about fifty times the amount of the botulinum toxin type A used in the study set forth in Example 1.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods to alleviate a headache pain or to reduce the number of headaches wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type B. Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin to prove adjunct effect such as enhanced or a more rapid onset of denervation before the neurotoxin, such as a botulinum toxin, begins to exert its therapeutic effect.

A method for treating a disorder according to the invention disclosed herein has many benefits and advantages, including the following:

1. Headaches can be eliminated.

2. symptoms of pain, such as a headache pain can be dramatically reduced or eliminated.

3. the symptoms of a pain can be reduced or eliminated for at least about two to about six months per injection of neurotoxin and for from about one year to about five years upon use of a controlled release neurotoxin implant.

4. headaches can be eliminated for at least about two to about six months per injection of neurotoxin and for from about one year to about five years.

5. a medication overuse disorder, such as MOH, can be effectively treated.

6. the efficacy of a triptan medication can be increased.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods wherein two or more Clostridial neurotoxins, such as two or more botulinum toxins, are administered concurrently or consecutively. For example, botulinum toxin type A can be locally administered until a loss of clinical response or neutralizing antibodies develop, followed by administration of botulinum toxin type B. Furthermore, non-neurotoxin compounds can be locally administered prior to, concurrently with or subsequent to administration of the neurotoxin to provide adjunct effect such as enhanced or a more rapid onset of pain suppression before the neurotoxin, such as a botulinum toxin, begins to exert its more long lasting pain and MOH suppressant effect.

Our invention also includes within its scope the use of a neurotoxin, such as a botulinum neurotoxin, in the preparation of a medicament for the treatment of a medication overuse disorder, by local administration of the botulinum toxin.

All references, articles, patents, applications and publications set forth above are incorporated herein by reference in their entireties.

Accordingly, the spirit and scope of the following claims should not be limited to the descriptions of the preferred embodiments set forth above.

We claim:

1. A method for treating or reducing the occurrence of a symptom of a medication overuse disorder in a patient in need thereof, the method comprising local administration by injection of a composition comprising a botulinum toxin type A, wherein the number of injection sites is 23 to 58, the number of muscle areas injected is 6 to 7 and the botulinum toxin type A dose is 105 to 260 units, and wherein at least the frontal/glabellar, occipitalis, temporalis, semispinalis, splenius capitis or trapezius muscles are injected.

2. The method of claim 1, wherein the administration is subdermal or subcutaneous.

3. The method of claim 1, wherein the medication overuse disorder is selected from triptan, opiod overuse disorder and combinations thereof.

4. The method of claim 3, wherein the medication overuse disorder is a triptan overuse disorder.

5. The method of claim 3, wherein the medication overuse disorder is an opioid overuse disorder.

6. The method of claim 3, wherein the symptom of medication overuse disorder is selected from headache, daily use of acute pain medications, and combinations thereof.

7. The method of claim 1, wherein the administration is intramuscular.

8. A method for treating or reducing the occurrence of a headache in a patient with a medication overuse headache disorder, the method comprising local administration by injection of a composition comprising a botulinum toxin type A, wherein the number of injection sites is 23 to 58, the number of muscle areas injected is 6 to 7 and the botulinum toxin type A dose is 105 to 260 units, and wherein at least the frontal/glabellar, occipitalis, temporalis, semispinalis, splenius capitis or trapezius muscles are injected.

* * * * *